(12) United States Patent
Jin

(10) Patent No.: US 8,048,636 B2
(45) Date of Patent: Nov. 1, 2011

(54) METHODS OF SCREENING FOR MODULATORS OF H2-CALPONIN ACTIVITY

(75) Inventor: Jian-Ping Jin, Northbrook, IL (US)

(73) Assignee: Northshore University Healthsystem

( * ) Notice: Subject to any disclaimer, the term of this patent is extended or adjusted under 35 U.S.C. 154(b) by 441 days.

(21) Appl. No.: 12/043,013

(22) Filed: Mar. 5, 2008

(65) Prior Publication Data

US 2008/0220443 A1 Sep. 11, 2008

Related U.S. Application Data

(60) Provisional application No. 60/893,099, filed on Mar. 5, 2007.

(51) Int. Cl.
*G01N 33/53* (2006.01)
(52) U.S. Cl. .............................. 435/7.1; 435/7.2; 436/518
(58) Field of Classification Search ........................ None
See application file for complete search history.

(56) References Cited

U.S. PATENT DOCUMENTS

2002/0160386 A1* 10/2002 Goodearl et al. ................. 435/6
2003/0054453 A1* 3/2003 Curtis et al. .................. 435/69.1

OTHER PUBLICATIONS

Tang et al. (J. Biol. Chem. 2003 vol. 281, p. 6664-6672).*
Hossain et al. (J. Bio. Chem 2005 vol. 280, p. 42442-42453).*
Hossain et al. (II) (Am J Physiology 2003 vol. 284, p. c156-c167.*
Berg Angew Chem Int. Edt. 2003 vol. 42, p. 2462-2481.*
Abe et al., Effect of calponin on actin-activated myosin ATPase activity, *J. Biochem.* 108: 835-8 (1990).
Allen et al., The biochemical basis of the regulation of smooth muscle contraction, *Trends Biochem. Sci.* 19: 362-8 (1994).
Applegate et al., Cloning and expression of a novel acidic calponin isoform from rat aortic vascular smooth muscle, *J. Biol. Chem.* 269: 10683-90 (1994).
Aziz et al., Development of macrophages with altered actin organization in the absence of MafB, *Mol Cell Biol.* 26: 6808-18 (2006).
Beningo et al., Fc-receptor-mediated phagocytosis is regulated by mechanical properties of the target, *J. Cell Sci.* 115: 849-56 (2002).
Collins et al., Terminal differentiation of human promyelocytic leukemia cells induced by dimethyl sulfoxide and other polar compounds, *Proc. Natl. Acad. Sci. USA* 75: 2458-62 (1978).
Conrad et al., Optimized vector for conditional gene targeting in mouse embryonic stem cells, *Biotechniques* 34: 1136-40 (2003).
Discher et al., Tissue cells feel and respond to the stiffness of their substrate, *Science* 310: 1139-43 (2005).
Gao et al., Complete nucleotide sequence, structural organization and an alternatively spliced exon of mouse h1-calponin gene, *Biochem. Biophys. Res. Commun.* 218: 292-7 (1996).
Gordon et al., The macrophage: Past, present and future, *Eur. J. Immunol.* 37: S9-S17 (2007).
Haeberle et al., Calponin decreases the rate of cross-bridge cycling and increases maximum force production by smooth muscle myosin in an in vitro motility assay, *J. Biol. Chem.* 269: 12424-31 (1994).

Horiuchi et al., The mechanism for the inhibition of actin-activated ATPase of smooth muscle heavy meromyosin by calponin, *Biochem. Biophys. Res. Comm.* 176: 1487-93 (1991).
Hossain et al., Cytoskeletal tension regulates both expression and degradation of h2-calponin in lung alveolar cells, *Biochemistry* 45: 15670-83 (2006).
Hossain et al., Developmentally regulated expression of calponin isoforms and the effect of h2-calponin on cell proliferation, *Am. J. Physiol Cell Physiol.* 284: C156-67 (2003).
Hossain et al., H2-calponin is regulated by mechanical tension and modifies the function of actin cytoskeleton, *J. Biol. Chem.* 280: 42442-53 (2005).
Huang et al., Genomic sequence and structural organization of mouse slow skeletal muscle troponin T gene, *Gene* 229: 1-10 (1999).
Huang et al., Increased macrophage activation mediated through toll-like receptors in rheumatoid arthritis, *Arthritis Rheum.* 56: 2192-201 (2007).
Ichinose et al., Enhancement of phagocytosis in mouse macrophages by pituitary adenylate cyclase activating polypeptide (PACAP) and related peptides, *Immunopharmacol.* 30: 217-24 (1995).
Jin et al., Epitope structure and expression of calponin in different smooth muscles and during development, *Biochem. Cell Biol.* 74: 187-96 (1996).
Jin et al., Expression and purification of the h1 and h2 isoforms of calponin, *Protein Expr. Purif.* 31: 231-9 (2003).
Jones et al., Cellular signaling in macrophage migration and chemotaxis, *J. Leukoc. Biol.* 68: 593-602 (2000).
Le et al., Tumor necrosis factor and interleukin 1 can act as essential growth factors in a murine plasmacytoma line, *Lymphokine Res.* 7: 99-106 (1988).
Ley et al., Getting to the site of inflammation: The leukocyte adhesion cascade updated, *Nat. Rev. Immunol.* 7: 678-89 (2007).
Lin et al., Monoclonal antibodies against chicken tropomyosin isoforms: Production, characterization, and application, *Hybridoma* 4: 223-42 (1985).
Lin et al., Tropomyosin isoforms in nonmuscle cells, *Int. Rev. Cytol.* 170: 1-38 (1997).
Liu et al., Constitutively activated Akt-1 is vital for the survival of human monocyte-differentiated macrophages. Role of mcl-1, independent of nuclear factor (nf)-kappa b, bad, or caspase activation, *J. Exp. Med.* 194: 113-26 (2001).
Liu et al., Mcl-1 is essential for the survival of synovial fibroblasts in rheumatoid arthritis, *J Immunol.* 175: 8337-45 (2005).
Liu et al., Prostate cancer chemoprevention agents exhibit selective activity against early state prostate cancer cells, *Prost. Cancer Prost. Dis.* 4:81-91 ( 2001).
Liu et al., Serine phosphorylation of STAT3 is essential for Mcl-1 expression and macrophage survival, *Blood* 102: 344-52 (2003).
Liu et al., Transcriptional diversity during monocyte to macrophage differentiation, *Immunol. Lett.* 117: 70-80 (2008).
Ma et al., Fas ligation on macrophages enhances IL-1R1-Toll-like receptor 4 signaling and promotes chronic inflammation, *Nat. Immunol.* 5: 380-7 (2004).

(Continued)

*Primary Examiner* — Jacob Cheu
(74) *Attorney, Agent, or Firm* — Marshall, Gerstein & Borun LLP

(57) ABSTRACT

The invention provides methods for identifying modulators of mammalian, e.g., human, h2-calponin, the calponin isoform of relatively neutral pI. H2-calponin exerts an effect on the migration and proliferation of a variety of muscle (smooth muscle) and non-muscle cells and is an actin filament-associated regulatory protein influencing the structure of the actin cytoskeleton. Modulators of the activity levels of this protein are useful in preventing, ameliorating, or treating a variety of diseases, disorders or conditions characterized by aberrant cell migration and/or cell proliferation.

10 Claims, 30 Drawing Sheets

OTHER PUBLICATIONS

McKinney et al., Stretch-induced injury of cultured neuronal, glial, and endothelial cells. Effect of polyethylene glycol-conjugated superoxide dismutase, *Stroke* 27: 934-40 (1996).

Meyers et al., An Fgf8 mutant allelic series generated by Cre- and Flp-mediated recombination, *Nat. Genet.* 18: 136-41 (1998).

Miyado et al., Decreased expression of a single tropomyosin isoform, TM5/TM30nm, results in reduction in motility of highly metastatic B16-F10 mouse melanoma cells, *Biochem. Biophys. Res. Commun.* 225: 427-35 (1996).

Nakamura et al., Suppression of syntheses of high molecular weight nonmuscle tropomyosins in macrophages, *Cell Motil. Cytoskeleton* 31: 273-82 (1995).

Nigam et al., h1- and h2-calponins are not essential for norepinephrine- or sodium fluoride-induced contraction of rat aortic smooth muscle, *J. Muscle Res. Cell Motil.* 19: 695-703 (1998).

Nishida et al., cDNA cloning and mRNA expression of calponin and SM22 in rat aorta smooth muscle cells, *Gene* 130: 297-302 (1993).

Oda et al., A new simple fluorometric assay for phagocytosis, *J. Immunol Methods* 88: 175-83 (1986).

Pagliari et al., Macrophages require constitutive NFkappaB activation to maintain A1 expression and mitochondrial homeostasis, *Mol. Cell. Biol.* 20: 8855-65 (2000).

Perlman et al., FLICE-inhibitory protein expression during macrophage differentiation confers resistance to fas-mediated apoptosis, *J. Exp. Med.* 190: 1679-88 (1999).

Raschke et al., Functional macrophage cell lines transformed by Abelson leukemia virus, *Cell* 15: 261-7 (1987).

Schonlau et al., Monocyte and macrophage functions in M-CSF-deficient op/op mice during experimental leishmaniasis, *J. Leukoc. Biol.* 73: 564-73 (2003).

Scott et al., Phagocytosis and clearance of apoptotic cells is mediated by MER, *Nature* 411: 207-11 (2001).

Shirinsky et al., Inhibition of the relative movement of actin and myosin by caldesmon and calponin, *J. Biol. Chem.* 267: 15886-92 (1992).

Strasser et al., Mammalian calponin. Identification and expression of genetic variants, *FEBS Lett.* 330: 13-8 (1993).

Tacke et al., Migratory fate and differentiation of blood monocyte subsets, *Immunobiology* 211: 609-18 (2006).

Takahashi et al., Isolation and characterization of a 34,000-dalton calmodulin- and F-actin-binding protein from chicken gizzard smooth muscle, *Biochem. Biophys. Res. Commun.* 141: 20-6 (1986).

Takahashi et al., Molecular cloning and sequence analysis of smooth muscle calponin, *J. Biol. Chem.* 266: 13284-8 (1991).

Thomas et al., Site-directed mutagenesis by gene targeting in mouse embryo-derived stem cells, *Cell* 51: 503-12 (1987).

Trabelsi-Terzidis et al., Expression of an acidic isoform of calponin in rat brain: Western blots on one- or two dimensional gels and immunolocalization in cultured cells, *Biochem. J.* 306: 211-5 (1995).

van den Berg et al., A function for the macrophage F4/80 molecule in tolerance induction, *Trends Immunol.* 26: 506-9 (2005).

von Kleist et al., Immunohistology of the antigenic pattern of a continuous cell line from a human colon tumor, *J. Natl. Cancer Inst.* 55: 555-60 (1975).

Walsh, Calcium-dependent mechanisms of regulation of smooth muscle contraction, *Biochem. Cell. Biol.* 69: 771-800 (1991).

Winder et al., Calponin phosphorylation in vitro and in intact muscle, *Biochem. J.* 296: 827-36 (1993).

Winder et al., Smooth muscle calponin: Inhibition of actomyosin MgATPase and regulation by phosphorylation, *J. Biol. Chem.* 265: 10148-55 (1990).

Yeh et al., Cell surface antigens of human melanoma identified by monoclonal antibody, *Proc. Natl. Acad. Sci. USA* 76: 2927-31 (1979).

* cited by examiner ated on a cell comprising h2-calponin. A suitable cell is selected from the group consisting of an epidermal keratinocyte, a lung alveolar cell, a cornea epithelial cell, an endothelial cell, a kidney podocyte, an osteoblast, a fibroblast, a monocyte, a macrophage, a neutrophil, a myoblast, an embryonic stem cell and a cancer cell. For example, the cell may be selected from the group consisting of a cornea epithelial cell, an endothelial cell, a kidney podocyte, an osteoblast, a monocyte, a macrophage, a neutrophil, a myoblast and an embryonic stem cell. Also contemplated are screening methods in which the h2-calponin is isolated from an endogenous source or is produced recombinantly. Preferably, the h2-calponin is a mammalian h2-calponin, such as a human h2-calponin.

METHODS OF SCREENING FOR MODULATORS OF H2-CALPONIN ACTIVITY

This invention was made with U.S. government support under grant numbers HL-086720, AR-049217, and AR048269 awarded by the National Institutes of Health. The government has certain rights in the invention.

FIELD

The invention relates to the field of medicine. More particularly, the invention relates to cell migration and cell proliferation.

BACKGROUND

Calponin is an actin filament-associated regulatory protein. H2-calponin is a member of the calponin family that includes two other homologous isoforms, h1-calponin and acidic calponin. The extensively studied h1-calponin is specific to differentiated smooth muscle cells. H2-calponin is found in smooth muscle and a number of non-muscle cells with a potentially broad physiological function. As an interesting example, endothelial cells express a substantial level of h2-calponin, implicating a functional significance for this protein not necessarily shared by its homologous isoforms. Endothelial cell proliferation and migration are critical for proper vascular development and wound healing. Over-expression of h2-calponin inhibits cell proliferation.

SUMMARY

The invention provides materials and methods for controlling the activity levels of h2-calponin (neutral calponin, calponin 2, CNN2), a protein exerting significant influence on the migration and proliferation of a variety of cell types found in mammals such as humans. The activity level of h2-calponin can be altered by altering its level of expression or by expressing an h2-calponin mutein having a different specific activity relative to wild-type h2-calponin. As a practical matter, the former approach to altering activity levels is preferred as it is more amenable to alteration of activity than is the substitution of a variant protein for the native protein expressed in the cells of an organism. Accordingly, the invention provides methods of preventing, ameliorating, and/or treating cancers, atherosclerosis, ischemic heart diseases, autoimmune diseases, and wound healing, as well as methods of reducing scar formation, methods of improving lung protection and/or preservation, methods of promoting bone formation, methods of promoting myogenesis and tissue repair, and methods of minimizing or reversing abnormal cell proliferation and/or cell migration. Each of these methods of the invention comprises efforts to control the activity level of h2-calponin in one or more cell types. The invention further provides diagnostic methods comprising comparative measurements of h2-calponin activity levels in cells of interest and control cells, providing a basis for diagnosing a disease such as myeloid leukemia.

According, in one aspect the invention provides a method of screening for a modulator of h2-calponin comprising: (a) contacting h2-calponin with a candidate modulator; (b) determining the activity of said h2-calponin in the presence and absence of the candidate modulator; and (c) identifying said candidate modulator as a modulator of h2-calponin if the activity of h2-calponin differs in the presence and absence of said candidate modulator. In some embodiments, the h2-calponin is intracellular h2-calponin, i.e., the screen is performed on a cell comprising h2-calponin. A suitable cell is selected from the group consisting of an epidermal keratinocyte, a lung alveolar cell, a cornea epithelial cell, an endothelial cell, a kidney podocyte, an osteoblast, a fibroblast, a monocyte, a macrophage, a neutrophil, a myoblast, an embryonic stem cell and a cancer cell. For example, the cell may be selected from the group consisting of a cornea epithelial cell, an endothelial cell, a kidney podocyte, an osteoblast, a monocyte, a macrophage, a neutrophil, a myoblast and an embryonic stem cell. Also contemplated are screening methods in which the h2-calponin is isolated from an endogenous source or is produced recombinantly. Preferably, the h2-calponin is a mammalian h2-calponin, such as a human h2-calponin.

Embodiments of this aspect of the invention include methods wherein the modulator inhibits the activity of h2-calponin. In some embodiments, the modulator inhibits activity by inducing h2-calponin degradation. An exemplary form of h2-calponin degradation is degradation by protease activity. Modulators that inhibit h2-calponin activity include, but are not limited to, inhibitors of myosin II ATPase and anti-h2-calponin antibodies, as well as fragments, variants, fusions and alternate antibody forms provided that these molecules retain the capacity to specifically bind to h2-calponin and inhibit its activity (e.g., effect on cell proliferation and/or cell migration of at least one cell type identified herein as susceptible to influence by h2-calponin).

In other embodiments, the screening methods identify modulators that increase the activity of h2-calponin. Modulators that increase the activity of h2-calponin include, but are not limited to, anti-h2-calponin antibodies, as well as fragments, variants, fusions and alternate antibody forms that retain the capacity to specifically bind to h2-calponin and increase h2-calponin activity. H2-calponins suitable for use in one of the screening assays include a mammalian h2-calponin, such as the human h2-calponin comprising the sequence set forth in SEQ ID NO:1, the human calponin 2 (variant 1) comprising the sequence set forth in SEQ ID NO:17, the human calponin 2 (variant 2) comprising the sequence set forth in SEQ ID NO:19, the mouse h2-calponin comprising the sequence set forth in SEQ ID NO:3, the mouse calponin 2 comprising the sequence set forth in SEQ ID NO:21, and the pig h2-calponin comprising the sequence set forth in SEQ ID NO:5. Although the human h2-calponin sequence of SEQ ID NO:1 (and the encoding sequence of SEQ ID NO:2) as well as the pig h2-calponin sequence of SEQ ID NO:5 (and the encoding sequence of SEQ ID NO:6) are incomplete in that each lacks residues at the C-terminus of the protein (SEQ ID NO:1 and SEQ ID NO:5) or at the 3' end of the polynucleotide (SEQ ID NO:2 and SEQ ID NO:6), one of skill would readily be able to identify the corresponding full-length polynucleotide and/or amino acid sequences from database queries or from experiments identifying physical molecules, and these full-length molecules are embraced by the method according to the invention.

Variants of these mammalian h2-calponins are also contemplated for use in the assays, provided they are encoded by polynucleotides comprising a sequence that is at least 80%, 85%, 90%, 95%, 99%, or 99.9% identical to a sequence set forth in any one of SEQ ID NOS: 2, 4, and 6. Variants of the mammalian h2-calponins also include proteins having amino acid sequences that are at least 80%, 85%, 90%, 95%, 99%, or 99.9% identical to an amino acid sequence set forth in any one of SEQ ID NOS: 1, 3, and 5. The protein variants suitable for use in the screening assays are expected to exhibit insertions, deletions and substitutions of 1, 2, 3, 4, 5, 6, 7, 8, 9, or 10 preferably contiguous amino acids.

H2-calponins suitable for use in the screening methods also may be derivatives of a mammalian h2-calponin, including h2-calponins exhibiting any known form of post-translational processing, e.g., glycosylation. More generally, the h2-calponins suitable for use in the screening methods include known mammalian h2-calponins and variants and derivatives thereof, provided that the proteins retain an h2-calponin-specific activity, such as affecting the migration and/or proliferation of a cell as identified herein, and provided that the structure of such protein is identifiable as belonging to the h2-calponins, rather than the acidic calponins (calponin 3, CNN3) or the basic calponins (h1 calponin, calponin 1, CNN1). Sequence alignments of acidic, basic and neutral (H2) calponins are within the skill in the art and, using any known algorithm, a sequence may be assigned to one of the aforementioned calponin types, or to none at all. The screening methods of the invention comprise use of proteins that are members of the family of h2-calponins.

Calponins other than the h2-calponin group, i.e., acidic and basic calponins, help to define the h2-calponin group. Towards that end, exemplary acidic calponins include human calponin 3 of SEQ ID NO:24 (encoded, e.g., by SEQ ID NO:23), cow calponin 3 of SEQ ID NO:26 (encoded, e.g., by SEQ ID NO:25), mouse calponin 3 of SEQ ID NO:28 (encoded, e.g., by SEQ ID NO:27), rat calponin 3 of SEQ ID NO:30 (encoded, e.g., by SEQ ID NO:29). Exemplary basic calponins are the h1 calponins or calponin 1 proteins, such as the human calponin 1 (SEQ ID NO:7, encoded, e.g., by SEQ ID NO:8), the mouse calponin 1 of SEQ ID NO:9 (encoded, e.g., by SEQ ID NO:10), the mouse h1 calponin of SEQ ID NO:13 (encoded, e.g., by SEQ ID NO:14), the pig calponin 1 of SEQ ID NO:11 (encoded, e.g., by SEQ ID NO:12), and the pig h1-calponin of SEQ ID NO:15 (encoded, e.g., by SEQ ID NO:16), A related aspect of the invention is drawn to a method of screening for a modulator of h2-calponin comprising: (a) contacting a cell comprising an expressible coding region for h2-calponin with a candidate modulator; (b) determining the activity of the h2-calponin in the presence and absence of the candidate modulator; and (c) identifying the candidate modulator as a modulator of h2-calponin if the activity of h2-calponin differs in the presence and absence of the candidate modulator. In some embodiments, the activity is determined by measuring the expression level of the h2-calponin. Also in some embodiments, the h2-calponin is intracellular h2-calponin. A cell comprising h2-calponin and suitable for this aspect of the invention is a cell selected from the group consisting of an epidermal keratinocyte, a lung alveolar cell, a cornea epithelial cell, an endothelial cell, a kidney podocyte, an osteoblast, a fibroblast, a monocyte, a macrophage, a neutrophil, a myoblast, an embryonic stem cell and a cancer cell. An exemplary cell for use in this aspect of the invention is a cell selected from the group consisting of a cornea epithelial cell, an endothelial cell, a kidney podocyte, an osteoblast, a monocyte, a macrophage, a neutrophil, a myoblast and an embryonic stem cell. In some embodiments, the modulator inhibits the activity of h2-calponin. In some embodiments, the modulator increases the activity of h2-calponin. An exemplary modulator according to this aspect of the invention is an expression regulator responsive to cytoskeleton tension.

Other features and advantages of the invention will be better understood by reference to the brief description of the drawing and the detailed description of the invention that follow.

DETAILED DESCRIPTION

Figure 1:
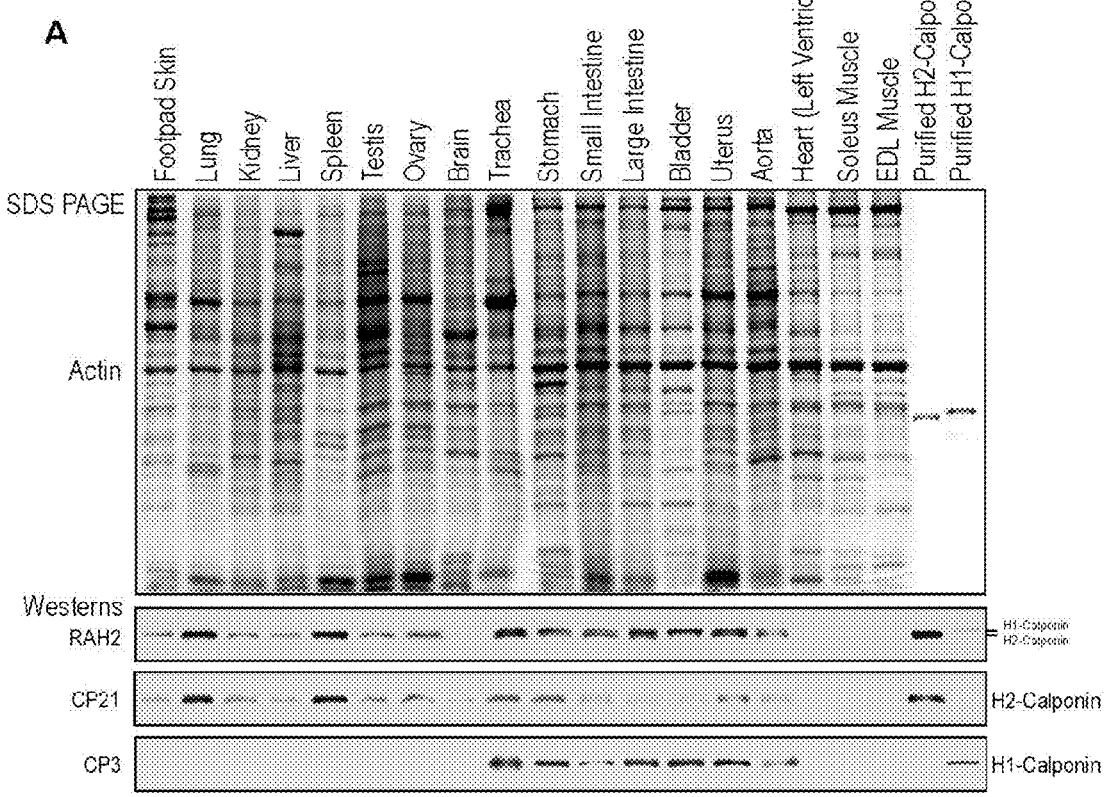
FIG. 1. Tissues and cells expressing h2-calponin. (A) SDS-PAGE gel and Western blot of various tissues and organs showing protein expression with actin identified on the protein gel. Western blot showing H1-calponin and H2-calponin expression in the various tissues using anti-calponin antibodies, i.e., RAH2, CP21 and CP3. (B) Western blot of total protein extracts from cultured cells of various tissues. Western blot was normalized to actin expression and probed with RAH2.
Figure 1:
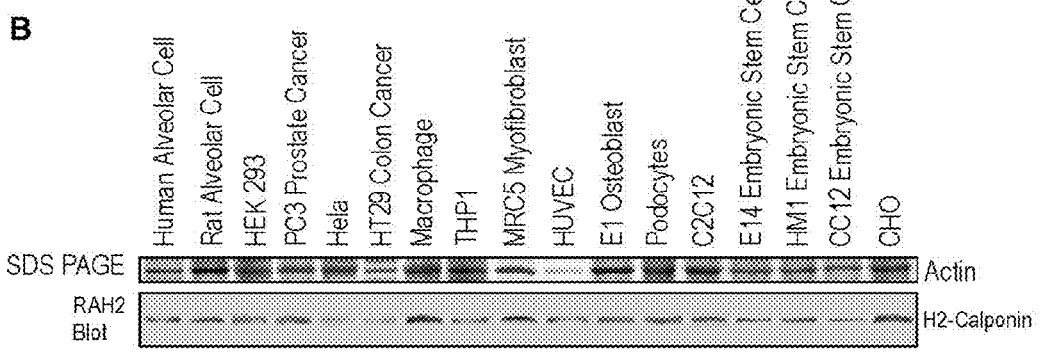

Calponin is an actin filament-associated regulatory protein. H2-calponin is a member of the calponin family. H2-calponin is found in smooth muscle and in a number of non-muscle cells such as epidermal keratinocytes, lung alveolar cells, cornea epithelial cells, endothelial cells, kidney podocytes, osteoblasts, fibroblasts, monocytes/macrophages, neutrophils, myoblasts, embryonic stem cells, and a number of cancer cells.

Transfective (unregulated) over-expression of h2-calponin inhibited cell proliferation. Unregulated over-expression also inhibited cell migration. In the h2-calponin gene knock-out/knock-down mice disclosed herein, it has been shown that the diminished expression and function of h2-calponin also alters cell migration and cell proliferation. Therefore, modulating h2-calponin expression (e.g., by transfective over-expression or RNAi inhibition) and function (e.g., PKC phosphorylation) is expected to provide control over the proliferation and migration of the above cell types, thereby providing for methods to prevent, ameliorate or treat diseases and/or disorders associated with aberrant migration or proliferation of the above cell type(s).

Data disclosed herein establishes that h2-calponin is regulated by mechanical tension at the level of gene expression, as well as at the level of proteolytic degradation. Therefore, controlling h2-calponin levels and activities is expected to provide methods for altering mechanical tension-related processes, such as skin wound healing (e.g., to decrease h2-calponin in epidermal keratinocytes to promote proliferation and migration and to increase expression in fibroblasts and macrophages to limit scar formation) and lung preservation during prolonged deflation. Lung deflation normally results in rapid degradation of h2-calponin, which reduces the stability of the actin cytoskeleton. Stabilization of h2-calponin in the deflated lung is expected to provide protection during open chest surgery, lung transplantation and the treatment of pneumothorax.

Apparent from the disclosure provided herein is that the expression and function of h2-calponin in multiple tissues and cell types provides a broad basis for developing therapeutic approaches with h2-calponin (the expressed protein or the encoding nucleic acid) as the molecular target. Therapeutic applications include, but are not limited to: 1) inhibiting cell proliferation and migration in the treatment of cancer growth (directly on cancer cells or indirectly through inhibiting capillary growth), tumor metastasis, myeloid leukemia, atherosclerosis, and autoimmune lesions such as rheumatoid arthritis; 2) enhancing cell proliferation and migration in the treatment of myocardial ischemia, bone loss, and improving wound healing and tissue regeneration; and 3) Stabilizing cellular structure in the treatment of pneumothorax, preservation of lung alveolar function during open chest surgery and lung transplantation, and prevention of pressure-induced renal unit losses. All of these problems currently lack effective solutions and are awaiting improved treatments.

The data disclosed herein establish that, in one exemplary context, h2-calponin activity levels had a potent effect on endothelial cell motility. The experiments were performed using primary human umbilical vein endothelial cells and immortalized human microvascular endothelial cells. Together with control cells, in vitro wound healing experiments showed an inverse correlation between the rate of cell migration and the level of h2-calponin expression. Transfective expression of h2-calponin inhibited the healing process. Also, cell retraction was stimulated and cyclic stretching was applied to investigate the regulation of h2-calponin expression and degradation in vascular endothelial cells by mechanical tension as well as to determine the effects on cell motility. The availability of tissues and vascular endothelial cells isolated from h2-calponin gene knock-out/knock-down mice is establishes that over-expression or under-expression of h2-calponin has a deleterious effect on motility and proliferation of a variety of cells, including, e.g., endothelial cells.

EXAMPLE 1

H2-calponin Expression Profile

The expression profile of h2-calponin was determined using total protein extracts from representative mouse tissues. Extracts were analyzed by Western blots using an anti-h2-calponin polyclonal antibody RAH2 (Nigam et al., J. Muscle Res. Cell Motil. 19:695-703, 1998), an anti-h2-calponin monoclonal antibody (mAb) CP21 (Jin et al., Protein Expr Purif. 31:231-239, 2003), and an anti-h1-calponin mAb CP3 (Jin et al., Biochem. Cell Biol. 74:187-196, 1996). The blots showed that h2-calponin was expressed in smooth muscle and several non-muscle tissues, with the highest levels in lung and spleen endothelial tissue (FIG. 1A). In addition, total protein extracts from cultured cells of different tissue origins were analyzed by Western blots using the RAH2 antibody. The blots were normalized by actin levels and showed that h2-calponin was expressed in epithelial cells, endothelial cells, fibroblasts, myoblasts, osteoblasts, kidney podocytes, myeloid cells/macrophages, metastatic prostate cancer cells, and embryonic stem cells (FIG. 1B). CP3 monoclonal antibody Western blots showed no expression of h1-calponin in these cells (Id.).

Figure 7:
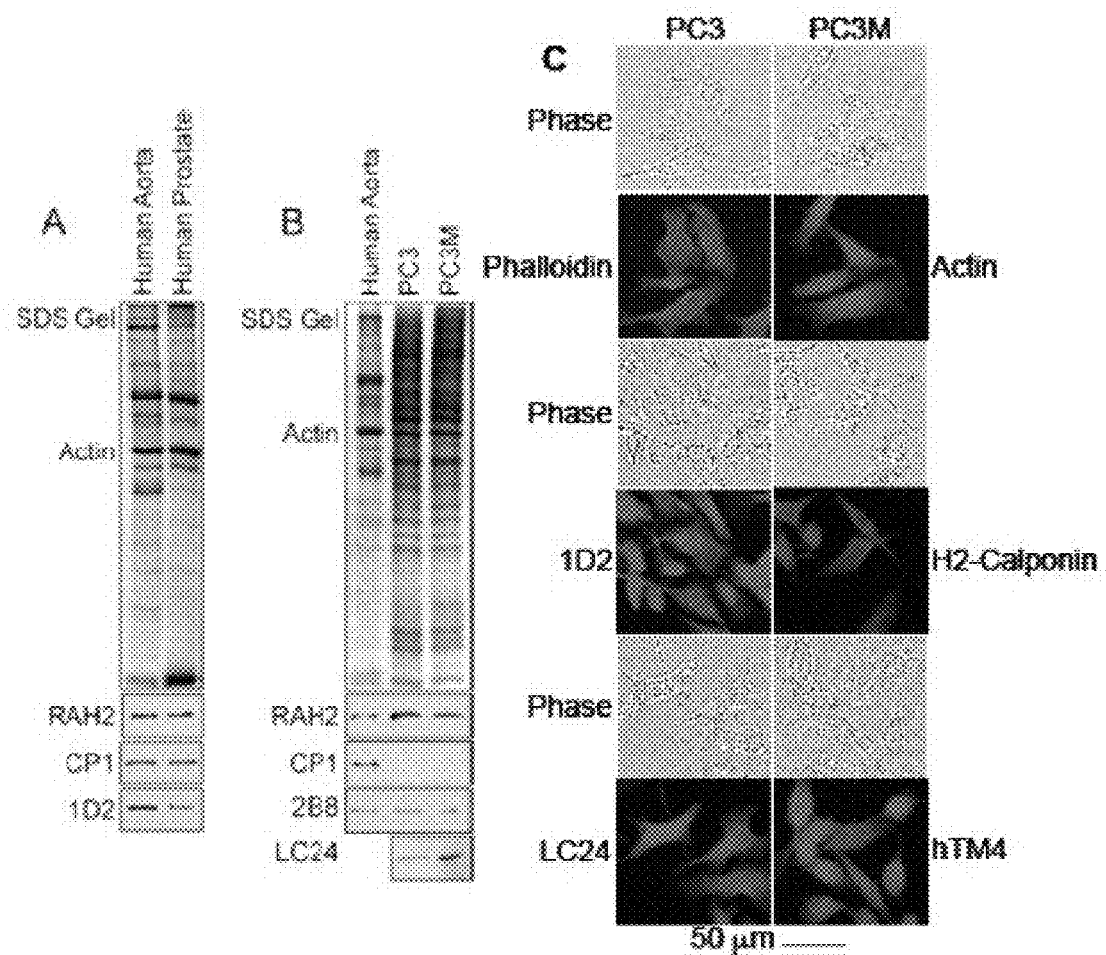
FIG. 7. Western blot analyses of h2-calponin expression in human aorta cells, PC3 cells and PC3-M cells.

In related experiments, significant expression of h2-calponin was detected in human prostate cells by Western blot analysis (FIG. 7A), again using the anti-h2-calponin polyclonal antibody RAH2. In addition, significant expression of h2-calponin was found in a prostate cancer cell line PC3 and in its metastasis derivative cell line, PC3-M (FIG. 7B). By comparison, H1-calponin is expressed in prostate cells but not in PC3 or PC3-M cells. The control in both experiments were human aorta cells. Also apparent in FIG. 7B is that the expression of low molecular weight tropomyosin hTM4 was increased in PC3-M cells. In FIG. 7C, results of immunofluorescence microscopy and phase-contrast microscopy studies of h2-calponin and actin in each of PC3 and PC3-M cells are shown. The photomicrographs show that h2-calponin is associated with the actin cytoskeleton in both PC3 and PC3-M cells.

Figure 8:
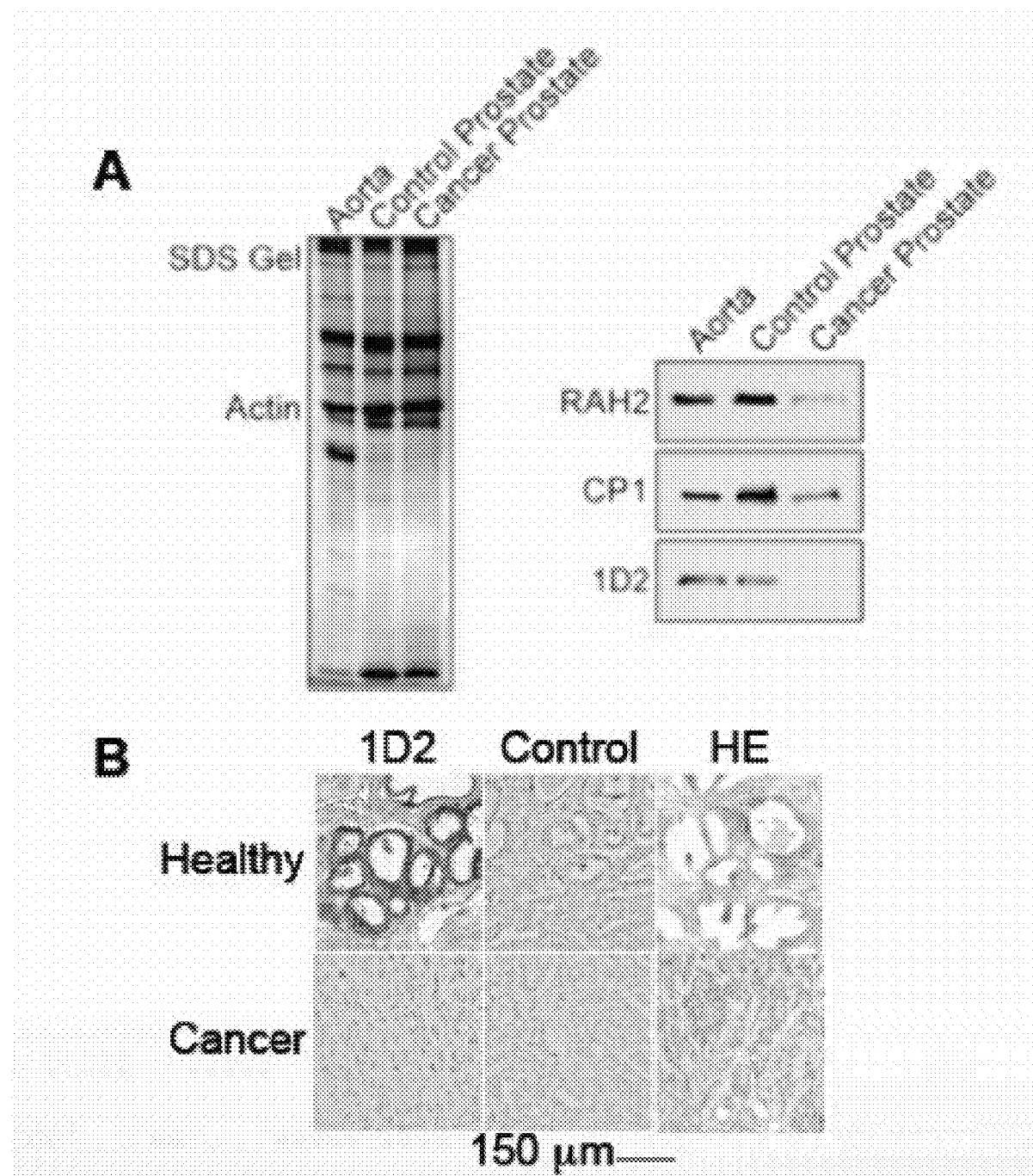
FIG. 8. Western blot and immunohistochemical micrographs of h2-calponin expression in human aorta cells, healthy prostate cells and prostate cancer cells.

An additional study demonstrated that h2-calponin is expressed at lower levels in prostate cancer cells than in healthy prostate cells. Western blots of human aorta cells (control), healthy prostate cells, and prostate cancer cells are shown in FIG. 8. The Western blot in FIG. 8A using the RAH2 anti-h2-calponin antibody showed a clear reduction in h2-calponin expression in the prostate cancer cells relative to healthy prostate cells or human aorta cells. FIG. 7B shows the results of immunohistochemical analyses of these cells, again demonstrating the diminished expression of h2-calponin in prostate cancer cells relative to healthy prostate cells.

The results establish that h2-calponin expression is relatively widespread, and is not confined to smooth muscle cells. As one example, h2-calponin is expressed at significant levels in prostate cells and is expressed in PC3 and PC3-M cells, although at lower levels than in healthy prostate cells. Further, the data show that the expressed h2-calponin is associated with the actin cytoskeleton.

EXAMPLE 2

Cell Cycle Regulation of H2-calponin

To examine the expression of h2-calponin as a function of the cell cycle, a synchronized population of HT29 colon carcinoma cells (von Kleist et al., J Natl Cancer Inst. 55:555-60, 1975) was prepared by collecting newly divided cells within one hour after being "shaken off" from monolayer cultures. The synchronized cells were then sampled at various time points and total protein extracts were prepared using conventional techniques. Lysates were examined by SDS-gel and Western blot for the expression of h2-calponin.

Figure 2:
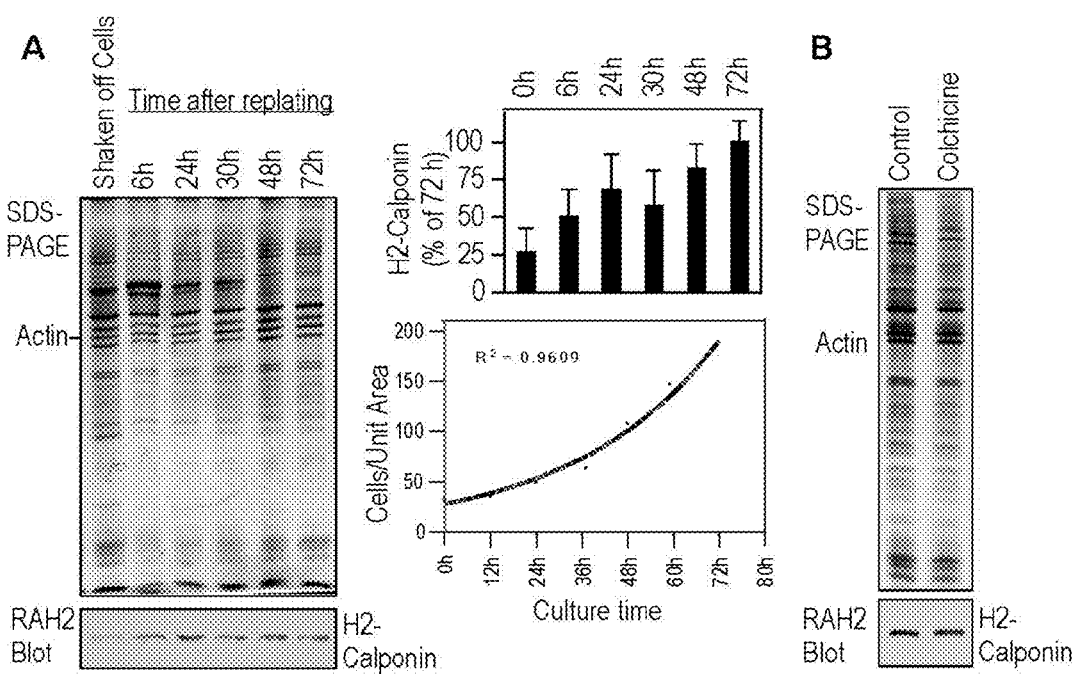
FIG. 2. Regulation of h2-calponin during the cell cycle. (A) Western blot (RAH2 probe) of synchronized HT29 colon carcinoma cells at various stages of the cell cycle from newly divided (0 hours) to confluency (72 hours). Bar diagram reflects densitometric scan of the Western blot and the growth curve plots cells per unit area as a function of time. (B) Western blot (RAH2 probe) of protein extracts from 30-hour colchicine-treated cells stopping cell cycle prior to M phase.

The level of h2-calponin was lower in the newly divided cells than in confluent monolayer control cells, as shown in FIG. 2A (see 72-hour sample; *$P<0.05$). Western blot densitometry (FIG. 2A, upper central panel) revealed a second dip of h2-calponin level at 30 hours of culture (less obvious due to the reduced degree of cell cycle synchronization), approximately after the completion of one cell cycle, as indicated by the cell growth curve (FIG. 2A, lower central panel). Arrest of the cell cycle by a 30-hour colchicine treatment stopped all cells before the M phase and revealed that the level of h2-calponin remained high (FIG. 2B). The data indicate that in addition to being expressed in a wide variety of tissues (see Example 1), h2-calponin is expressed at higher levels later in the cell cycle.

EXAMPLE 3

Lower H2-calponin Levels in PC3-M Cells Relative to PC3 Cells

The origin, characteristics, and culture conditions for the PC3 and PC3-M prostate cancer cell lines have previously been described (Liu et al., Prostate Cancer Prostatic Dis, 4:81-91, 2001, incorporated herein by reference). Cultures samples were lysed and total protein extracts were obtained using convention techniques.

Figure 3:
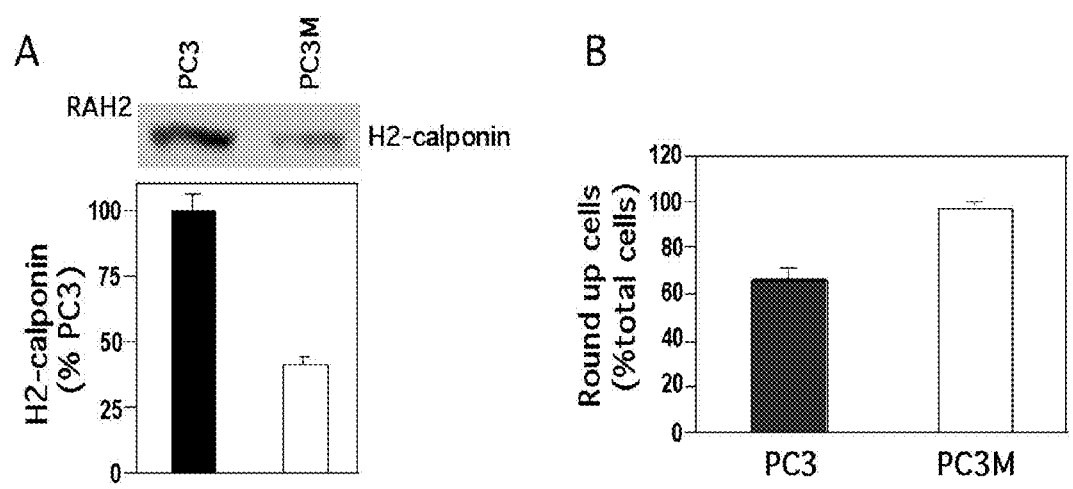
FIG. 3. Lower h2-calponin levels in PC3-M relative to PC3 prostate cancer cells corresponds to a more dynamic cytoskeleton. (A) Western blot (RAH2 probe) of protein extracts from PC3-M and PC3 cells and densitometric scan (bar diagram) normalized to actin levels. (B) Bar diagram showing rounding-up of PC3-M and PC3 cells during trypsinization. Rounded-up cells measured as a percent of total cells.
Figure 9:
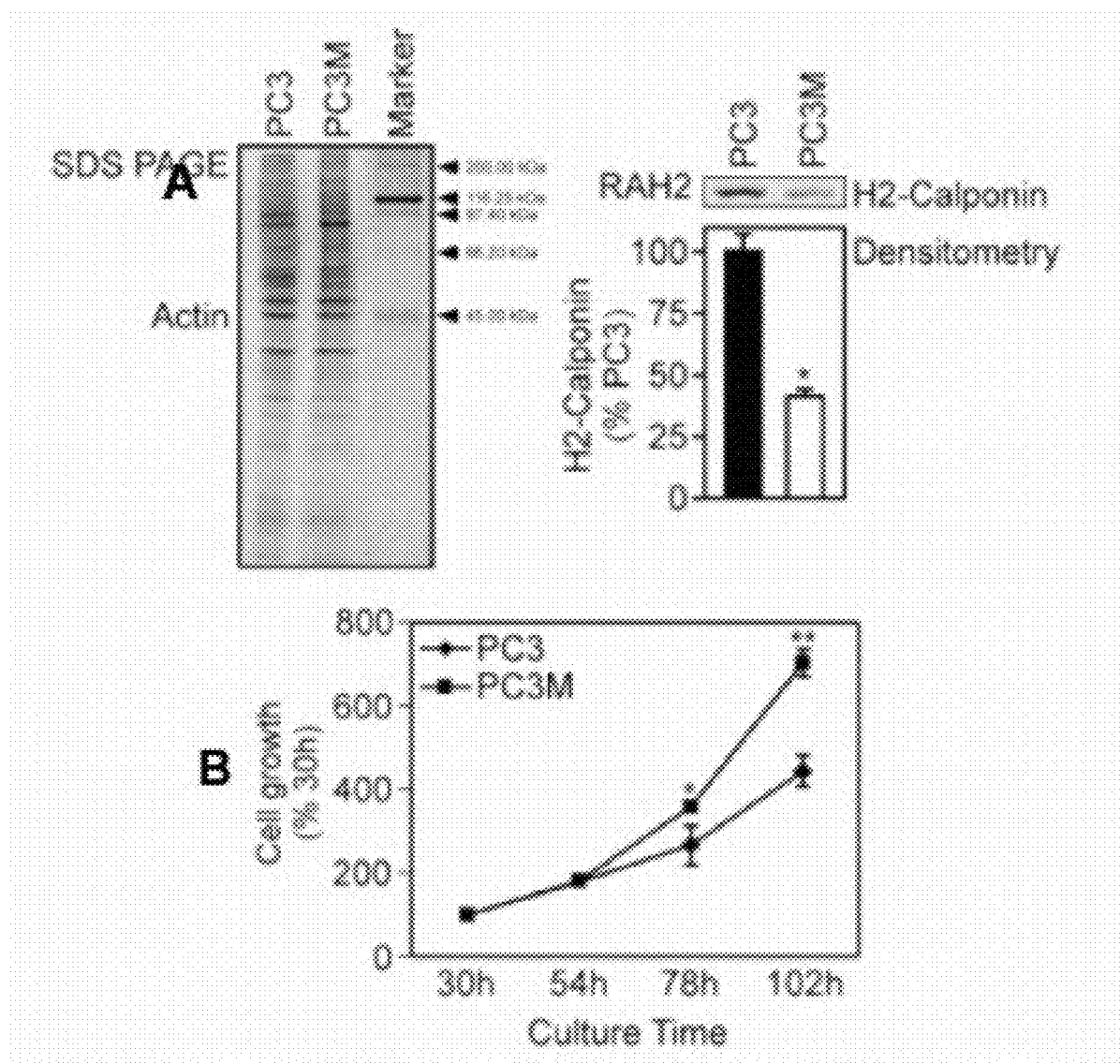
FIG. 9. Western blot, densitometric scan, and cell growth plot of h2-calponin in PC3 and PC3-M cells.
Figure 17:
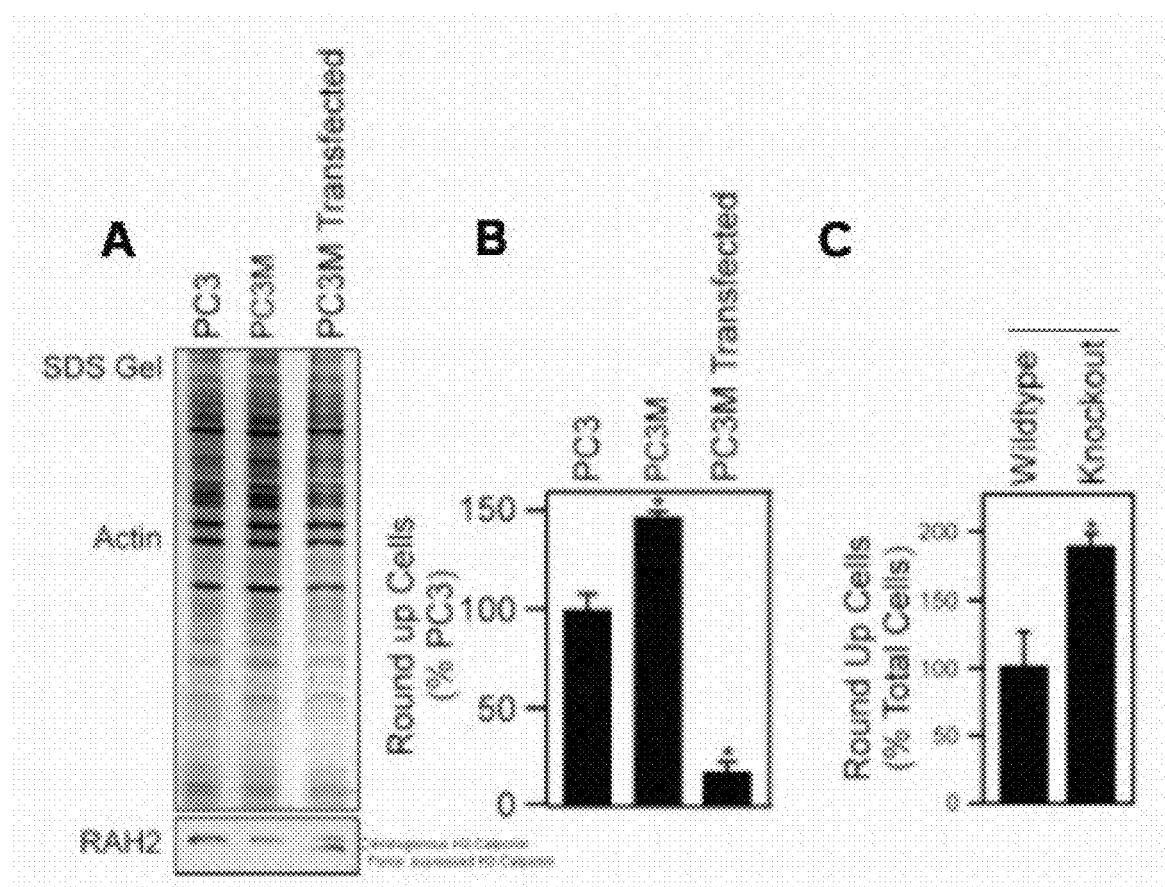
FIG. 17. Western blot and histograms of the percent of cell round-up after 10 minutes trypsinization of monolayer cultures of PC3, PC3-M and h2-calponin-transfected PC3-M cells.

Lysates were fractionated on SDS-PAGE gels and the fractionated proteins transferred to membranes for Western blot analyses. Western blots and densitometry analyses were normalized by the level of actin and showed a significantly lower level of h2-calponin in PC3-M cells compared to the h2-calponin level in its parental cell line, PC3 (FIG. 3A, *$P<0.01$; FIG. 9A, *$P<0.001$). (PC3-M is a liver-metastasized derivative of PC3.) PC3-M cells showed a faster rounding-up than that of PC3 cells during trypsinization under identical conditions (FIG. 3B, *$P<0.01$). Another study confirmed the relative rates of cell round-up. Western blots were prepared from lysates of PC3, PC3-M and transfected PC3-M cells (FIGS. 17A and B) and from lysates of wild-type and h2-calponin knockout fibroblast cells (FIG. 17C) to assess the effect of differing h2-calponin expression levels on cell round-up. Monolayer cell cultures were allowed to develop and then these cultures were treated with trypsin for 10 minutes using a conventional protocol. The results (percent of cells rounded up after 10 minutes trypsinization) shown in FIGS. 17A and B demonstrate that h2-calponin is negatively correlated with rate of cell round-up. FIG. 17C compares wild-type and h2-calponin knockout fibroblast cells under the same conditions and yields data confirming that h2-calponin expression level is negatively correlated with rate of cell round-up.

Figure 10:
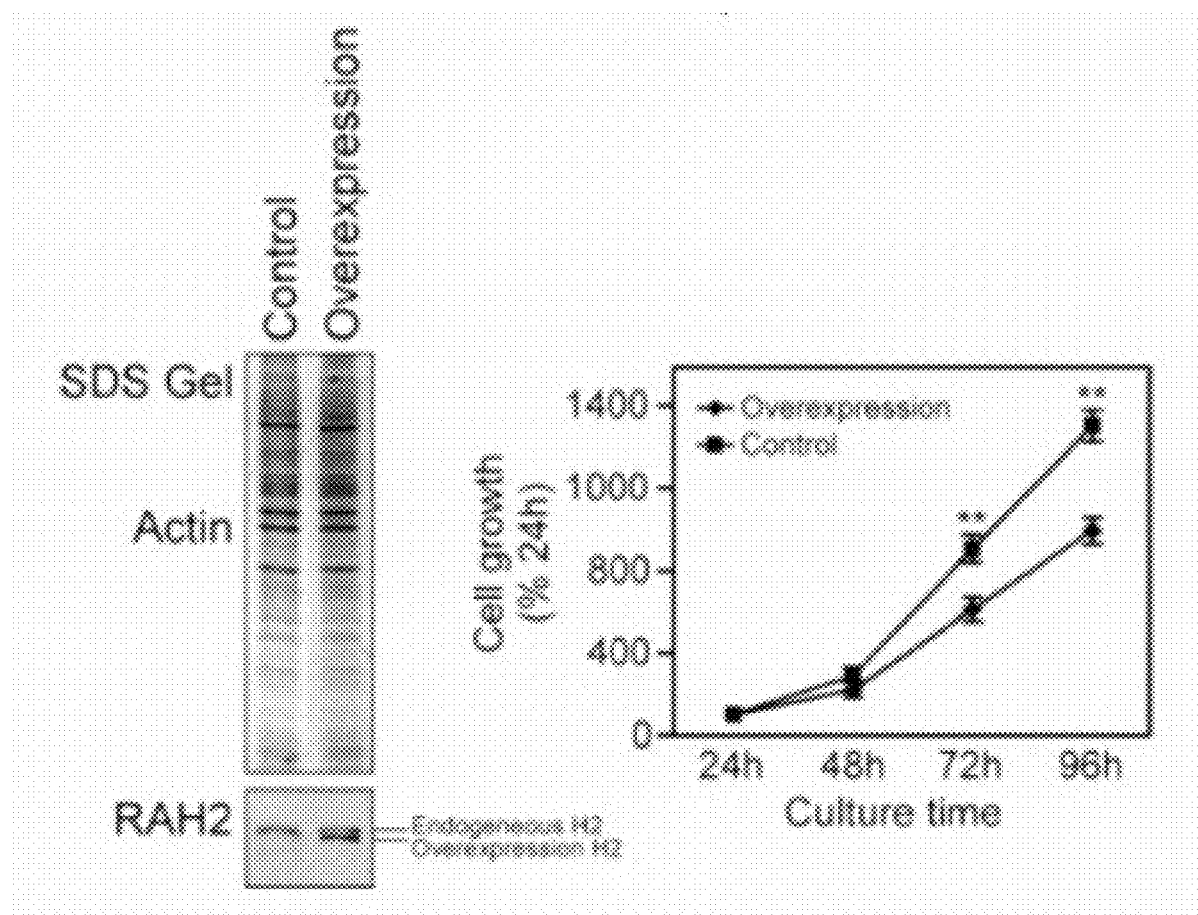
FIG. 10. Western blot and cell growth plot of transfective h2-calponin expression in PC3-M cells. Control is transfected PC3-M cells resistant to G418 but not expressing h2-calponin.

In another comparative experiment, the rates of proliferation of PC3 and PC3-M cells were determined by crystal violet staining. Cells were grown in 96-well plates and conventional staining techniques were used. The results, shown in FIG. 9B, demonstrate that PC3-M cells grow significantly faster than PC3 cells (*P<0.005; **P<0.001). Transfective expression of mouse h2-calponin in PC3-M cells also revealed that h2-calponin expression effectively decreased the proliferation rate of PC3-M cells (FIG. 10). In this experiment, transfected PC3-M cells transfected with the mouse h2-calponin construct that were resistant to G418 but that did not express h2-calponin served as the control.

Figure 14:
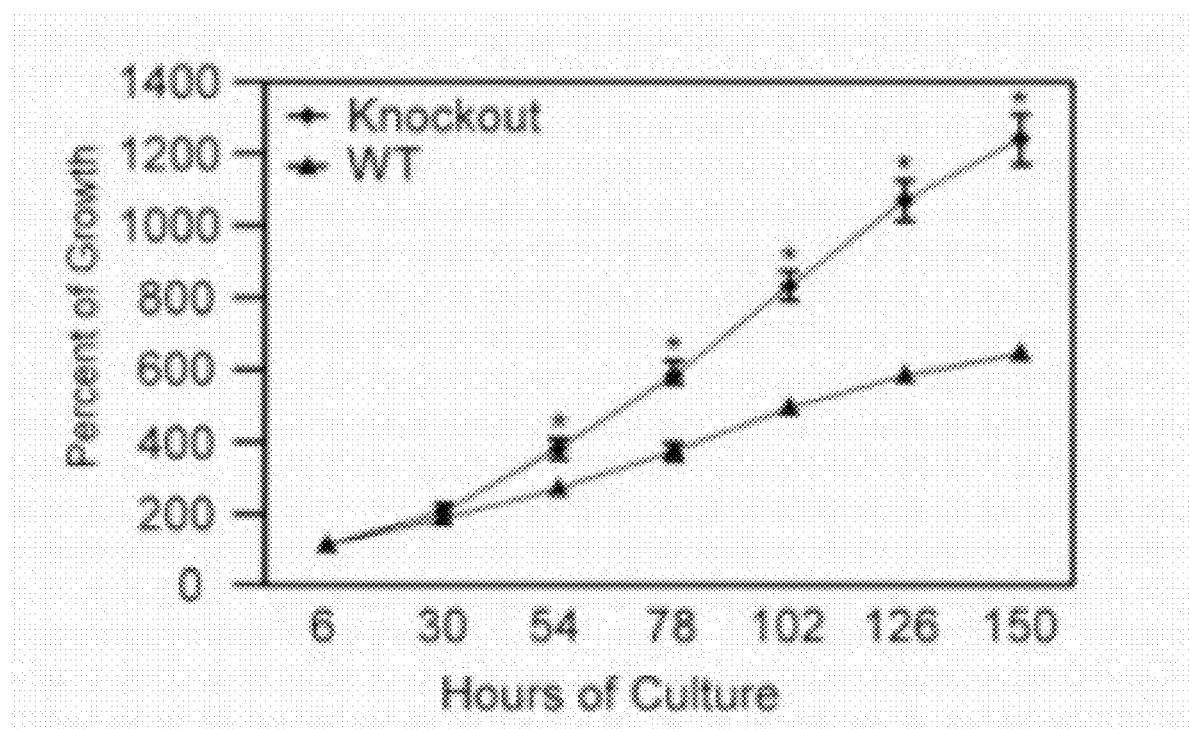
FIG. 14. Graph of percent growth as a function of culture time for wild-type and h2-calponin knockout primary fibroblast cells.

The relative proliferation rates of primary fibroblast culture cells were also determined and those rates correlated to the expression levels of h2-calponin. Primary culture were established using fibroblasts isolated from the leg muscles of wild-type and h2-calponin knockout mice. Cell proliferation was assessed using conventional crystal violet staining. The results (FIG. 14) showed significantly higher rates of cell proliferation for the h2-calponin knockout cells than for wild-type cells (*P<0.001).

The experiments establish that prostate cancer cells express h2-calponin at lower rates than healthy prostate cells, with PC3-M expressing at a lower rate than PC3 cells as well. Further, the experiments showed that h2-calponin expression decreased cell proliferation rate. These results established a role for h2-calponin in regulating cell proliferation.

EXAMPLE 4

Faster Migration of PC3-M Relative to PC3 Cells

Figure 4:
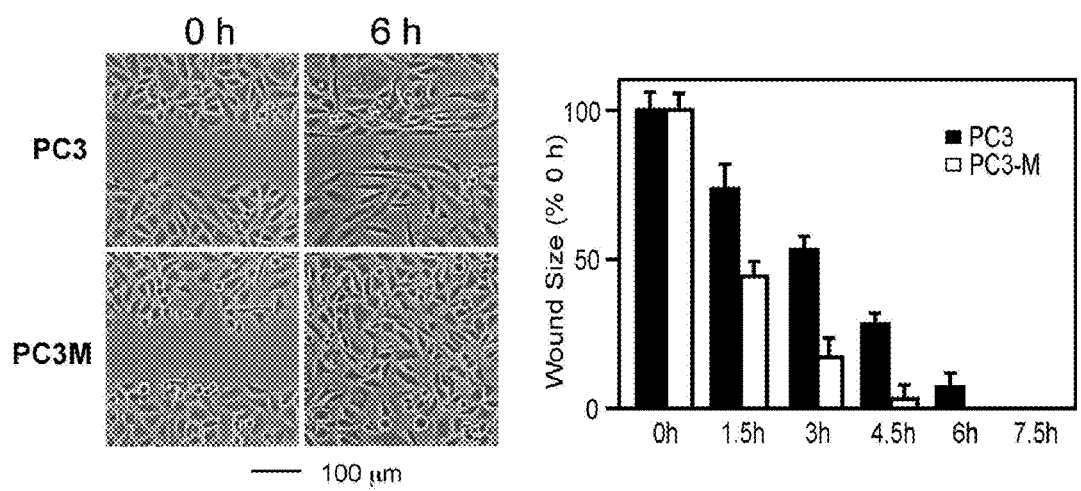
FIG. 4. Faster migration of PC3-M relative to PC3 cells in a wound healing assay. Phase contrast micrographs of wounded monolayer cultures of PC3-M and PC3. Indicated times are post-wounding with a modified thin gel loading pipette tip. Bar diagram indicates relative wound size measured as the ratio of wound width at time=n to wound width at time=0 multiplied by 100 to reflect percent wound size. Open bars: PC3-M; closed bars: PC3.
Figure 11:
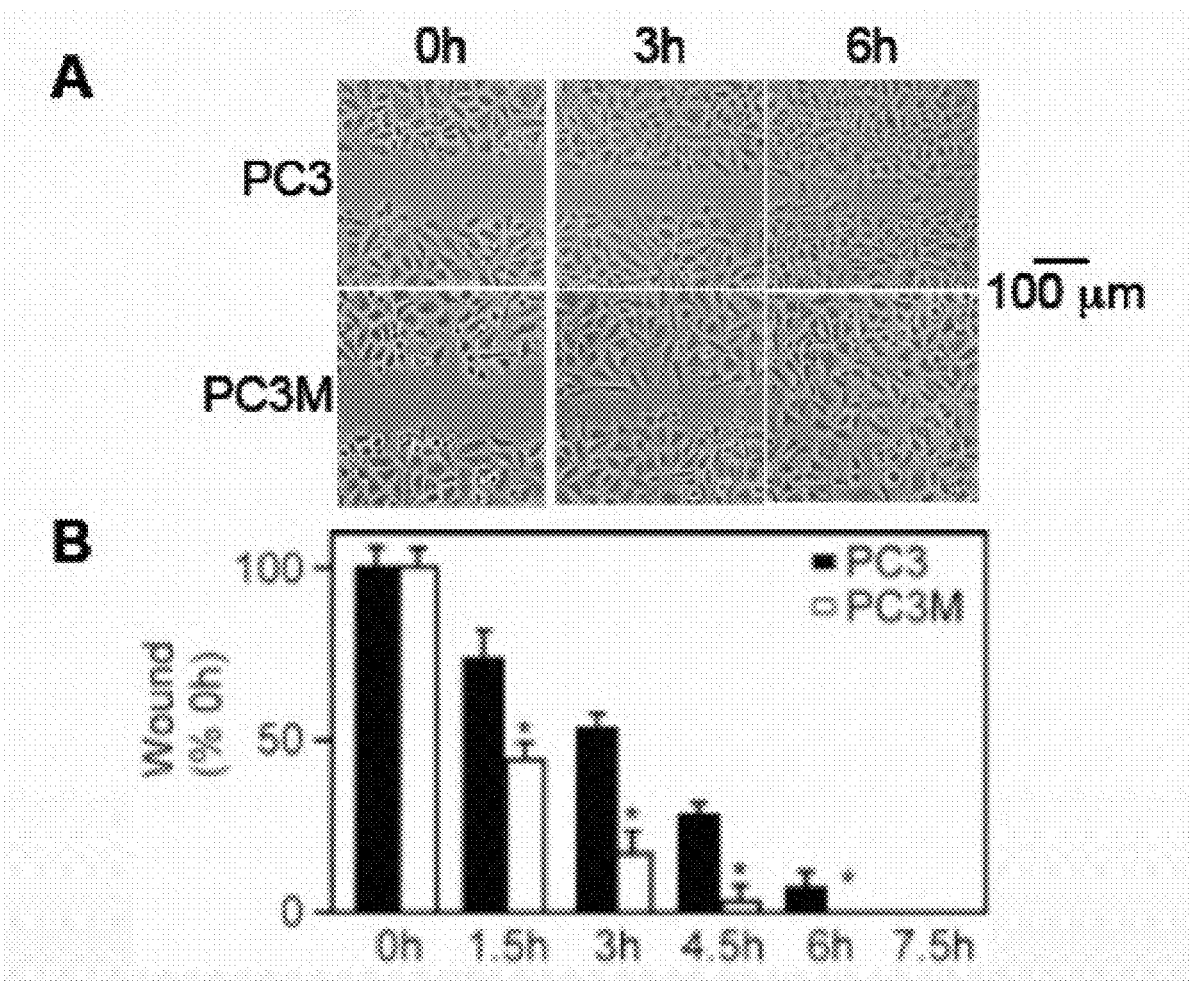
FIG. 11. Phase-contrast micrographs and histogram showing scratch wound assay results.
Figure 12:
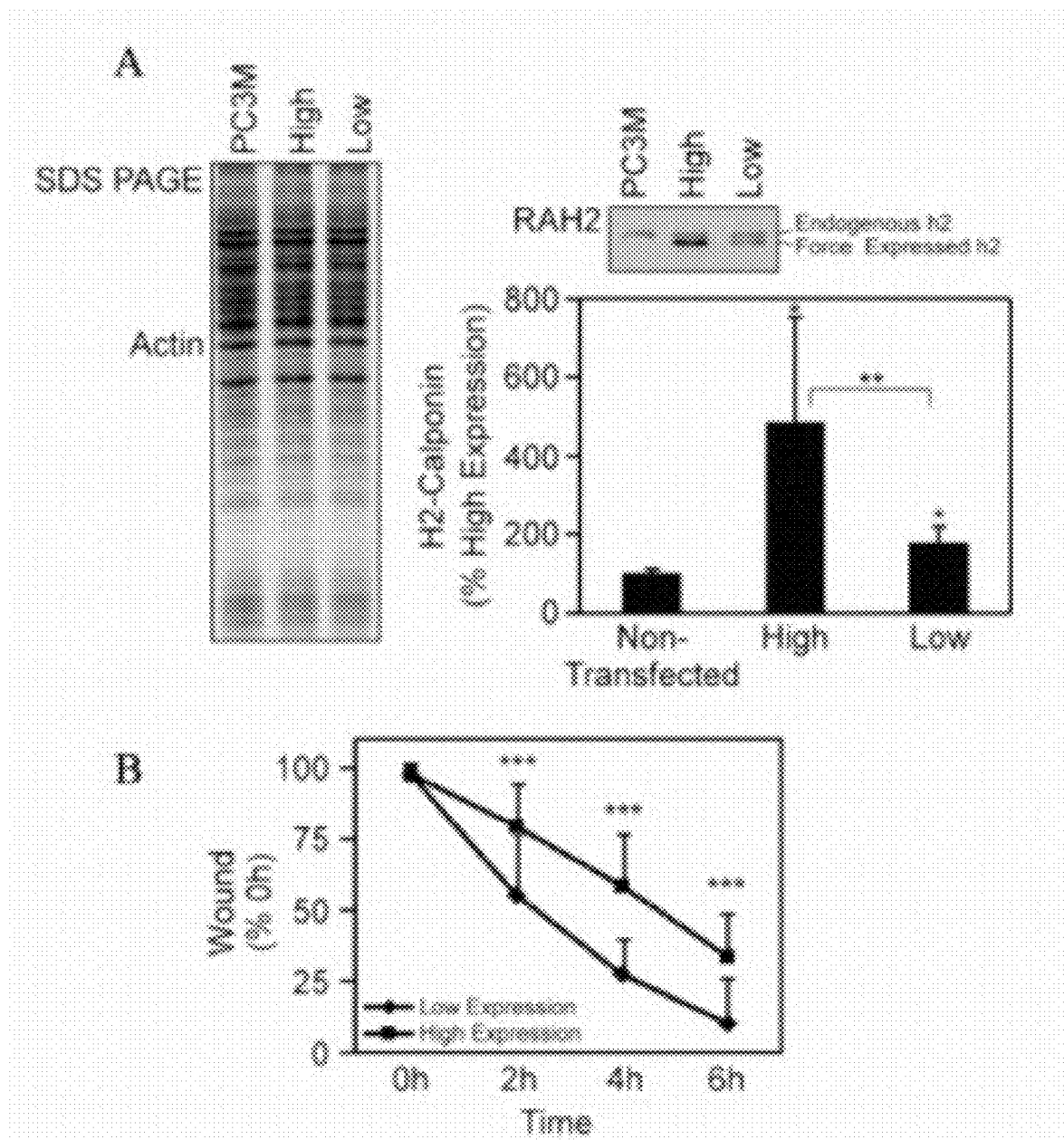
FIG. 12. Western blot and scratch wound assay results of PC3-M cells transfectively expressing h2-calponin.

Cell migration was assessed by measuring the time for a monolayer culture to recover from a microscopically visible wounding. PC3 and PC3-M cells were cultured in RPMI containing 10% FBS to reach confluence. Monolayer cells were wounded with a modified thin gel loading pipette tip. To monitor the wound healing process, phase-contrast micrographs were taken every 1.5 hours. The width of the wound was measured to quantify cell migration rates during wound healing. The results shown in FIG. 4 revealed faster migration for PC3-M cells than for PC3 cells (° P<0.01). A similar experiment comparing the migration rate and time for wound closure of PC3 and PC3-M cells yielded the results shown in FIG. 11. Shown in FIG. 11A are phase-contrast micrographs of either PC3 or PC3-M cells wounded by scratching, as described above. These results, like the results shown in FIG. 4, demonstrate that PC3-M cells began migrating before PC3 cells and PC3-M cells closed the scratch wound quicker than PC3 cells. These results were confirmed by an experiment in which PC3-M cells transfectively expressed mouse h2-calponin. As shown in FIG. 12, the higher the level of expression of h2-calponin, the longer the time to close the wound inflicted using the scratch wound assay described above. The results showed that cells containing higher levels of h2-calponin migrated slower (*P<0.05; P<0.005; *P<0.001), establishing a role for h2-calponin in inhibiting prostate cancer cell motility.

Figure 15:
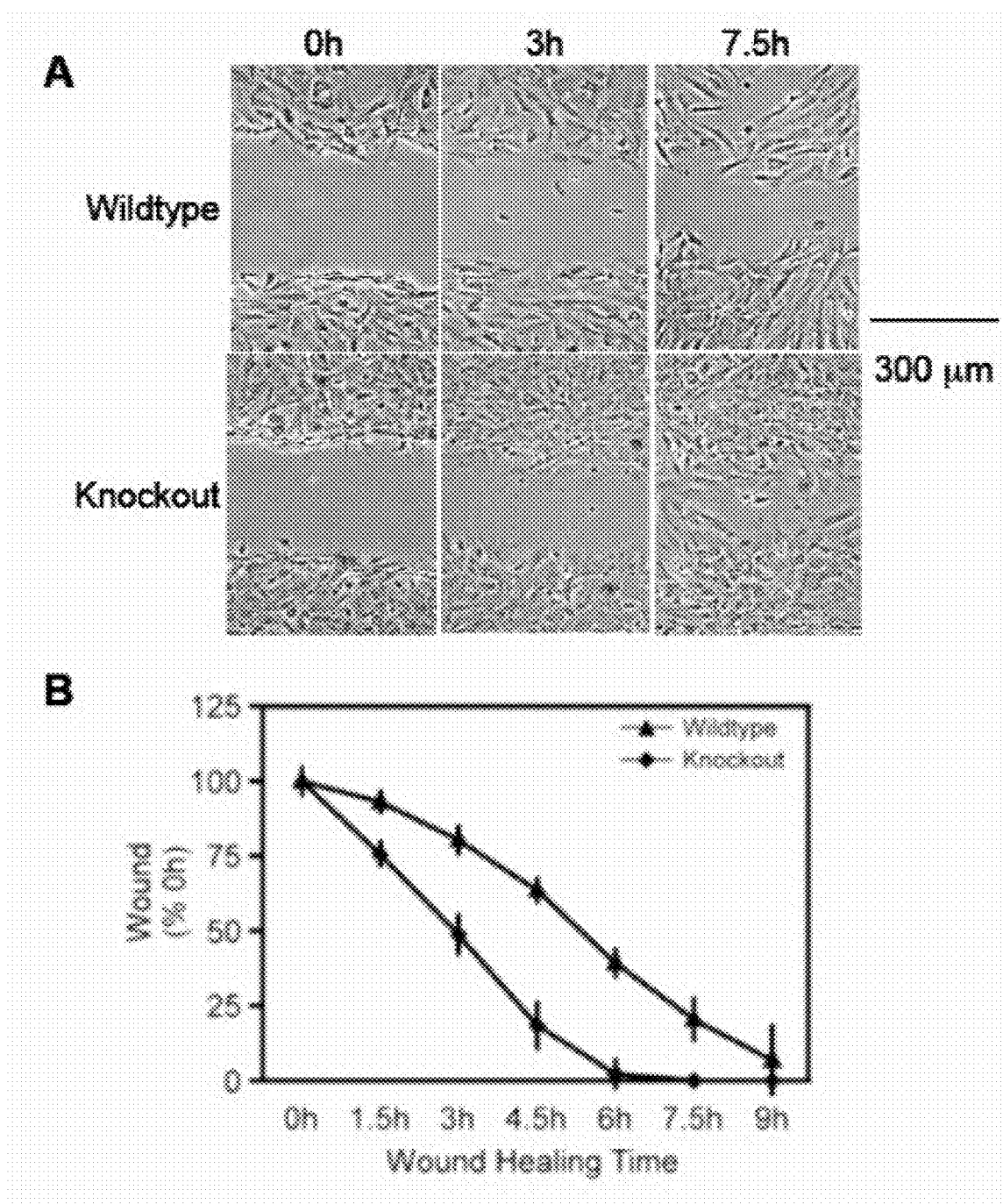
FIG. 15. Phase-contrast micrographs and plot of percent wound healing as a function of healing time for wild-type and h2-calponin knockout primary fibroblast cells.

Wild-type and h2-calponin knockout fibroblast cells (leg muscle) were also subjected to the scratch wound healing assay. Micrographs revealing the results of the scratch wound healing assay are shown in FIG. 15A. These results showed that, following scratch wounding, h2-calponin knockout fibroblasts began migrating earlier than their wild-type counterpart cells. A plot of percent wound healing as a function of wound healing time is presented in FIG. 15B, and confirms that the h2-calponin knockout cells healed sooner than the wild-type cells (*P<0.001).

EXAMPLE 5

H2-calponin Knockdown Cells Exhibit Lowered Resistance to Stretching Injury

Figure 5:
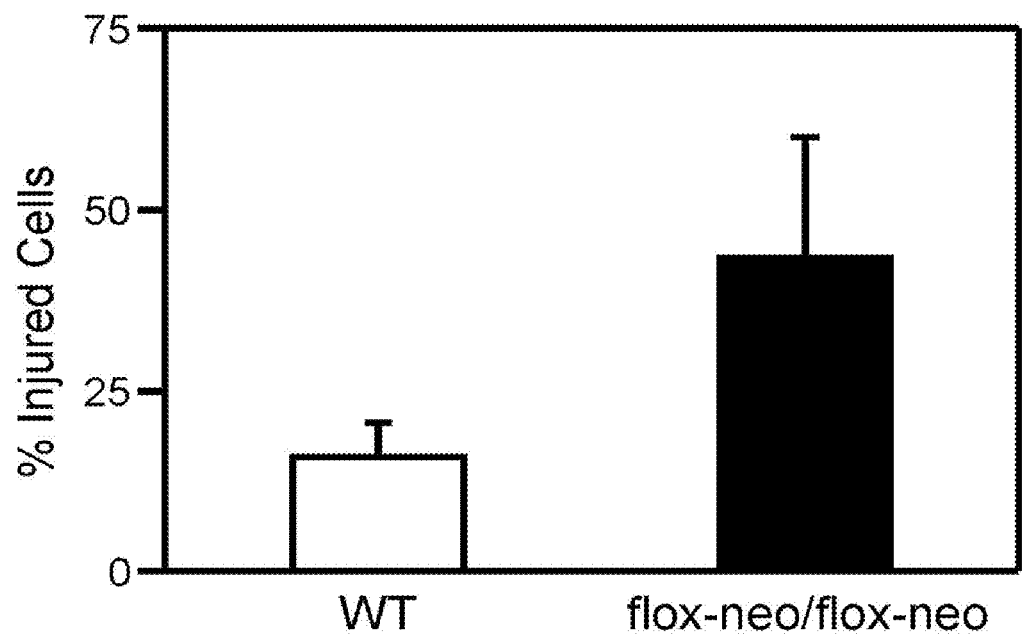
FIG. 5. Lower resistance of h2-calponin knockdown cells to stretching injury. Bar diagram showing percent cell injury of fibroblast cultures of wild-type mouse (open bar) and homozygous Cnn2-flox-neo mouse (closed bar) in a cell-stretch assay.
Figure 13:
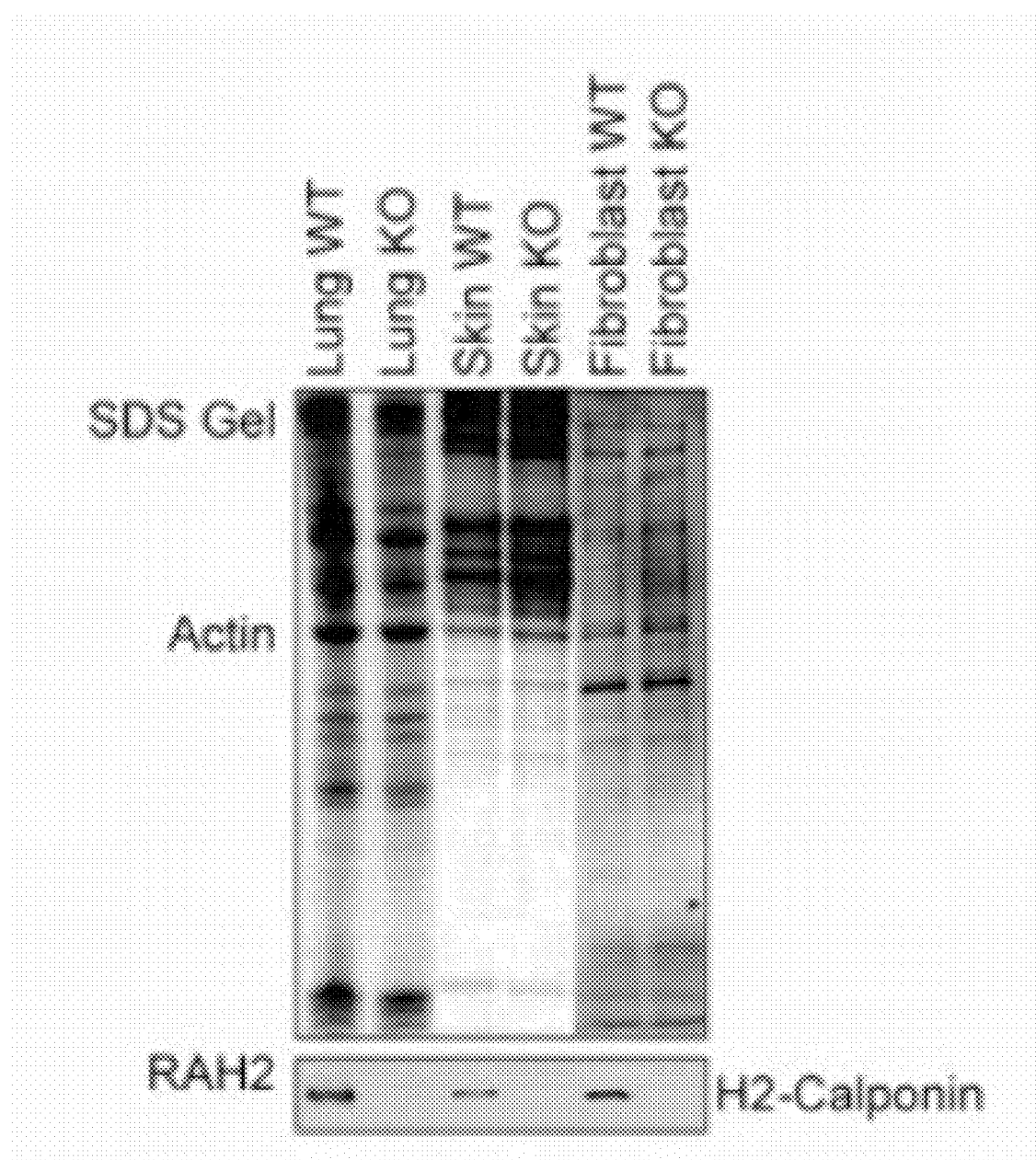
FIG. 13. Western blots showing h2-calponin expression levels in various tissues. Western blots of lysates from primary cultures of wild-type and h2-calponin knockout cells are also shown.

The capacity to resist stretching injury was used as a measure of the dynamic nature of the cytoskeleton. To determine the effect of reduced h2-calponin expression on cellular resistance to stretching injury, primary fibroblasts were isolated from wild-type and Cnn2-flox-neo mouse leg muscle. Cells from the second passage were seeded on a Bioflex plate with a collagen type I-coated silastic membrane bottom. To examine the resistance to stretch injury, preconfluent monolayer cells were transiently elongated by stretching the membrane to 124% for 250 milliseconds in an FX-4000T vacuum system (Flexcell International). Cells were immediately stained with propidium iodide and injuries were assessed by quantifying the number of cells that took up the membrane-impermeable dye (McKinney et al., Stroke, 27:934-40, 1996, incorporated herein by reference). FIG. 5. The Cnn2-flox-neo fibroblasts with diminished expression of h2-calponin showed a significantly higher rate of injury than control cells (FIG. 5, *P<0.001). Western blots of cell lysates from various tissues and from primary cultures of fibroblasts from wild-type and h2-calponin knockout mice were also prepared to determine if loss of h2-calponin could be compensated by expression of another calponin isoform. The results shown in FIG. 13 demonstrate that loss of h2-calponin, e.g., in the knockout mice, was not compensated by expression of another calponin isoform.

These studies show that h2-calponin plays a significant role in the dynamic capacity of the cytoskeleton to adapt to mechanical stress, including avoidance of stretching injury, and that the regulatory and functional properties of h2-calponin are not redundant or compensable.

EXAMPLE 6

H2-calponin Knockdown Affects Macrophage Differentiation

Figure 6:
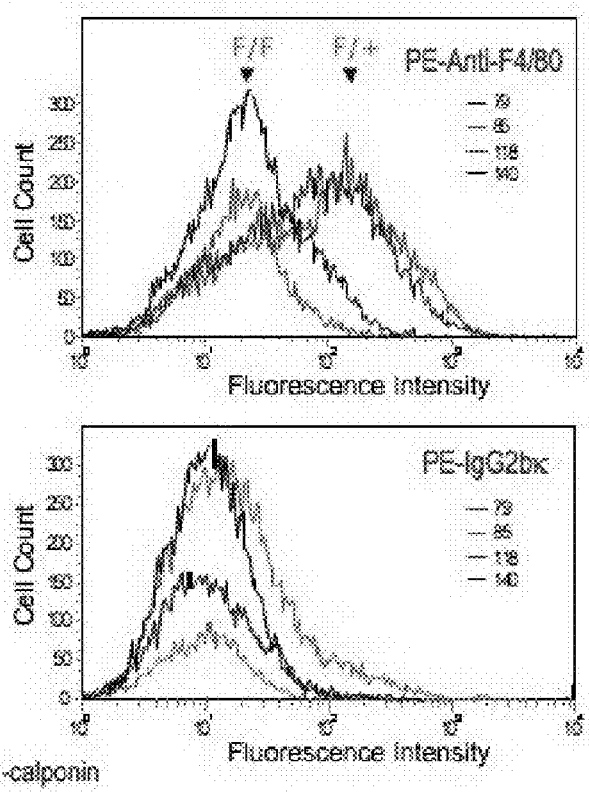
FIG. 6. H2-calponin knockdown affected macrophage differentiation. Bone marrow cells of heterozygous (F/+) and homozygous h2-calponin knockdown mice were isolated and grown in the presence of M-CSF for seven days. (A) Samples of cells were lysed and subjected to SDS-PAGE and Western blot (RAH2) analysis. (B) Living cells were subjected to FACS using the mouse macrophage-specific surface marker F4/80. The graph of cell count as a function of fluorescence intensity provides a measure of PE-labeled Ig isotype background fluorescence controls.

The capacity of bone marrow cells to differentiate into macrophages in the presence of the inducing agent M-CSF correlated inversely with the level of h2-calponin expression in those cells. Bone marrow cells were isolated from heterozygous (F/+) and homozygous (F/F) Cnn2-flox-neo h2-calponin knockdown mice (two mice each) and cultured in the presence of M-CSF for 7 days to induce macrophage differentiation (Schonlau et al., J Leukoc Biol. 73:564-73, 2003, incorporated herein by reference). A Western blot (RAH2 antibody probe) of total protein extracted from the differentiated cells showed diminished h2-calponin in homozygous cells compared to significant levels in heterozygous Cnn2-flox-neo cells (FIG. 6A). FACS analysis for the mouse macrophage-specific surface marker F4/80 (van den Berg et al., Trends Immunol. 26:506-9, 2005, incorporated herein by reference) showed drastically decreased expression of F4/80 (FIG. 6B, top panel), corresponding to the diminished h2-calponin level. The lower panel of FIG. 6B shows the PE-labeled Ig isotype background fluorescence controls.

EXAMPLE 7

H2-calponin Activity Affects White Blood Cell Numbers

To assess the effect of h2-calponin on white blood cell numbers, blood from mice of varying h2-calponin haplotype (heterozygous and homozygous mice as described in Example 6). Peripheral blood smears were Giemsa-stained and white blood cells counted under a microscope. Values provided in Table 1 are the percentage of total white blood cells (mean ±SD). 200 cells were randomly counted for each mouse and 3 mice were analyzed in each group. Decreased monocytes and neutrophils were found in the homozygotes of h2-calponin knockdown mice. *P<0.01 compared with wild type and *P<0.05 compared with heterozygous controls.

TABLE 1

Peripheral White Blood Cell (WBC) Counts (%)

|  | Wild Type | Heterozygous | Homozygous |
| --- | --- | --- | --- |
| Monocytes | 3.9 ± 0.4 | 3.4 ± 0.5 | 2.2 ± 0.6 * |
| Neutrophils | 10.7 ± 1.0 | 9.8 ± 1.0 | 6.6 ± 1.7 * |
| Eosinophils | 1.7 ± 0.3 | 1.6 ± 0.8 | 1.7 ± 0.7 |
| Basophils | 0.0 ± 0.0 | 0.0 ± 0.0 | 0.0 ± 0.0 |
| Lymphocytes | 83.7 ± 1.7 | 85.2 ± 2.0 | 89.4 ± 2.7 |

EXAMPLE 8

Cell Spreading

Figure 16:
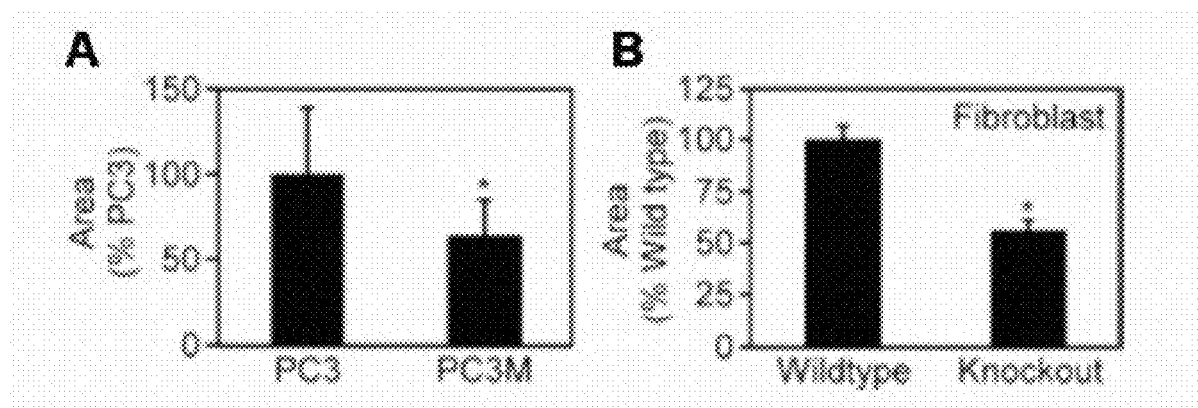
FIG. 16. Histograms showing the results of cell spreading area upon culturing PC3 and PC3-M cells (A), and upon culturing primary fibroblasts (B).

The effect of h2-calponin on cell spreading in culture was also assessed. PC3, PC3-M and primary fibroblasts were examined for the area of spreading in culture. The culture spreads were subjected to analysis using NIH Image software, and the results shown in FIG. 16 demonstrate that h2-calponin is positively correlated to cell spreading area (*P<0.001).

EXAMPLE 9

Anchorage-dependent Expression of h2-calponin

Figure 18:
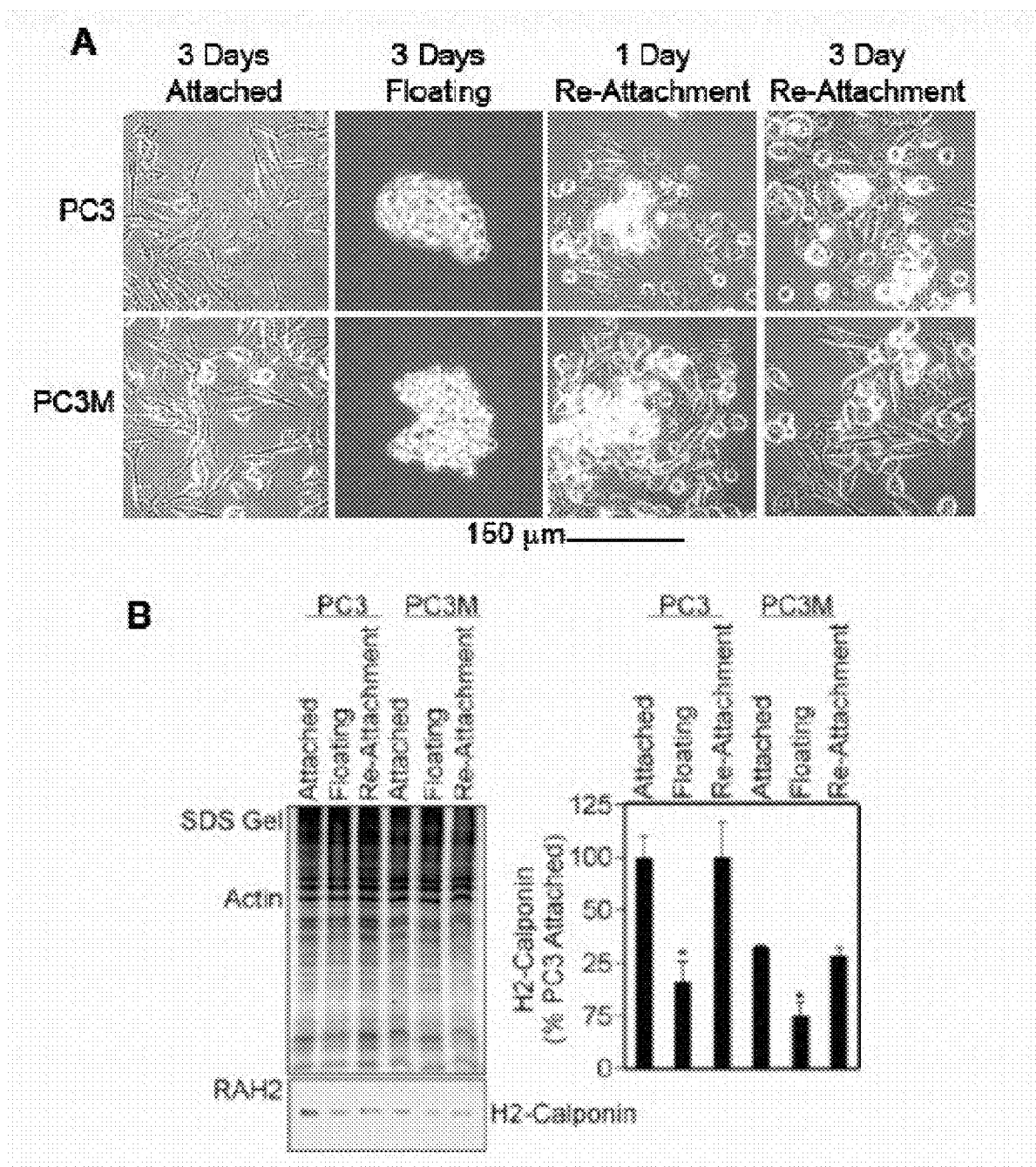
FIG. 18. Phase-contrast micrographs (A) and Western blot (B) as well as histogram (B) of percent of anchored or attached cells for PC3 and PC3-M cells cultured on various compatible and incompatible culture dishes.

The influence of cell anchorage to a suitable substrate on h2-calponin expression was also investigated. PC3 and PC3-M cells were cultured in compatible and non-compatible plastic dishes. In non-compatible plastic dishes, the cells did not anchor to a substrate, but rather formed floating aggregates (FIG. 18A). Western blots (RAH2 detection antibody) normalized to actin levels showed that h2-calponin was down-regulated in unanchored cells (FIG. 18B). Upon transfer of unanchored cells to compatible culture plates, the cells attached to the substrate and h2-calponin expression levels returned to normal levels under these conditions, confirming the positive correlation between h2-calponin expression level and cell anchorage.

Figure 19:
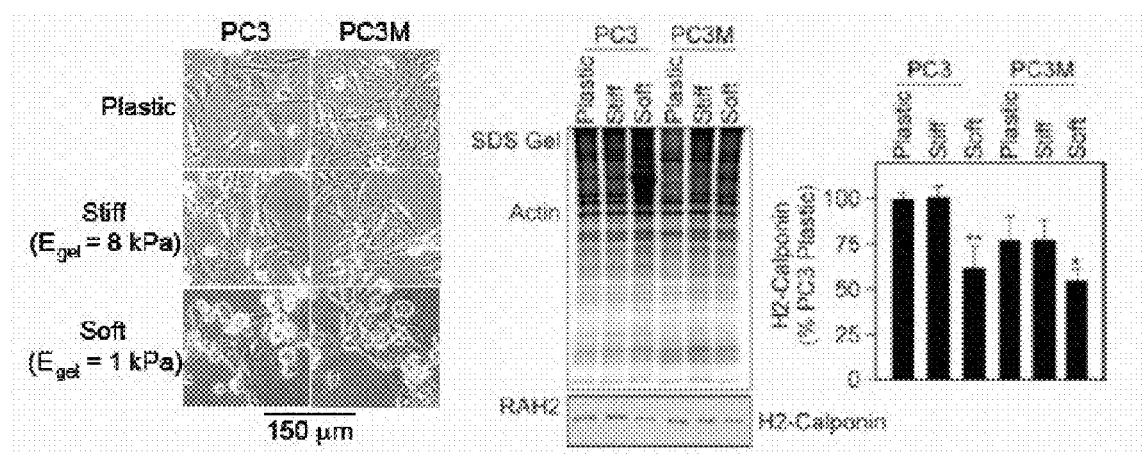
FIG. 19. Phase-contrast micrograph, Western blot and histogram of PC3 and PC3-M cells cultured on substrates of varying stiffness.

Exploring the influence of cell substrate on h2-calponin expression further, PC3 and PC3-M cells were cultured on a variety of plastic dishes or polyacrylamide gels of varying stiffness for three days. Cell lysates were prepared and Western blots revealed that both PC3 and PC3-M cells express less h2-calponin when cultured on a soft matrix that produced lower traction force and steady tension in the cytoskeleton (FIG. 19). Considered in view of the role of h2-calponin in stabilizing the actin cytoskeleton, the substrate stiffness-dependent expression of h2-calponin correlates well with the tendency of prostate cancer cells to metastasize to the bone. Accordingly, modulators of h2-calponin activity are expected to be useful in a variety of disease, disorders and conditions characterized by aberrant cell migration and/or proliferation and/or anchorage, including but not limited to prostate cancer and its metastasis, e.g., to the bone.

EXAMPLE 10

Macrophage Motility and Phagocytosis

Significant levels of the h2 isoform of calponin are expressed in the peripheral blood cells of the myeloid lineage. The physiological role of h2-calponin in these cells was therefore investigated. The experiments disclosed herein establish that h2-calponin-free macrophages demonstrated a higher rate of proliferation and faster migration than did h2-calponin-positive cells, consistent with a faster diapedesis of peripheral monocytes and neutrophils. H2-calponin-free macrophages also demonstrated reduced spreading in adhesion culture together with an increase in tropomyosin in the actin cytoskeleton. The lack of h2-calponin also significantly increased macrophage phagocytic activity, indicating a novel mechanism for regulating phagocyte functions. Given the mobility of leukocytes and the central role played by their actin cytoskeleton in locomotion, transmigration and phagocytosis, the disclosure provides a new avenue for preventive and/or therapeutic treatment of defensive and autoimmune disorders.

A variety of techniques were employed in conducting the experiments described below. Cloning of mouse Cnn2 genomic DNA encoding mouse h2-calponin began with a 129SvJ strain mouse genomic DNA library in λ DASHII phage vector (20, 21). From this library, clones bearing genomic DNA segments containing the h2-calponin gene were isolated using a [$^{32}$P]-labeled mouse h2-calponin cDNA probe. The plating of λ phage, making of nylon membrane replicas, hybridization and autoradiography were carried out as described previously (21). The plaque-purified positive phages were amplified in XL-1B MFA P2 *E. coli* and purified by CsCl density gradient centrifugation. The recombinant phage DNA was isolated by phenol/chloroform extraction and subcloned into plasmid vectors as overlapping restriction endonuclease fragments. Restriction mapping, Southern analysis, and partial sequencing were carried out to verify the cloned Cnn2 genomic DNA in comparison with the mouse genomic DNA sequence in a public database (Gene ID: MGI: 105093).

Figure 20:
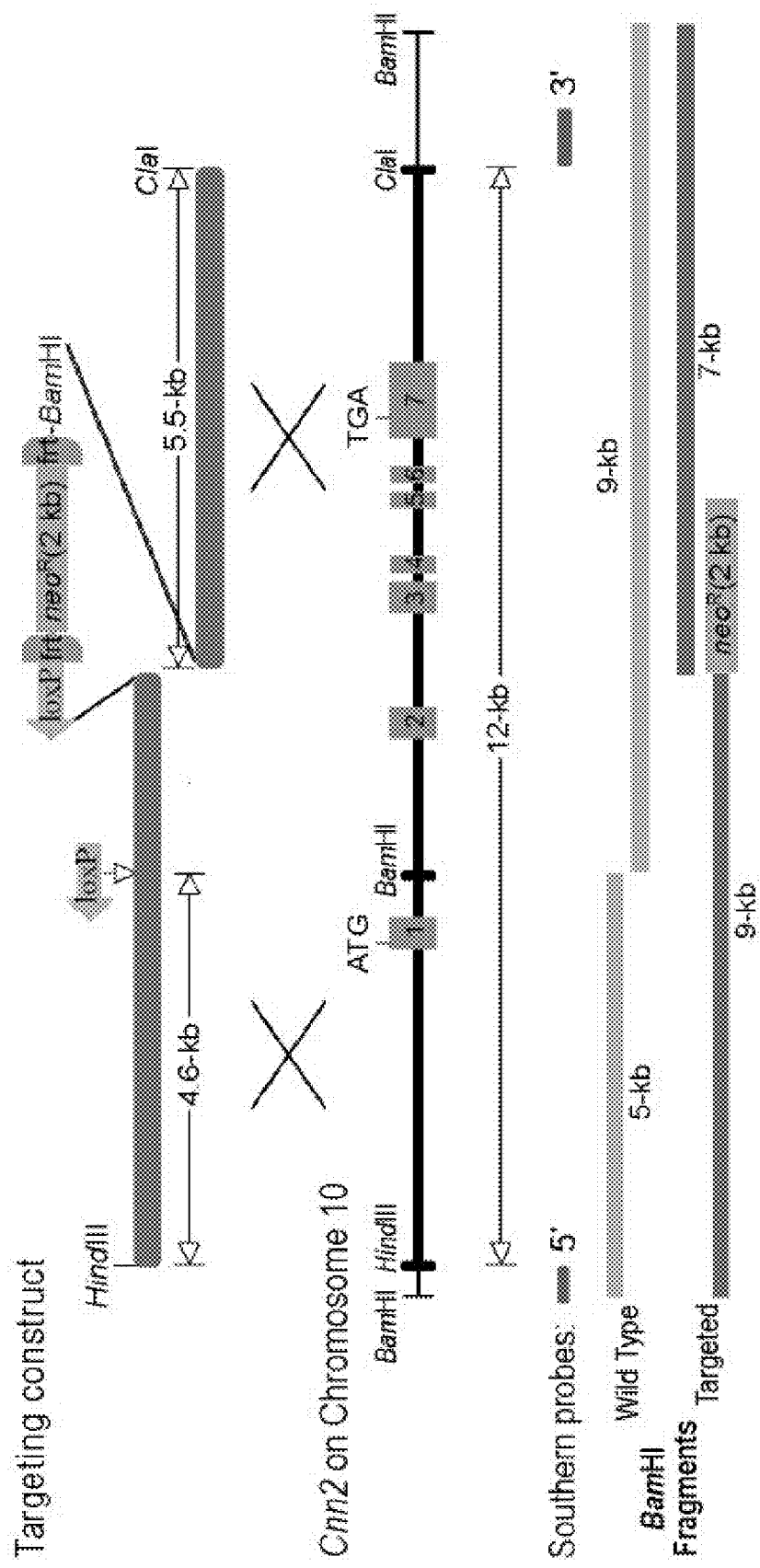
FIG. 20. H2-calponin gene-targeting vector. In the conditional Cnn2 gene-targeting construct shown on the top, two loxP sequences were placed in tandem orientation flanking exon 2. A neoR cassette was inserted into intron 2 next to the downstream loxP as a selection marker. Two tandem frt sequences were placed flanking the neoR cassette. The 4.6 kb and 5.5 kb flanking arms in the construct provide sufficient regions for homologous recombination. Exon locations and positions of the translation initiation codon (ATG) and termination codon (TGA) of the h2-calponin gene are indicated in the wild-type mouse genomic map shown in the middle. The positions of the 5' and 3' endogenous genomic DNA probes and the predicted BamHI restriction fragments recognized by the probes in Southern blot genotyping for the wild-type and h2-calponin gene targeted alleles are outlined at the bottom.

Knockout mice containing an inactivated Cnn2 gene that did not express h2-calponin was constructed as follows. A mouse Cnn2-targeted conditional mutagenesis construct was generated using the pPNT4 vector (22). Illustrated in FIG. 20A, two loxP sequences were inserted into intron 1 and into intron 2 in tandem orientation to allow Cre recombinase-catalyzed deletion of exon 2. The deletion of exon 2 not only removed a portion of the coding sequence but also resulted in a reading frame shift in the downstream mRNA after codon number 21. The shifted reading frame was terminated by a stop codon after encoding 11 missense amino acids. This Cre-mediated deletion of exon 2 can be induced in whole animals as well as in tissues or in cultured cells. A neoR cassette adjacent to the downstream loxP sequence as constructed in the pPNT4 vector was inserted into intron 2 of the Cnn2 targeting construct for neomycin selection of the transfected ES cells. The neoR cassette is flanked by two frt sequences and can be deleted by Flp1-catalyzed recombination (23). This mechanism allows the removal of the neoR cassette after establishing the targeted loxP mutagenesis to avoid the effect of neoR insertion on h2-calponin expression. The induction of neoR removal can be done in whole animals, tissues or cells. Transfection of mouse HM-1 ES cells (x,y) with the h2-calponin gene targeting DNA construct was accomplished using electroporation. Colonies of the transfected ES cells were selected by the acquisition of neomycin resistance conferred by the gene targeting construct. Genomic DNA from the drug-resistant ES cell colonies was extracted by proteinase K digestion and screened by Southern blotting using cloned 5' and 3' flanking genomic DNA probes for the homologous recombination-generated change of the BamHI restriction pattern (FIG. 20A).

Ten μg each of the ES cell genomic DNA was digested by BamHI, separated by 0.8% agarose gel electrophoresis, and transferred to nylon membrane by capillary action using a standard Southern blotting method. The membrane was pre-hybridized at 55° C. for 2 hours in 0.25 M $Na_2HPO_4$, 14 mM $H_3PO_4$, 1 mM EDTA, 1% bovine serum albumin (BSA), 5% SDS, 0.1 mg/ml mechanically sheared salmon sperm DNA, and 20% formamide. The 5' and 3' DNA probes were labeled with [$^{32}$P]-dCTP, heat-denatured, and added to the rolling hybridization flask together with 5% (w/v) dextran sulfate for incubation at 55° C. for 16 hours. The membrane was then washed repeatedly with 40 mM sodium phosphate buffer containing 1% SDS and 1 mM EDTA to gradually reach 60° C. and examined by autoradiography.

Two original Cnn2 targeted mouse ES cell clones identified by Southern screening, 21C7 and 21H2, were used to produce chimeric mice. The blastocyst injection and embryo re-implantation were carried out using conventional techniques. The 129SvJ originated (albino) ES cells were injected into C57BL/6 (black) mouse blastocysts to produce chimeras. High chimerism males from the two targeted ES cell lines were mated with C57BL/6 females to test germ line transmission. The ES cell-originated offspring were first selected by the brown coat color in contrast to the pure C57BL/6 black litter mates. The presence of the targeted Cnn2 allele in the ES cell-originated pups was then genotyped by polymerase chain reaction (PCR) on genomic DNA extracted from tail biopsies. Two pairs of PCR primers were designed (FIG. 23B) to identify the presences of the upstream loxP and the neoR cassette, respectively. Mice bearing the targeted Cnn2 allele were selected to mate with C57BL/6 for multiple generations to obtain a uniform genetic background. Disruption of the h2-calponin gene was obtained by deletion of the exon 2 region through crossing the Cnn2-flox mouse line with the Zp3-cre mouse line (Jackson Lab) that expresses Cre recombinase in the female germ line. Removal of the neoR cassette inserted into intron 2 was achieved by crossing the Cnn2-flox-neo line with a Gt(ROSA)26Sor-FLP transgenic mouse line (Jackson Lab) that expresses FLP1 recombinase in most tissue types, including the developing germ line.

Representative tissue samples, obtained from adult (4-5 months old) wild-type and Cnn2-targeted mice, were lysed and subjected to SDS-PAGE and Western analyses. Immediately after euthanasia, the tissues were rapidly dissected on ice and briefly rinsed in cold phosphate buffered saline (PBS). Total proteins were extracted immediately from the tissues by mechanical homogenization in SDS-PAGE sample buffer containing 2% SDS and heated at 80° C. for 5 minutes. SDS-PAGE samples of isolated or cultured cells were prepared similarly, omitting the homogenization step. The protein extracts were examined by SDS-PAGE using the Laemmli buffer system and Coomassie Blue R250 staining. Duplicate gels were electrically blotted onto nitrocellulose membrane using a BioRad semi-dry transfer apparatus for Western analysis. After blocking with 1% BSA or 5% powdered skim milk in Tris-buffered saline (TBS), the membrane was incubated with a rabbit antiserum, RAH2, raised against mouse h2-calponin with a weak cross-reaction to h1-calponin (24), a mouse anti-h1-calponin monoclonal antibody (mAb) CP1 (25), mouse anti-h2-calponin mAbs CP21 and 1D2 (3, 18) or anti-tropomyosin mAbs CG3 (26) in TBS containing 0.1% BSA or 0.5% powdered skim milk to examine the expression of calponin and tropomyosin isoforms. The blots were washed with TBS containing 0.05% Tween-20 and incubated with alkaline phosphatase-labeled anti-rabbit IgG or anti-mouse IgG second antibody (Sigma). After final washes, the blots were processed for 5-bromo-4-chloro-3-indolyl phosphate and nitroblue tetrazolium chromogenic substrate reaction (4). Densitometry analyses of SDS-gels and Western blots were performed on digital images scanned at 600 dpi using the NIH Image software version 1.61. Quantification of the SDS-gel and Western blots was done by normalization to the amount of actin, total cellular protein, or histones determined in parallel SDS-gels.

Primary cultures of human monocytes/macrophages were also established by initially isolating human monocytes by elutriation from the peripheral blood of anonymous healthy donors. The purified peripheral monocytes were suspended in serum-free RPMI 1640 medium, and allowed to adhere to cell culture dishes at 37° C. in 5% $CO_2$ for 1 hour before change to medium containing 20% fetal bovine serum (FBS), 100 μg/ml penicillin, 100 μg/ml streptomycin and 1 μg/ml of polymyxin B. The adherent cells were allowed to differentiate into macrophages in culture for up to 7 days as described previously (27-33).

Mouse peritoneal cells were also collected and immunophenotyped. Peritoneal residential cells were lavaged with PBS from wild-type and h2-calponin knockout mice. Mouse peritoneal cells were also elicited by injection of 2 ml of 3% thioglycollate broth 12 and 72 hours prior to lavage. The same volume (8 ml) of PBS was used for each animal so the total number of cells lavaged could be compared.

Cell types were identified by immunophenotyping with fluorescence-conjugated antibodies recognizing specific cell surface markers of myeloid cell (Mac-1), macrophage (F4/80) and granulocyte (Gr-1) cells, followed by flow cytometry analysis. $5\times10^5$ cells from each mouse were first incubated with anti-mouse CD16/CD32 antibody (BD Pharmingen) to block the cell surface Fc III/II receptor and then stained with fluorescein isothiocyanate (FITC)-conjugated anti-Mac1 (Mac1-FITC, Serotec), Allophycocyanin (APC)-conjugated anti-F4/80 (F4/80-APC, Serotec), and phycoerythrin-Cy7 (PEcy7)-conjugated anti-Gr1 (Gr1-PEcy7, eBioscience, CA) antibodies at room temperature for 30 minutes. After washing away the unbound antibodies, the cells were analyzed using a BD LSR II flow cytometer (BD Biosciences, Mountain View, Calif.) with BD FACSDIVA software. Using FCS Express software (De Novo software, Los Angeles, Calif.), macrophages were identified as strong Mac1-positive, F4/80-positive and Gr1-negative, whereas granulocytes were identified as strong Mac1-positive, F4/80-negative and Gr1-positive.

An in vitro wound healing assay was used to assess cell migration and rate of wound closure. Residential mouse peritoneal cells were collected in RPMI 1640 medium containing 10% FBS, 100 μg/ml penicillin and 100 μg/ml streptomycin and seeded in 12-well culture plate at $1\times10^6$ per well to allow high density adhesion of macrophages. After removing the floating cells, the cells were incubated at 37° C. in 5% $CO_2$ for 24 hours to form a confluent monolayer. The macrophage monolayer was wounded by scratching with a thin pipette tip and examined at a series of time points under a phase-contrast microscope. The width of the wounds was measured from photographs to evaluate the rate of cell migration during the course of healing.

RAW264.7 mouse macrophage cells (34) (ATCC TIB-71) were transfected by initially seeding the cells at $2 \times 10^6$ cells per 100 mm dish in DMEM containing 10% FBS, 100 μg/ml penicillin and 100 μg/ml streptomycin at 37° C. in 5% $CO_2$ and cultured for 24 hours prior to transfection of recombinant pcDNA3.1 plasmid DNA expressing mouse h2-calponin under the cytomegalovirus (CMV) promoter (18). Two μg DNA in 50 μL DMEM was mixed with 5 μL Lipofectamin (Invitrogen) and incubated at room temperature for 20 minutes before gently mixing with 5 ml DMEM and adding to the RAW264.7 cell culture. After incubation at 37° C. in 5% $CO_2$ for 6 hours, 5 ml DMEM containing 20% FBS was added to the dish and the culture was further incubated for 18 hours before change to fresh media. To establish RAW264.7 cell lines stably expressing h2-calponin, transfected cells were selected by G418 (500 μg/ml) and drug-resistant single colonies were individually picked as described previously (18). The integration of the sense and antisense h2-calponin cDNA transgenes in the stably transfected RAW cell lines was verified by PCR. The expression of h2-calponin in the sense cDNA-transfected cells was examined by Western blotting using the RAH2 antibody.

A cell proliferation assay was also performed. RAW264.7 cells stably transfected with sense and antisense h2-calponin cDNA were seeded in 96-well culture plates at $10^3$ cells per well. Non-transfected RAW264.7 cells were used as control. The rate of cell proliferation was examined at a series of time points by Crystal Violet staining of nuclei as described previously (18). Multiple stable transfected cell lines were examined to avoid line-to-line differences.

Immunofluorescence microscopy was undertaken to examine the cellular localization of h2-calponin in macrophages and to determine the effect of the Cnn2 knockout mutation on the structure of the macrophage actin cytoskeleton. Residential mouse peritoneal macrophages were initially cultured as a monolayer on glass cover slips for 24 hours and stained with anti-h2-calponin antibody RAH2 and normal rabbit serum control, followed by TRITC- or FITC-labeled anti-rabbit IgG second antibody (Sigma) as described previously (18). Actin filaments were stained with TRITC-phalloidin and tropomyosin was stained with mAb CG3 (26) hybridoma supernatant with SP2/0 myeloma supernatant as control and TRITC- or FITC-labeled anti-mouse IgG second antibody. The results were observed under a Zeiss Axiovert 100H epifluorescence microscope and photographed.

Phagocytosis was assessed by the uptake of fluorescent latex beads (35-38). After opsonization by incubation in 50% pooled normal mouse serum diluted in Krebs-Ringer PBS (pH 7.4) for 30 minutes, red-fluorescence carboxyl microspheres (excitation/emission maxima at 580 nm/605 nm, Molecular Probes) were incubated with mouse residential and elicited peritoneal cells ($1 \times 10^6$) at a particle to cell ratio of 50:1 in 0.5 ml RPMI 1640 medium containing a final concentration of 5% mouse serum at 37° C. in 5% $CO_2$ for 1 hour. The cells were then thoroughly washed with PBS 3 times to remove the free and extracellularly bound particles and immediately stained with F4/80-APC and Gr1-PEcy7 antibodies as described herein. After washing to remove the unbound antibody, the cells were fixed with 1% formalin in PBS. Uptake of the fluorescent beads was measured using a BD FACSArray flow cytometer at 532 nm laser excitation. Phagocytotic activity was analyzed using FCS Express software.

All quantitative data are presented as mean ±SD or SEM as noted in the brief description of the drawing. Statistical analysis was done with Student's t test using Microsoft Excel computer program.

Using the techniques described herein and other techniques known in the art, results were obtained that showed that h2-calponin was highly expressed in human peripheral blood mononuclear cells, in human myelogenous leukemia cell line K562 (ATCC CCL-243), and in human monocyte line THP-1 (ATCC TIB-202) (FIG. 21A). Although h2-calponin is minimally detectable in un-differentiated human promyeloblast line HL-60 (ATCC CCL-240), the expression was significantly up-regulated after DMSO-induced differentiation in culture for 5 days (39). In contrast, h2-calponin was not detectable by RAH2 polyclonal antibody in human T lymphocyte line Jurkat (ATCC TIB-152), mouse T lymphocyte line BW5147 (ATCC TIB-47), mouse plasmacytoma cell line T1165 (40), and mouse myeloma cell line NS-1 (41) (FIG. 21B). The data demonstrated a myeloid cell-specific expression of h2-calponin.

To investigate the function of h2-calponin in differentiated myeloid cells, we examined the expression of h2-calponin during monocyte to macrophage differentiation. Employing histone as a control for the amount of chromosomal DNA and, therefore, the number of cells, SDS-PAGE showed that cellular actin contents significantly increased during macrophage differentiation (FIG. 22A), consistent with increased cytoskeleton function in macrophages. H2-calponin decreased early during macrophage differentiation (1 day in the adherent culture) and significantly increased after differentiation for 4-7 days into mature macrophage, when normalized against the level of actin or histone (FIG. 22B). The lower level of h2-calponin in monocytes compared to that found in macrophages is consistent with the established functional differences between the two cell types, such as the highly mobile nature of peripheral monocytes versus the fact that macrophages largely remain in tissues (42).

Figure 23:
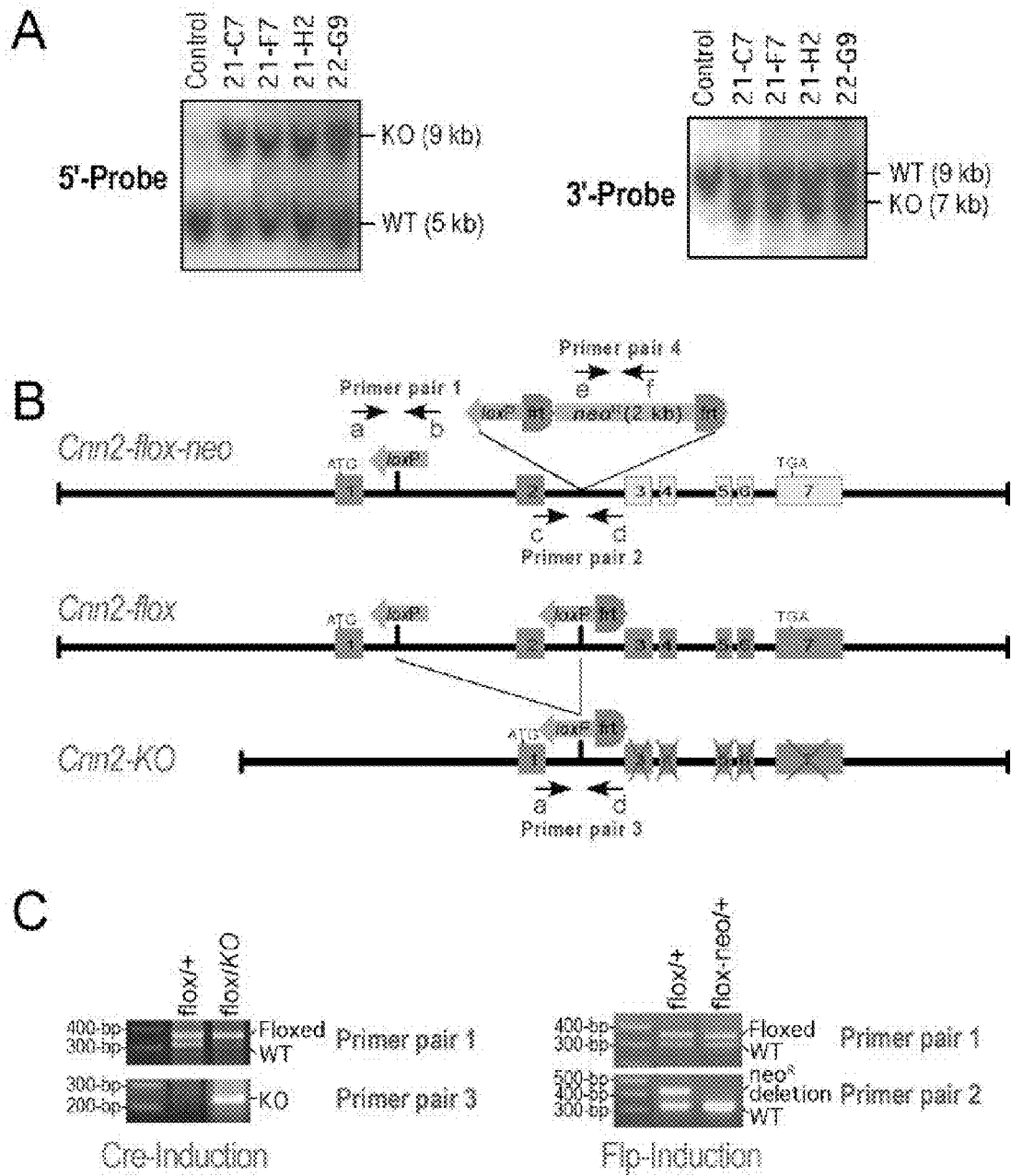
FIG. 23. Genotyping of Cnn2-targeted mouse ES cells. (A) Southern blot screening of the targeted Cnn2 allele in mouse ES cells. Genomic DNA of transfected ES cell clones was digested by BamHI and hybridized with 32P-labeled 5' and 3' flanking genomic DNA probes (FIG. 20). The left panel shows that the 5' probe detected a 9 kb band from the targeted allele (KO) (knockout) in 4 representative positive clones. The presence of the 5 kb band from the wild-type (WT) allele indicated these cells were heterozygotes for the targeted Cnn2 allele. The right panel shows the same blot (after stripping the 5' probe) re-probed with the 3'-flanking probe to detect the targeted allele as a 7 kb fragment together with the approximately 9 kb WT (wild-type) allele band. (B) Maps of three modified Cnn2 alleles: Cnn2-flox-neo is the original Cnn2-targeted allele illustrated in FIG. 20. The expression of exons 3-7 is negatively affected by the neoR cassette inserted into intron 2, resulting in a knockdown effect. The Cnn2-flox allele is derived from the original Cnn2-targeted allele by Flp-induced removal of the neoR cassette, restoring the normal expression of h2-calponin. The Cnn2-KO allele is derived by further deletion of exon 2 through Cre-induced recombination, resulting in a reading frame shift in exons 3-7 and knockout of the expression of h2-calponin. The positions of 6 primers used in 4 pairs for PCR genotyping are outlined on the maps. (C) PCR genotyping of the Cnn2 targeted alleles: The left panel shows agarose gels of PCR detections of the insertion of the loxP sequence in intron 1 and the Cre-induced deletion of exon 2 (the PCR conditions for primer pair 3 would detect the Cnn2-KO but not Cnn2-flox allele). The right panel shows agarose gels of PCR identification of the Flp-induced removal of the neoR cassette (the PCR conditions for primer pair 2 would detect the Cnn2-flox but not Cnn2-flox-neo allele) together with the control of loxP detection. The presence or absence of the neoR cassette was confirmed by PCR using primer pair 4.

Cnn2-targeted mouse lines were also generated. Using the gene targeting construct derived from 129SvJ mouse genomic DNA that is syngeneic to the HM-1 mouse ES cells used in this study, successful targeting of Cnn2 gene was achieved. More than 20 Cnn2-targeted ES cell clones were obtained from about 190 candidate clones that survived G418 selection. The Southern blots in FIG. 23A using the 5' and 3' genomic DNA probes (FIG. 20) showed representative genotyping results of the h2-calponin gene targeted mouse ES cells. The two targeted ES cell lines selected for blastocyst injection both produced chimeric offspring with high frequency germ line transmission. The development of Cnn2 gene-targeted founder mouse lines from two original targeted ES cell clones allows phenotypic characterizations avoiding line-to-line variations. PCR genotyping of the ES cell-originated offspring showed Mendelian segregation of the Cnn2-flox-neo allele. PCR genotyping further demonstrated that the neoR selection marker was effectively removed by crossing with the Gt(ROSA)26Sor-FLP mouse line to produce the Cnn2-flox allele (FIGS. 23B and 23C). Crossing with the Zp3-cre mouse line effectively produced deletion of exon 2 of the h2-calponin gene to produce the Cnn2-Knockout (KO) allele (FIGS. 23B and 23C).

Figure 21:
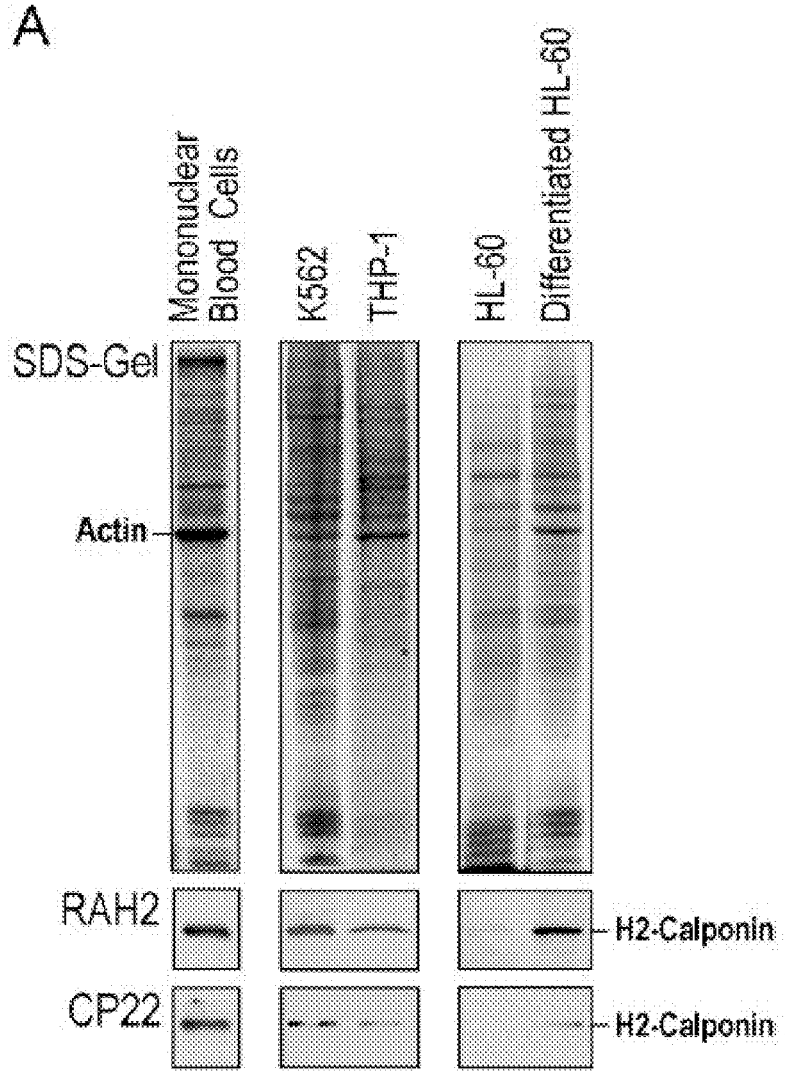
FIG. 21. Expression of h2-calponin in myeloid cells. (A) Western blots using anti-h2-calponin polyclonal antibody RAH2 and mAb CP22 on total protein extracted from human peripheral mononuclear cells, human myelogenous leukemia cell line K562, human monocyte line THP-1, and in vitro differentiated human myeloid leukemia cell line HL-60 detected significant amounts of h2-calponin. (B) No calponin expression was detectable in human T lymphocyte line Jurkat, mouse T lymphocyte line BW5147, mouse plasmacytoma line T1165 and mouse myeloma cell line NS-1 by RAH2 Western blot.
Figure 21:
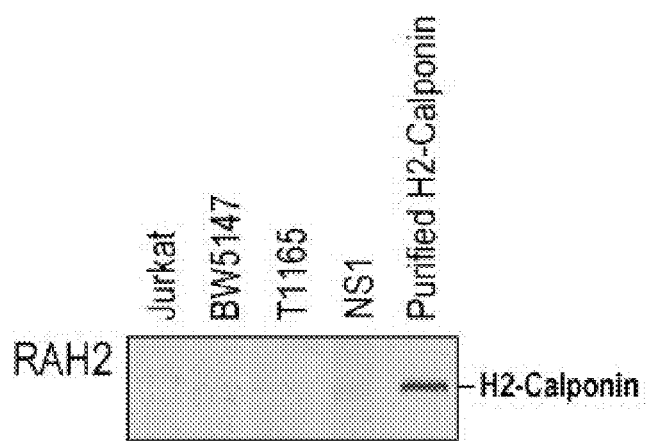
Figure 22:
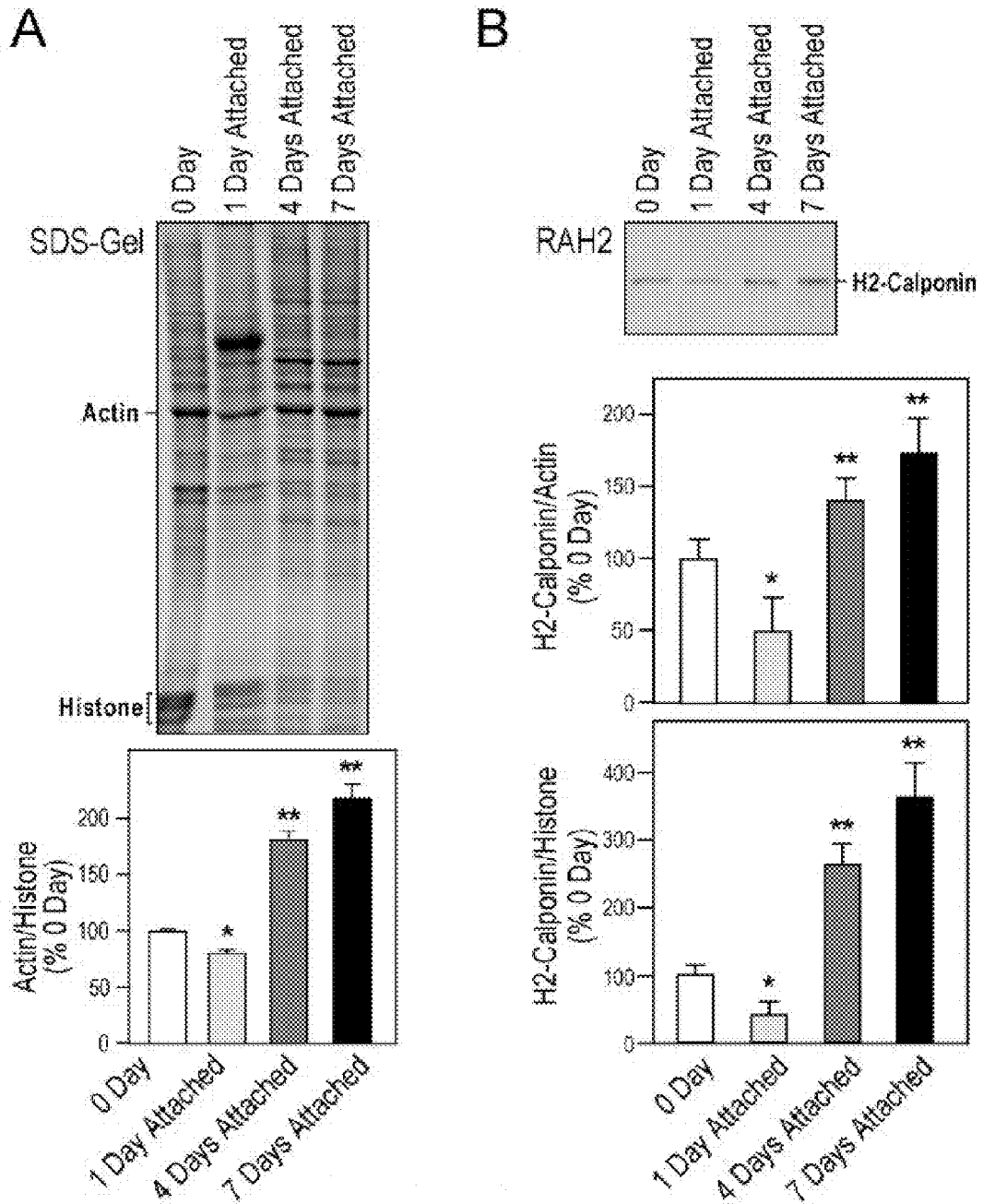
FIG. 22. Expression of h2-calponin during monocyte-macrophage differentiation. H2-calponin expression was examined during adhesion-dependent differentiation of human peripheral monocytes. Fresh isolated monocytes adhered to plastic dishes were cultured to differentiate in vitro into macrophages. (A) The total cellular protein extracts from the cells before (0 day) and 1, 4 and 7 days in culture were examined by SDS-PAGE. Gel densitometry analysis demonstrated a decrease followed by significant increases in actin as normalized by histone levels that reflected cell numbers. *$P<0.05$ and **$P<0.01$ versus the Day 0 level. (B) Western blots using RAH2 antibody and densitometry quantification demonstrated the expression of h2-calponin normalized by the level of cellular actin or histone showed a decrease in h2-calponin at the early stage of monocyte-macrophage differentiation followed by significant increases during the later stages of differentiation. *$P<0.005$ and **$P<0.001$ versus the Day 0 level.
Figure 24:
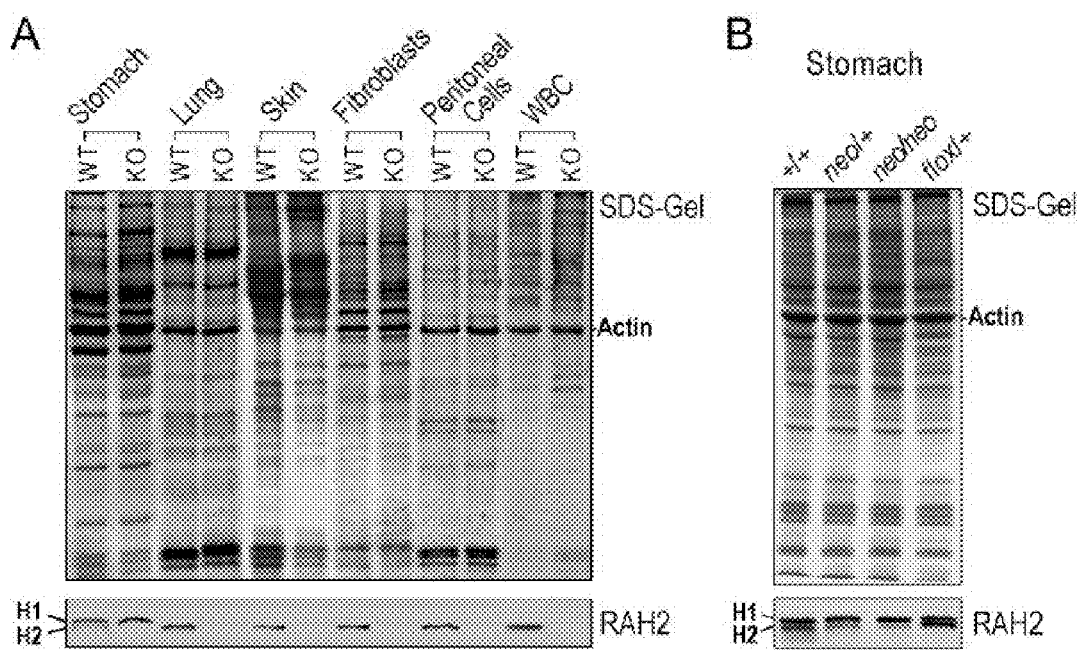
FIG. 24. Knockout and reversible knockdown of h2-calponin in Cnn2 gene targeted mice. (A) Knockout of h2-calponin in representative mouse tissue and cell types. The SDS-PAGE and Western blots showed that h2-calponin was absent in stomach (smooth muscle), lung (alveolar cells), skin (keratinocytes), fibroblasts, peritoneal residential cells, and peripheral white blood cells of Cnn2-KO (KO) mice, whereas these tissue and cell types in wild-type (WT) mice expressed h2-calponin at significant levels. (B) The SDS-PAGE and Western blot showed that the level of h2-calponin significantly decreased in the stomach of a Cnn2-flox-neo heterozygous mouse and was even further decreased in Cnn2-flox-neo homozygotes, demonstrating dominant knockdown effects. Flp-induced removal of the neoR cassette from intron 2 of Cnn2 effectively restored the expression of h2-calponin to wild-type levels. +, wild type Cnn2 allele.

Mice harboring mutated Cnn2 alleles (knockout or knockdown) were successfully generated. Mice homozygous for the Cnn2-KO allele (FIG. 23B) survive to adulthood and are fertile. The Western blots in FIG. 24A showed complete loss of h2-calponin in representative tissue and cell types known to normally express h2-calponin, i.e., smooth muscle (that also expresses h1-calponin (18)), lung alveolar cells (4), epidermal keratinocytes (3), fibroblasts (3), peritoneal residential cells and peripheral white blood cells (FIGS. 21 and 22). Although the deletion of exon 2 retained a short 5' reading frame in the mRNA encoding the first 21 amino acids of h2-calponin followed by 11 missense amino acids, no corresponding protein fragment was detected by the polyclonal anti-h2-calponin antibody RAH2 in the Cnn2 targeted mouse tissues, confirming the complete knockout effect. It is important to note that the level of h1-calponin was not significantly changed in the h2-calponin null smooth muscle tissues (FIG. 24), indicating that the calponin isoforms are non-redundant regulatory proteins.

A valuable side effect is that the insertion of the neoR cassette into intron 2 of h2-calponin gene (FIG. 23C) resulted in a significant knockdown of h2-calponin expression (FIG. 24B), likely due to an interruption of the transcription of full-length h2-calponin pre-mRNA. Showing various extents of decreases in h2-calponin level in tissue types that normally express h2-calponin, the h2-calponin knockdown mice also survive to adulthood and are fertile. While Cnn2-flox-neo homozygotes exhibited significant knockdown of h2-calponin expression, Cnn2-flox-neo/+ heterozygotes showed intermediate decreases in h2-calponin level (FIG. 24B). This observation indicates that h2-calponin expression is dependent on the gene dosage, consistent with a non-redundant function. Deletion of the neoR cassette by Flp recombinase produced an effective rescue of the h2-calponin gene expression. The Western blot in FIG. 24B showed a complete restoration of the h2-calponin protein level. In addition to demonstrating the feasibility of removing the neoR cassette from the genome of Cnn2 targeted mice, the results showed that the Cnn2-flox-neo allele provides an experimental system of reversible h2-calponin knockdown for treatments based on reversible expression of h2-calponin and for studies on the functional effects of rescuing h2-calponin expression in tissues and cells.

To investigate the physiological effects of h2-calponin deficiency in myeloid cells, peripheral blood white cells were examined. The results in Table 2 show decreased numbers of peripheral monocytes and neutrophils in adult h2-calponin knockdown and knockout mice as compared with age-matched wild-type controls. The ratios of eosinophils and basophils were not significantly decreased. The minimal level of h2-calponin detected in undifferentiated HL-60 human promyeloblast cells (39) (FIG. 21A) indicated that h2-calponin may be expressed in only a subset of differentiated myeloid cells in the granulocyte-monocyte progenitor lineage.

TABLE 2

Decreased peripheral monocytes and neutrophils in h2-calponin knockdown and knockout mice

| | Wild type | Cnn2 Knockdown | Cnn2 Knockout |
|---|---|---|---|
| Monocytes | 3.7 ± 0.3 | 2.2 ± 0.5* | 2.1 ± 0.5* |
| Neutrophils | 10.5 ± 0.7 | 6.4 ± 1.2* | 6.3 ± 0.8* |
| Eosinophils | 1.7 ± 0.3 | 1.7 ± 0.4 | 1.7 ± 0.3 |
| Basophils | 0.0 ± 0.0 | 0.0 ± 0.0 | 0.0 ± 0.0 |
| Lymphocytes | 84.1 ± 1.1 | 89.7 ± 1.8 | 89.9 ± 1.2 |

Peripheral blood smears of wild type, h2-calponin knockdown and h2-calponin knockout mice were stained with Giemsa stain and white blood cells were counted under a microscope. Two hundreds cells were randomly counted for each mouse and 4 mice were examined in each group. The values shown are the percentage of total white blood cells (mean ± SD). Decreased numbers of monocytes and neutrophils were found in the h2-calponin knockdown and knockout mice.
*$P < 0.001$ compared with the wild type control.

Figure 25:
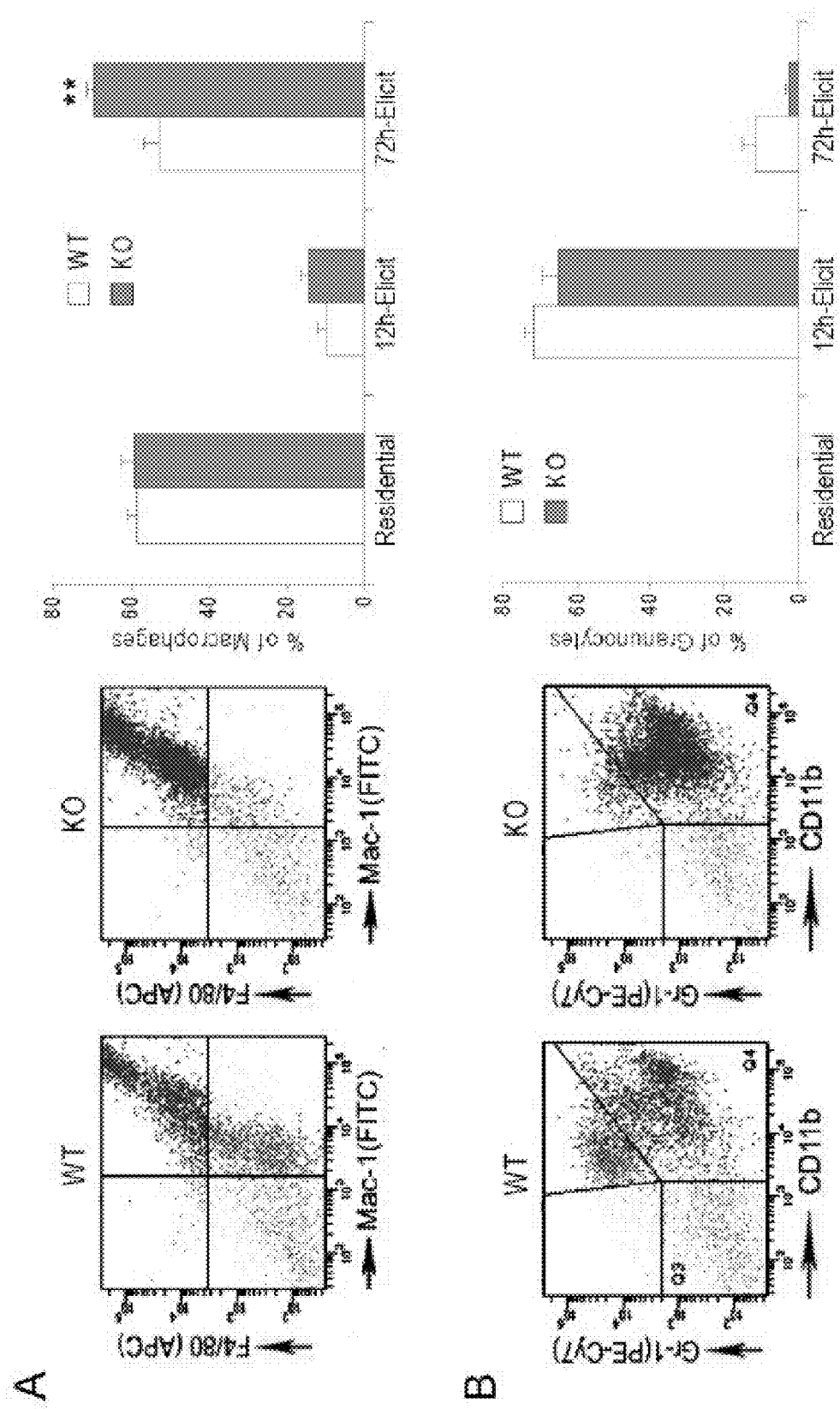
FIG. 25. Increased diapedesis of h2-calponin-free macrophages. The left panels show representative flow cytometry histograms of 72 hour-elicited peritoneal cells with the panels identifying macrophages (A) and granulocytes (B). The Mac-1+ population is indicated on the x-axis (FITC) and the Gr-1 (PE-Cy7) or F4/80 (APC) is indicated on the y-axis. Macrophages were identified as strongly Mac1-positive, F4/80-positive and Gr1-negative, whereas granulocytes were identified as strongly Mac1-positive, F4/80-negative and Gr1-positive staining. The upper right quadrant represents the double-positive cells that represent macrophages (A) and granulocytes (B). The right panels show the summarized results that the percent of 72 hour-elicited macrophages was significantly higher in h2-calponin KO mice than in the wild-type control (**, $P<0.01$) (A) whereas the % of 72 hour-elicited granulocytes showed a lower trend in h2-calponin KO mice than that in wild-type mice (B). n=7 mice in each experimental group, except for n=5 or the 72 hour-elicited h2-calponin KO group.

The decreased numbers of neutrophil and monocyte in the peripheral blood of h2-calponin knockdown and knockout mice could result from reduced production, more rapid turn over, or faster migration into tissues. Therefore, the total number of myeloid cells, as well as the percentage of F4/80+ macrophages and Gr-1+ granulocytes in residential and thioglycollate-elicited peritoneal cells from wild-type and h2-calponin-knockout mice were examined. The residential and elicited total cell counts and the number of Mac-1+ myeloid cells were not significantly different between the knockout and wild-type mice. However, the results showed that 72 hours after thioglycollate stimulation, macrophages were the dominant cell type in the peritoneum and the ratio of macrophage to total peritoneal cells was higher in the knockout mice than in the wild-type mice (FIG. 25A). In contrast, the number of peritoneal granulocytes was significantly lower 12 hours after thioglycollate stimulation ($9.9+1.4 \times 10^6$ versus $16.9+1.5 \times 10^6$, $P<0.01$) when granulocytes are the dominant cell type, and this trend remained 72 hours after stimulation (1.9±0.5% versus 7.5±2.8%). The same trend was also shown by the percent of granulocytes in total peritoneal cells (FIG. 25B). Together with the decreased number of neutrophils in peripheral blood (Table 2), this observation indicated that the reduced number of granulocytes in the peritoneum may be due to decreased numbers of cells migrating from the peripheral blood. The increased numbers of macrophages, despite the reduced numbers of monocytes in the peripheral blood, indicated an increased diapedesis, although increased tissue survival or local proliferation are possible alternative explanations.

Figure 26:
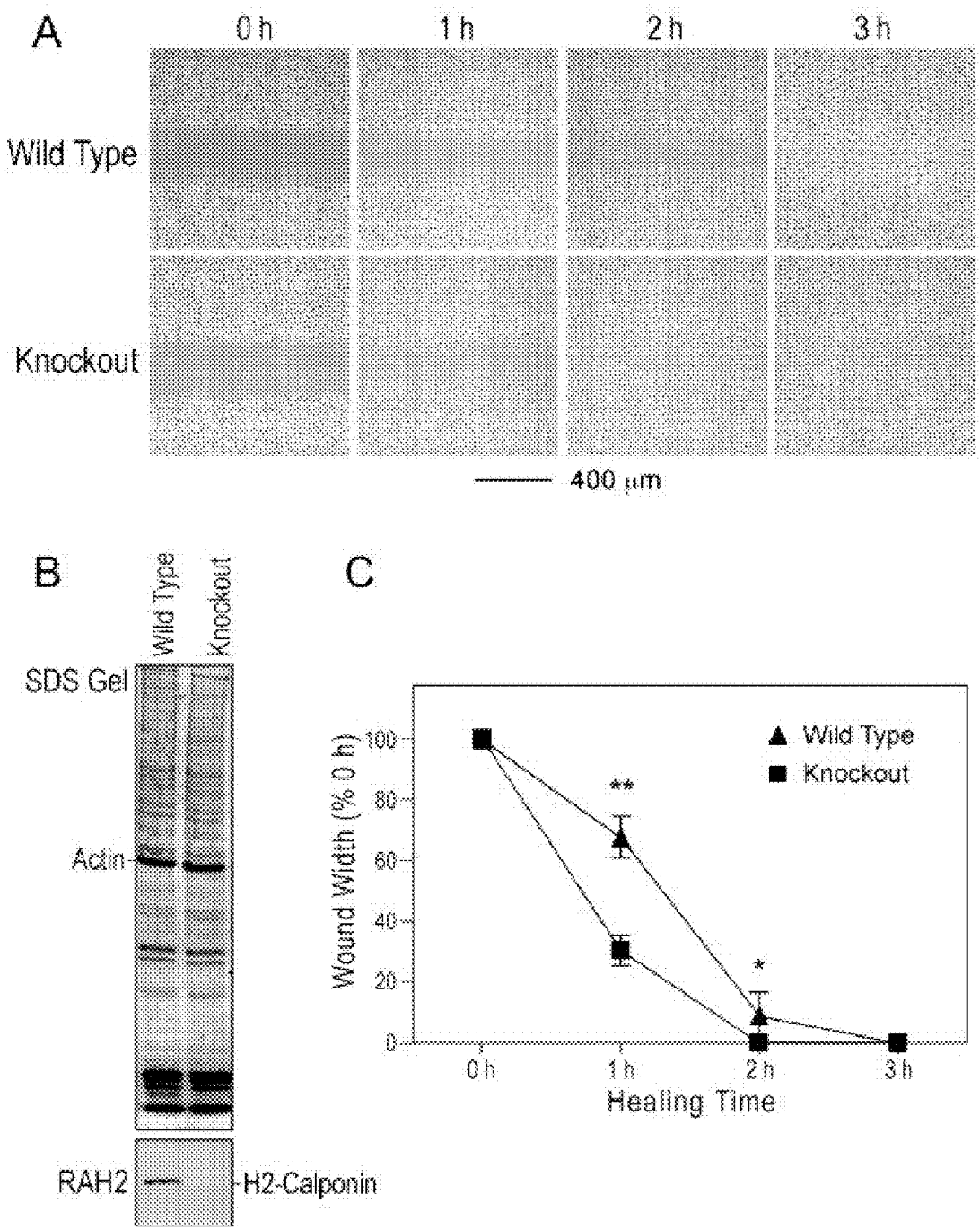
FIG. 26. Faster migration of h2-calponin-free macrophages during in vitro wound healing. (A) Scratch wounds were made in monolayer cultures of peritoneal residential macrophage 24 hr after plating. Healing of the wound by cell migration was monitored for 6 hours. The micrographs showed an earlier closure of the wound in the h2-calponin-free macrophage culture than in the wild type control. (B) SDS-PAGE and Western blot using the anti-h2-calponin antibody RAH2 on total protein extracts from the cells collected at the end of the wound healing experiment confirmed the presence and absence of h2-calponin in the wild-type and Cnn2-knockout cells, respectively. (C) Quantification of the wound healing data demonstrated a faster migration rate for the h2-calponin knockout macrophages than for the wild-type control cells. *P<0.05, **P<0.01.

The intrinsic motility of h2-calponin-free macrophages in the absence of chemotactic stimulation was also examined. An in vitro wound healing assay using monolayer cells provides direct measurement of the rate of two-dimensional cell migration. The results from testing cultures of mouse peritoneal residential macrophages showed a significantly earlier closure of the scratch wound in h2-calponin-free cells versus the wild-type control (FIG. 26). This result is consistent with a faster migration rate for h2-calponin-free macrophages relative to wild-type controls, and the result is consistent with h2-calponin's function as an inhibitor of the motility of macrophages. Therefore, the increased diapedesis of h2-calponin-free myeloid cells is correlated to the function of the actin cytoskeleton. The data demonstrated a role for h2-calponin in regulating macrophage motility that plays an essential role in immune responses.

Because macrophages could proliferate in tissues (43) and h2-calponin is known to inhibit cell proliferation (18), the effect of h2-calponin on macrophage proliferation was investigated. Considering that peritoneal macrophages isolated from mice may not represent a uniform proliferating population, macrophage cell lines were preferred in this investigation. RAW264.7 is an extensively studied mouse macrophage cell line (34). In contrast to freshly isolated macrophages, the RAW264.7 cell line does not express endogenous h2-calponin (FIG. 27A). Therefore, RAW264.7 cells stably transfected with sense or anti-sense h2-calponin cDNA expression constructs were examined. The expression of h2-calponin in sense h2-calponin cDNA transfected cells significantly inhibited the rate of cell proliferation whereas the anti-sense cDNA control maintained a proliferation rate similar to that of the untransfected cells (FIG. 27B).

Figure 28:
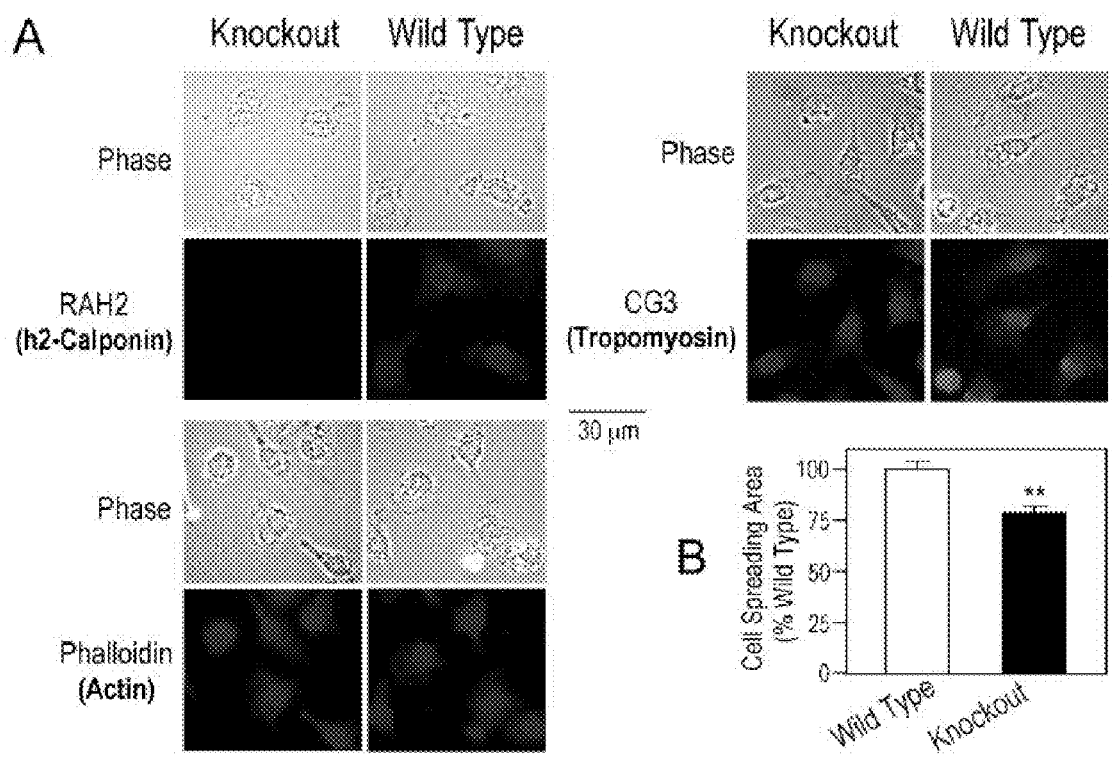
FIG. 28. Loss of h2-calponin in macrophages reduced cell spreading area in adhesion cultures. (A) Immunofluorescence microscopy using anti-h2-calponin RAH2 and anti-tropomyosin CG3 antibodies followed by TRITC-conjugated second antibody and TRITCphalloidin staining of F-actin revealed the cellular localization of h2-calponin in macrophages and the effect of h2-calponin loss on the actin cytoskeleton. The phase-contrast and fluorescence images indicated that the h2-calponin-free macrophages had a smaller spreading area, although the structure of actin cytoskeleton was not significantly altered. (B) The reduced spreading area of h2-calponin-free macrophages in adherent culture was quantified using the NIH Image software version 1.61. **P<0.01.

To investigate the mechanisms involved in the function of h2-calponin in regulating macrophage function, the cell morphology and actin cytoskeleton structure of h2-calponin-free mouse macrophages were analyzed. The phase-contrast and immunofluorescence micrographs in FIG. 28A demonstrate that the h2-calponin-free macrophages have a reduced spreading area compared to wild-type cells in adherent culture (FIG. 28B), with apparently normal structure for the actin stress fibers. The cell spreading in adhesion culture reflects cell adhesion to the substrate as well as the mechanical force generated in the cytoskeleton (44). Because h2-calponin was known to increase the stability of actin filaments (3), the reduced spreading of h2-calponin-free macrophages indicated a role for h2-calponin in macrophage adhesion as well as the control of cytoskeleton dynamics.

Figure 29:
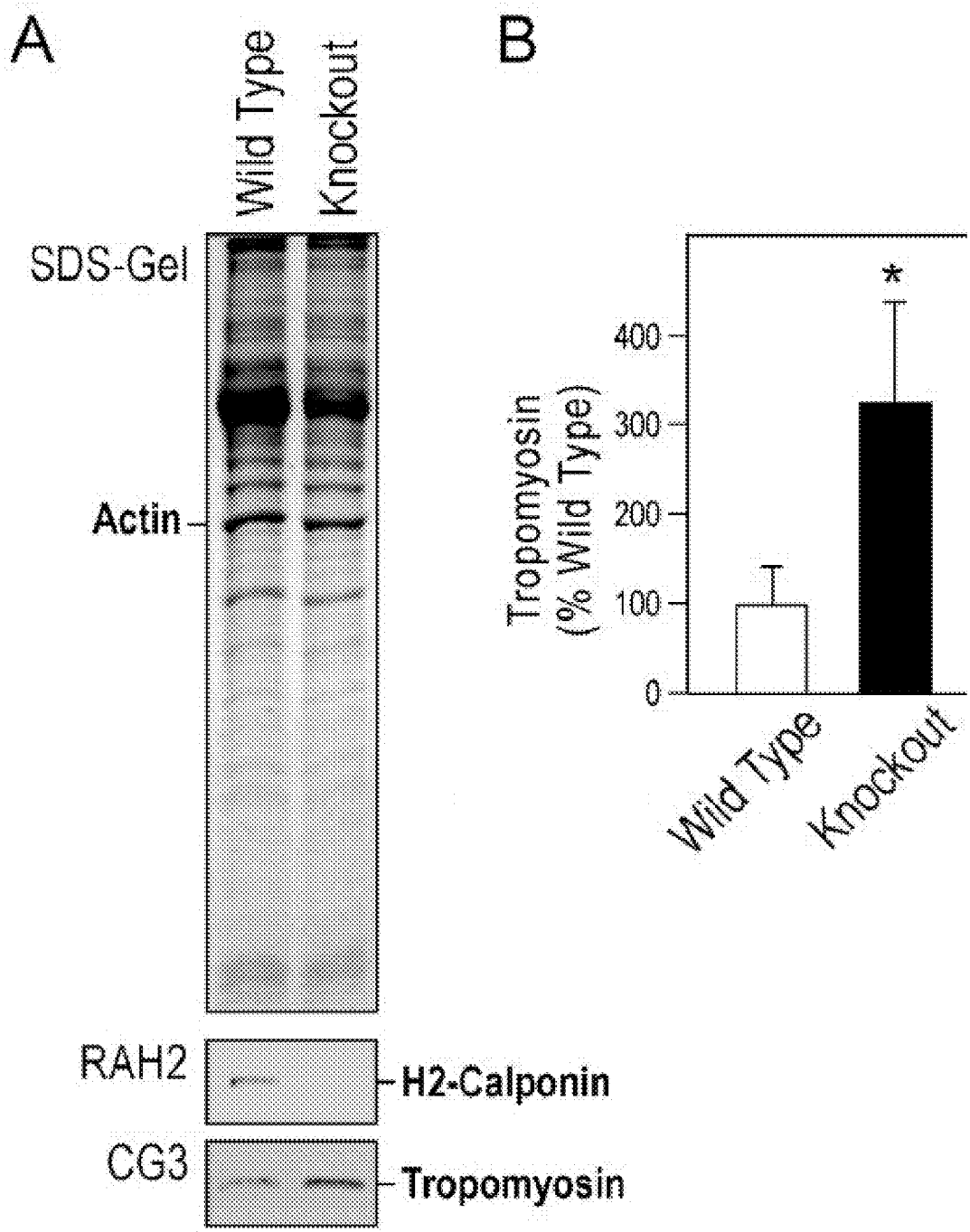
FIG. 29. Increase in the amount of tropomyosin in h2-calponin-free macrophages. (A) SDS-PAGE and Western blots showed a higher level of tropomyosin versus actin in the h2-calponin-free macrophages than that in wild type cells. (B) The difference was quantified by densitometry (P<0.001).

It was known that macrophages express only low molecular weight tropomyosin (45). Consistently, nonmuscle tropomyosin isoform 5 (Tm5) (46) was detected in both wild-type and h2-calponin-free macrophages by mAb CG3 (FIG. 29A). No high molecular weight tropomyosin isoforms were detectable. H2-calponin-free macrophages showed a higher level of Tm5 than that in the wild-type cells (FIG. 29B). This change might be a cellular response to the loss of h2-calponin in attempting to maintain the function of tropomyosin, a protein known to stabilize actin filaments in non-muscle cells (46).

Figure 30:
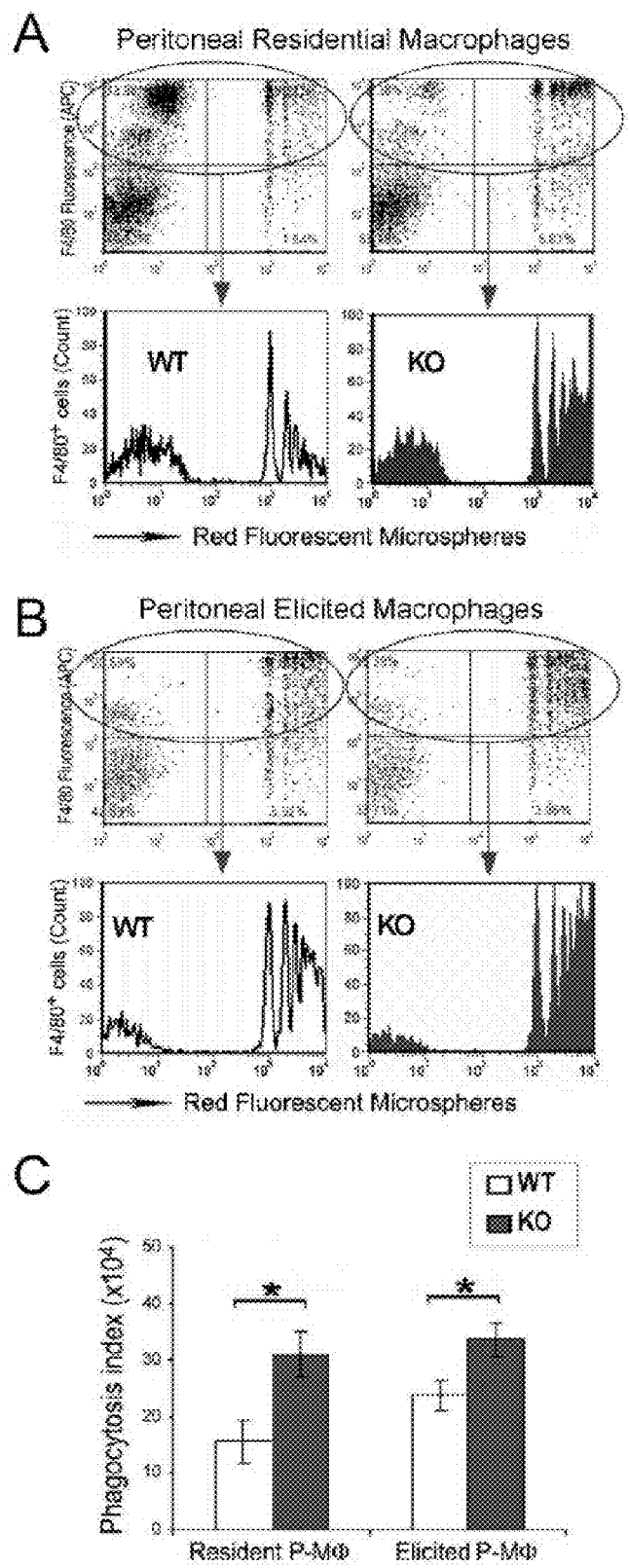
FIG. 30. H2-calponin-free macrophages had enhanced phagocytosis. Residential (A) and elicited (B) peritoneal cells isolated from h2-calponin knockout (KO) and wild type (WT) mice were incubated with red-fluorescent carboxyl microspheres to assess phagocytosis activity. In the representative flow cytometric histograms of the F4/80-positive WT and KO macrophages, the x-axis represents the fluorescent intensity indicating phagocytosis of the beads and the y-axis represents relative cell counts. The peaks from left to right represent cell populations with no bead-ingested, 1 beads-ingested, and 2 to more than 5 beads-ingested. (C) The phagocytosis activities measured on peritoneal residential (n=7 for both WT and KO) and 72 hour-elicited (n=7 for WT, n=5 for KO) macrophages are summarized as phagocytosis index (percent of cells containing fluorescent beads X mean florescence intensity of cells containing beads). The data demonstrate an enhanced phagocytosis activity of both residential and elicited macrophages when h2-calponin was absent (*P<0.05).

The phagocytosis function of h2-calponin-free macrophages was also examined in vitro using latex beads. The results demonstrated that the lack of h2-calponin resulted in enhanced phagocytic activity of both residential (FIG. 30A) and 72 hour-elicited (FIG. 30B) mouse peritoneal macrophages. In contrast, h2-calponin-free and wild-type granulocytes showed no difference in phagocytotic activity. The increased phagocytosis activity of h2-calponin-free macrophages is consistent with a more active actin cytoskeleton function, consistent with the results of the cell motility studies.

The results disclosed herein establish for the first time the high level expression of h2-calponin in the monocyte-granulocyte lineage of myeloid cells, with an up-regulation during monocyte to macrophage differentiation. To understand the function of h2-calponin in the regulation of myeloid cell motility, we constructed h2-calponin gene-targeted mice and examined the effects of h2-calponin deficiency on the function of macrophages.

The finding of high levels of h2-calponin expression in myeloid cells, but not in T and B lymphocytes (FIG. 21), indicated a role in a unique function of myeloid cells. While the h2-calponin expression was dependent on the differentiation of granulocytes, further up-regulation of h2-calponin expression occurred during the differentiation of peripheral blood monocytes into macrophages (FIGS. 21 and 22). Monocytes and macrophages are extremely dynamic cells with intensive membrane trafficking, fusion and fission. The actin cytoskeleton plays a central role in macrophage locomotion, phagocytosis and endocytosis (47), and change in cell shape required for transmigration (1). Considering that h2-calponin is an inhibitor in balancing actin function (9), the differential expression of h2-calponin in different leukocytes is consistent with the cytoskeleton activities of these various cells. For example, the increased h2-calponin inhibition in macrophages may correspond to its reduced mobility versus that in monocytes (42).

It is commonly observed that the differentiation of monocytes into macrophages in culture is dependent on adhesion to the culture dish (48). The expression of h2-calponin is dependent on the tension built in the actin cytoskeleton against the stiffness of the cultural substrate (3). In the studies disclosed herein, an increase in h2-calponin expression during adhesion-dependent differentiation of monocytes into mature macrophages was found (FIG. 22). This correlation indicated that the attachment of monocytes to the substrate increased cytoskeleton tension and, thereby, up-regulated the expression of h2-calponin. The early dip of h2-calponin level after monocyte adhesion to the culture dish (FIG. 22) indicated a lag between the cell adhesion and h2-calponin up-regulation, which may correspond to the transendothelial migration of monocytes after in vivo attachment to the vascular wall (49).

The association of h2-calponin regulation and function to the substrate adherence-dependent differentiation of monocytes into mature macrophages is a novel finding. Considering that calponin plays an inhibitory role in the regulation of cell motility, the upregulation of h2-calponin expression during monocyte-macrophage differentiation may reflect a need for more active regulation for the more dynamic activity of the actin filaments than is required for macrophage functions. In addition, data disclosed herein establishes that increased h2-calponin expression in mature macrophage is associated with reduced motility compared with that of monocyte (42). In other words, a sufficiently high level of h2-calponin in macrophages is expected to be a critical factor that balances the function of macrophages to maintain physiological levels of activity critical to immunological defenses.

Figure 27:
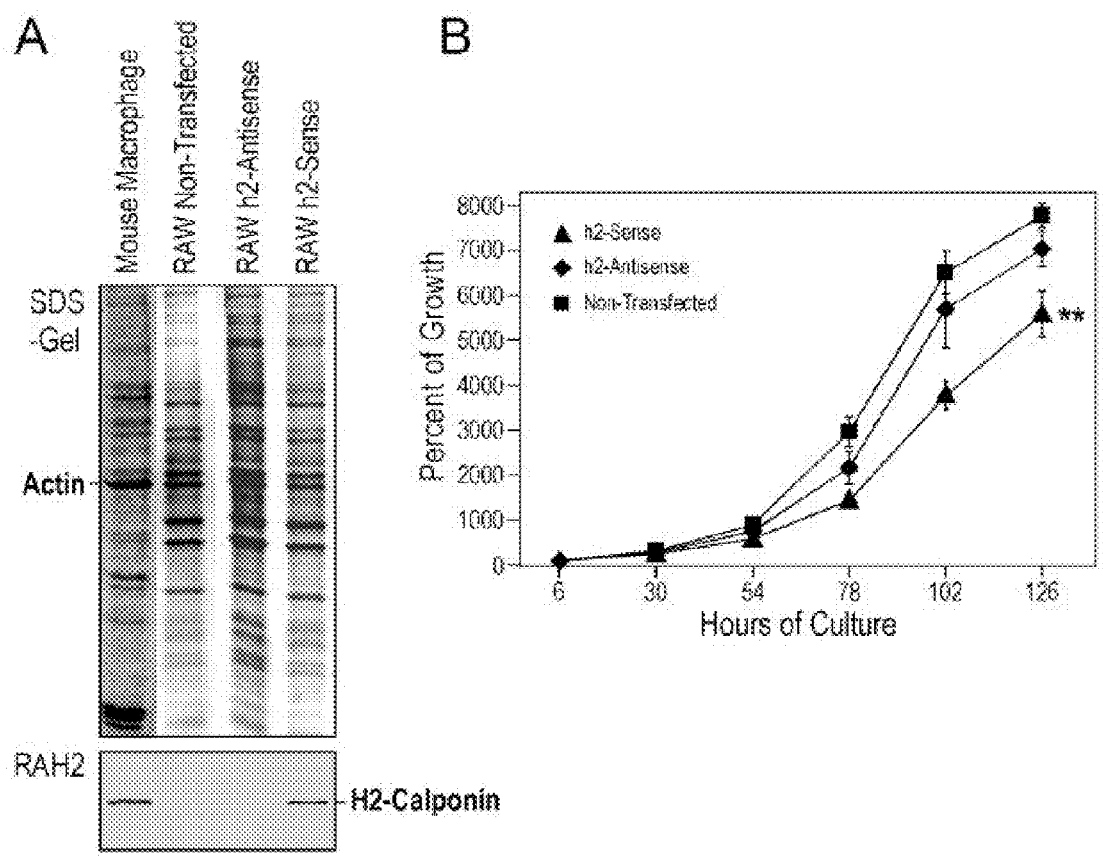
FIG. 27. Transfective expression of h2-calponin in RAW cells inhibited cell proliferation. (A) The Western blots showed that the RAW264.7 mouse macrophage line had lost endogenous h2-calponin expression, in contrast to mouse primary peritoneal macrophages. Stable transfective expression of mouse h2-calponin cDNA under the CMV promoter produced a significant level of h2-calponin. (B) RAW264.7 cells stable-transfected with sense or antisense h2-calponin cDNA expression vectors as well as non-transfected controls were examined for the rate of cell proliferation by Crystal Violet staining. The cell proliferation curves summarized from four experiments demonstrated a significant decrease in the h2-calponin sense cDNA transfected cells in comparison to that of the antisense transfected and non-transfected RAW cells (**P<0.001). The slightly lower proliferation rate of the antisense cDNA transfected cells than that of the non-transfected cells reflected the effect of G418 in the culture of the transfected cells.

Forced expression of h2-calponin inhibited the proliferation rate of smooth muscle cells (18). Because macrophages are normally postmitotic cells and are not suitable for in vitro proliferation studies, a RAW cell line that has lost the expression of endogenous h2-calponin was used to study the effect of h2-calponin on myeloid cell proliferation. The results demonstrated that, consistent with the observation from smooth muscle cell studies, forced expression of h2-calponin significantly decreased the proliferation rate of RAW cells (FIG. 27). Together with its effect on inhibiting macrophage migration (FIG. 26) and phagocytosis (FIG. 30), these results demonstrate that h2-calponin plays a potent role in regulating macrophage function by acting also in cell proliferation during the activation of macrophage responses.

The volume of actin cytoskeleton increases during monocyte-macrophage differentiation, as shown by the significantly lower amount of histone detected in SDS-gels in which the loadings were normalized by the amount of actin (FIG. 22A). This observation is consistent with the notion that the actin cytoskeleton is a critical component in the function of mature macrophages. The data disclosed herein establishes that removal or addition of h2-calponin can alter the proliferation, migration and phagocytosis of macrophages, identifying calponin-mediated inhibition of actin cytoskeleton activity as a target for controlling macrophage function. For example, enhancing h2-calponin's inhibitory function is expected to provide a treatment for autoimmune diseases, whereas reducing the inhibition is expected to strengthen immune defenses. H2-calponin gene expression and protein turnover are both regulated by mechanical tension built in the actin cytoskeleton by a myosin II motor dependent on the mechanical stiffness of the substrates (3,4). On the other hand, h2-calponin is known to increase the stability of actin filaments (3). Therefore, the lack of h2-calponin in macrophages may make the actin cytoskeleton more dynamic, consistent with the finding that the lack of h2-calponin increases macrophage migration and phagocytosis. Further, it is expected that constitutive expression of h2-calponin or preventing h2-calponin degradation to increase the inhibition on actin-based cell motility will be able to suppress macrophage function in the treatment of autoimmune diseases.

The lack of h2-calponin in macrophages did not alter the apparent structure of actin filaments in cultured monolayer cells (FIG. 28A), similar to that seen in the SM3 smooth muscle cell line lacking endogenous calponin (18) and fibroblasts from Cnn2 knockout mice. Tropomyosin is an actin filament associated protein highly conserved through evolution (46). Multiple isoforms of tropomyosin are present in non-muscle cells. A switching from high molecular weight to low molecular weight tropomyosin isoforms in tumor cells indicated a functional significance for the isoforms in cellular phenotypes (50). It has been reported that macrophage cells intrinsically lack the high molecular weight tropomyosin isoforms, presumably related to the high mobility of macrophages (45). The change in the level of tropomyosin in h2-calponin-free macrophages (FIG. 29) implicates regulation of tropomyosin levels in the mechanism by which h2-calponin regulates macrophage cell motility.

CMV promoter-directed over-expression of h2-calponin in a smooth muscle cell line that lacks endogenous calponin increased the level of tropomyosin corresponding to increased stability of the actin cytoskeleton (3). Therefore, h2-calponin is expected to play a role together with tropomyosin in the regulation of the actin cytoskeleton. However, tropomyosin in h2-calponin-free macrophages did not decrease but increased (FIG. 29B). This result indicates that in the absence of h2-calponin, increased tropomyosin expression might be activated by cellular mechanisms as an attempt to stabilize the actin cytoskeleton. This observation supports the view that h2-calponin functions together with tropomyosin in regulating the non-muscle cytoskeleton.

The experiments disclosed herein reveal high levels of h2-calponin in myeloid cells. Functional characterization of macrophages from h2-calponin knockout mice as well as transfected RAW cells showed a role of h2-calponin in inhibiting myeloid cell proliferation, migration, and phagocytosis. The role of h2-calponin in the function of monocytes, macrophages and neutrophils demonstrates a downstream mechanism in the regulation of myeloid cell activity in immune responses via the function of the actin cytoskeleton. In addition, a representative mobile non-muscle cell system provided novel information for the role of calponin in regulating non-muscle cell motility that has broad physiological and pathological significance.

REFERENCES

1. Jones G E. Cellular signaling in macrophage migration and chemotaxis. J Leukoc Biol. 2000; 68: 593-602.
2. Takahashi, K., Hiwada, K., and Kobuku, T. Isolation and characterization of a 34,000-dalton calmodulin- and F-actin-binding protein from chicken gizzard smooth muscle. Biochem. Biophys. Res. Commun. 1986; 141: 20-26.
3. Hossain, M. M., Crish, J. F., Eckert R. L., Lin, J. J.-C., and Jin, J.-P. H2-calponin is regulated by mechanical tension and modifies the function of actin cytoskeleton. J. Biol. Chem. 2005; 280: 42442-53.
4. Hossain, M. M., Smith, P. G., Wu, K., and Jin, J.-P. Cytoskeletal tension regulates both expression and degradation of h2-calponin in lung alveolar cells. Biochemistry 2006; 45: 15670-83.
5. Winder, S., and Walsh, M. P. Smooth muscle calponin: Inhibition of actomyosin MgATPase and regulation by phosphorylation. J. Biol. Chem. 1990; 265: 10148-10155.
6. Abe, M., Takahashi, K., and Hiwada, K. Effect of calponin on actin-activated myosin ATPase activity. J. Biochem. 1990; 108: 835-838.
7. Horiuchi, K. Y., and Chacko, S. The mechanism for the inhibition of actin-activated ATPase of smooth muscle heavy meromyosin by calponin. Biochem. Biophys. Res. Comm. 1991; 176:1487-1493.
8. Winder, S. J., Allen, B. G., Fraser, E. D., Kang, H.-M., Kargacin, G. J., and Walsh, M. P. Calponin phosphorylation in vitro and in intact muscle. Biochem. J. 1993; 296: 827-836.
9. Walsh, M. P. Calcium-dependent mechanisms of regulation of smooth muscle contraction. Biochem. Cell. Biol. 1991; 69: 771-800.
10. Shirinsky, V. P., Birynkov, K. G., Hettasch, J. M., and Sellers, J. R. Inhibition of the relative movement of actin and myosin by caldesmon and calponin. J. Biol. Chem. 1992; 267: 15886-15892.
11. Haeberle, J. R. Calponin decreases the rate of cross-bridge cycling and increases maximum force production by smooth muscle myosin in an in vitro motility assay. J. Biol. Chem. 1994; 269: 12424-12431.
12. Allen, B. G., & Walsh, M. P. The biochemical basis of the regulation of smooth muscle contraction. Trends Biochem. Sci. 1994; 19: 362-368.
13. Takahashi, K., and Nadal-Ginard, B. Molecular cloning and sequence analysis of smooth muscle calponin. J. Biol. Chem. 1991; 266:13284-13288.
14. Nishida, W., Kitami, Y., and Hiwada, K. cDNA cloning and mRNA expression of calponin and SM22 in rat aorta smooth muscle cells. Gene 1993; 130: 297-302.
15. Strasser, P., Gimona, M., Moessler, H., Herzog, M., and Small J. V. Mammalian calponin. Identification and expression of genetic variants. FEBS Lett. 1993; 330: 13-18.
16. Applegate, D., Feng, W., Green, R. S., and Taubman, M. B. Cloning and expression of a novel acidic calponin isoform from rat aortic vascular smooth muscle. J. Biol. Chem. 1994; 269: 10683-10690.
17. Trabelsi-Terzidis, H., Fattoum, A., Represa, A., Dessi, F., Ben-Ari, Y., and der Terrossian, E. Expression of an acidic isoform of calponin in rat brain: Western blots on one- or two-dimensional gels and immunolocalization in cultured cells. Biochem. J. 1995; 306: 211-215.
18. Hossain, M. M., Hwang, D.-Y., Huang, Q.-Q., Sasaki, Y., and Jin, J.-P. Developmentally regulated expression of calponin isoforms and the effect of h2-calponin on cell proliferation. Am. J. Physiol.:Cell Physiol. 2003; 284:C156-C167.
19. Thomas, K. R., and Capecchi, M. R. Site-directed mutagenesis by gene targeting in mouse embryo-derived stem cells. Cell 1987; 51: 503-512.
20. Gao, J., Hwang, J. M., and Jin, J.-P. Complete nucleotide sequence, structural organization and an alternatively spliced exon of mouse h1-calponin gene. Biochem Biophys. Res. Commun. 1996; 218: 292-297.
21. Huang, Q.-Q., Chen, A., and Jin, J.-P. Genomic sequence and structural organization of mouse slow skeletal muscle troponin T gene. Gene 19991; 229: 1-10.
22. Conrad M, Brielmeier M, Wurst W, Bomkamm G W. Optimized vector for conditional gene targeting in mouse embryonic stem cells. Biotechniques. 2003; 34: 1136-8, 1140.
23. Meyers, E N, Lewandoski M, Martin G R. An Fgf8 mutant allelic series generated by Cre- and Flp-mediated recombination. Nat. Genet. 1998; 18: 136-41.
24. Nigam, R., Triggle, C. R., and Jin, J.-P. Smooth muscle calponin is not essential to but may modulate the norepinephrine- or sodium fluoride-induced contraction of rat aorta. J. Muscle Res. Cell Motil. 1998; 19: 695-703.
25. Jin, J.-P., Walsh, M. P., Resek, M. E., and McMartin, G. A. Epitope structure and expression of calponin in different smooth muscles and during development. Biochem. Cell Biol. 1996; 74: 187-196.
26. Lin J J-C, Chou, C-S and Lin J L-C. Monoclonal antibodies against chicken tropomyosin isoforms: production, characterization, and application. Hybridoma 1985; 4: 223-242.
27. Huang Q.-Q, Ma Y Y, Adebayo A., and Pope R M. Increased Macrophage activation mediated through Toll-Like receptors in Rheumatoid Arthritis. Arthritis Rheum. 2007; 56: 2192-201.

28. Liu, H., H. Perlman, L. J. Pagliari, and R. M. Pope. Constitutively Activated Akt-1 Is Vital for the Survival of Human Monocyte-differentiated Macrophages. Role of mcl-1, independent of nuclear factor (nf)-kappab, bad, or caspase activation. J Exp Med 2001; 194: 113-126.

29. Liu, H., Y. Ma, S. M. Cole, C. Zander, K. H. Chen, J. Karras, and R. M. Pope. Serine phosphorylation of STAT3 is essential for Mcl-1 expression and macrophage survival. Blood 2003; 102: 344-352.

30. Liu, H., P. Eksarko, V. Temkin, G. K. Haines, 3rd, H. Perlman, A. E. Koch, B. Thimmapaya, and R. M. Pope. Mcl-1 is essential for the survival of synovial fibroblasts in rheumatoid arthritis. J Immunol 2005; 175: 8337-8345.

31. Ma, Y., H. Liu, H. Tu-Rapp, H. J. Thiesen, S. M. Ibrahim, S. M. Cole, and R. M. Pope. Fas ligation on macrophages enhances IL-1R1-Toll-like receptor 4 signaling and promotes chronic inflammation. Nat Immunol. 2004; 5, 380-7

32. Pagliari, L. J., Perlman, H., Liu, H. and Pope, R. M. Macrophages Require Constitutive N FkappaB Activation to Maintain A1 Expression and Mitochondrial Homeostasis. Mol. Cell. Biol. 2000; 20: 8855-8865.

33. Perlman, H., L. J. Pagliari, C. Georganas, T. Mano, K. Walsh, and R. M. Pope. (1999) FLICE-inhibitory protein expression during macrophage differentiation confers resistance to fas-mediated apoptosis. J. Exp. Med. 1999; 190: 1679-1688.

34. Raschke W C, Baird S, Ralph P, Nakoinz I. Functional macrophage cell lines transformed by Abelson leukemia virus. Cell 1978; 15: 261-267.

35. Oda, T., and Maeda, H. A new simple fluorometric assay for phagocytosis. J. Immunol. Methods 1986; 88: 175-183.

36. Ichinose M, Asai M, Imai K, Sawada M. Enhancement of phagocytosis in mouse macrophages by pituitary adenylate cyclase activating polypeptide (PACAP) and related peptides. Immunopharmacology. 1995; 30: 217-24.

37. Scott R S, McMahon E J, Pop S M, Reap E A, Caricchio R, Cohen P L, Earp H S and Matsushima G K. Phagocytosis and clearance of apoptotic cells is mediated by MER. Nature 2001; 411, 207-11.

38. Aziz A, Vanhille L, Mohideen P, Kelly L M, Otto C, Bakri Y, Mossadegh N, Sarrazin S, Sieweke M H. Development of macrophages with altered actin organization in the absence of MafB. Mol Cell Biol. 2006; 26: 6808-18.

39. Collins S J, Ruscetti F W, Gallagher R E, Gallo R C. Terminal differentiation of human promyelocytic leukemia cells induced by dimethyl sulfoxide and other polar compounds. Proc Natl Acad Sci USA. 1978; 75: 2458-62.

40. Le J, Reis L F, Vilcek J. Tumor necrosis factor and interleukin 1 can act as essential growth factors in a murine plasmacytoma line. Lymphokine Res. 1988; 7: 99-106.

41. Yeh M Y, Hellström I, Brown J P, Warner G A, Hansen J A, Hellström K E. Cell surface antigens of human melanoma identified by monoclonal antibody. Proc Natl Acad Sci USA. 1979; 76: 2927-31.

42. Tacke F, Randolph G J. Migratory fate and differentiation of blood monocyte subsets. Immunobiology. 2006; 211: 609-18.

43. Gordon, S. The macrophage: Past, present and future. Eur. J. Immunol. 2007; 37: S9-S17. 44. Discher, D. E., Jammey, P., and Wang, Y. Tissue cells feel and respond to the stiffness of their substrate, Science 2005; 310, 1139-1143.

45. Nakamura Y, Sakiyama S, Takenaga K. Suppression of syntheses of high molecular weight nonmuscle tropomyosins in macrophages. Cell Motil Cytoskeleton. 1995; 31: 273-82.

46. Lin, J J, Warren K S, Wamboldt D D, Wang T, Lin J L. Tropomyosin isoforms in nonmuscle cells. Int Rev Cytol. 1997; 170:1-38.

47. Beningo, K. A., and Wang, Y. L. Fc-receptor-mediated phagocytosis is regulated by mechanical properties of the target. J. Cell Sci. 2002; 115, 849-856.

48. Liu, H., Bo, S., Huang, C.-C., Eksarko, P., Pope, R. M. Transcriptional diversity during monocyte to macrophage differentiation. Immunol. Lett. 2008; In press.

49. Ley K, Laudanna C, Cybulsky M I, Nourshargh S. Getting to the site of inflammation: the leukocyte adhesion cascade updated. Nat Rev Immunol. 2007; 7: 678-89.

50. Miyado K, Kimura M, Taniguchi S. Decreased expression of a single tropomyosin isoform, T M5/T M30 nm, results in reduction in motility of highly metastatic B16-F10 mouse melanoma cells. Biochem Biophys Res Commun. 1996; 225:427-35.

Each of the references cited herein is incorporated herein by reference in its entirety, including the incorporation by reference herein of specifically cited disclosures.

While the invention has been described in connection with specific embodiments thereof, it will be understood that it is capable of further modifications and this application is intended to cover any variations, uses, or adaptations of the invention following, in general, the principles of the invention and including such departures from the present disclosure as come within known or customary practice within the art to which the invention pertains and as may be applied to the essential features set forth herein and as follows in the scope of the appended claims.

I claim:

1. A method of screening for a modulator of h2-calponin activity comprising:
   (a) contacting isolated h2-calponin with a candidate modulator;
   (b) determining the activity of said h2-calponin in the presence and absence of said candidate modulator; and
   (c) identifying said candidate modulator as a modulator of h2-calponin if the activity of the isolated h2-calponin differs in the presence and absence of said candidate modulator.

2. The method according to claim 1 wherein the h2-calponin is produced recombinantly.

3. The method according to claim 1 wherein the modulator inhibits the activity of h2-calponin.

4. The method according to claim 3 wherein the modulator inhibits activity by inducing h2-calponin degradation.

5. The method according to claim 1 wherein the modulator increases the activity of h2-calponin.

6. The method according to claim 1 wherein the modulator is an anti-h2-calponin antibody.

7. A method of screening for a modulator of h2-calponin activity comprising:
   (a) contacting a sample expressing h2-calponin with a candidate modulator;
   (b) determining h2-calponin activity in the presence and absence of said candidate modulator; and
   (c) identifying said candidate modulator as a modulator of h2-calponin if the activity of h2-calponin in the sample differs in the presence and absence of said candidate modulator.

8. The method of claim 7 wherein the sample comprises a cell, tissue, cell extract, tissue extract, or isolated protein.

9. The method according to claim 8 wherein the cell is selected from the group consisting of an epidermal keratinocyte, a lung alveolar cell, a cornea epithelial cell, an endothelial cell, a kidney podocyte, an osteoblast, a fibroblast, a monocyte, a macrophage, a neutrophil, a myoblast, an embryonic stem cell and a cancer cell.

10. The method according to claim 9 wherein the cell is selected from the group consisting of a cornea epithelial cell, an endothelial cell, a kidney podocyte, an osteoblast, a monocyte, a macrophage, a neutrophil, a myoblast and an embryonic stem cell.

* * * * *

UNITED STATES PATENT AND TRADEMARK OFFICE
CERTIFICATE OF CORRECTION

| | | |
|---|---|---|
| PATENT NO. | : 8,048,636 B2 | Page 1 of 1 |
| APPLICATION NO. | : 12/043013 | |
| DATED | : November 1, 2011 | |
| INVENTOR(S) | : Jian-Ping Jin | |

It is certified that error appears in the above-identified patent and that said Letters Patent is hereby corrected as shown below:

Title Page:

Item (73), "Northshore University Healthsystem" should be -- Northshore University Healthsystem, Evanston, Illinois --.

Signed and Sealed this
Fourth Day of December, 2012

David J. Kappos
*Director of the United States Patent and Trademark Office*

SEQUENCE LISTING

```
<160> NUMBER OF SEQ ID NOS: 30

<210> SEQ ID NO 1
<211> LENGTH: 202
<212> TYPE: PRT
<213> ORGANISM: Homo sapiens

<400> SEQUENCE: 1

Met Ser Ser Thr Gln Phe Asn Lys Gly Pro Ser Tyr Gly Leu Ser Ala
1               5                   10                  15

Glu Val Lys Asn Arg Leu Leu Ser Lys Tyr Asp Pro Gln Lys Glu Ala
            20                  25                  30

Glu Leu Arg Thr Trp Ile Glu Gly Leu Thr Gly Leu Ser Ile Gly Pro
```

```
                    35                  40                  45
Asp Phe Gln Arg Gly Leu Lys Asp Gly Thr Ile Leu Cys Thr Leu Met
 50                  55                  60
Asn Lys Leu Gln Pro Gly Ser Val Pro Lys Ile Asn Arg Ser Met Gln
 65                  70                  75                  80
Asn Trp His Gln Leu Glu Asn Leu Ser Asn Phe Ile Lys Ala Met Val
                 85                  90                  95
Ser Tyr Gly Met Asn Pro Val Asp Leu Phe Glu Ala Asn Asp Leu Phe
                100                 105                 110
Glu Ser Gly Asn Met Thr Gln Val Gln Val Ser Leu Leu Ala Leu Ala
                115                 120                 125
Gly Lys Ala Lys Thr Lys Gly Leu Gln Ser Gly Val Asp Val Gly Val
            130                 135                 140
Lys Tyr Ser Glu Lys Gln Glu Arg Asn Phe Asp Asp Ala Thr Met Lys
145                 150                 155                 160
Ala Gly Gln Cys Gly Ile Gly Leu Gln Met Gly Thr Asn Lys Cys Ala
                165                 170                 175
Ser Gln Ser Gly Met His Leu Tyr Gly Thr Ala Gly Ile Ser Met Thr
                180                 185                 190
Pro Arg Thr Ile Ser Cys Pro Pro Trp Thr
                195                 200

<210> SEQ ID NO 2
<211> LENGTH: 608
<212> TYPE: DNA
<213> ORGANISM: Homo sapiens

<400> SEQUENCE: 2
gccatgagct ccacgcagtt caacaagggc ccctcgtacg ggctgtcggc cgaggtcaag     60
aaccggctcc tgtccaaata tgaccccag aaggaggcag agctccgcac ctggatcgag    120
ggactcaccg gcctctccat cggccccgac ttccagaggg gcctgaagga tggaactatc    180
ttatgcacac tcatgaacaa gctacagccg gctccgtcc ccaagatcaa ccgctccatg    240
cagaactggc accagctaga aaacctgtcc aacttcatca aggccatggt cagctacggc    300
atgaaccctg tggacctgtt cgaggccaac gacctgtttg agagtgggaa catgacgcag    360
gtgcaggtgt ctcttctcgc cctggcgggg aaggccaaga ctaaggggct gcagagcggg    420
gtggacgttg gcgtcaagta ctcggagaag caggagcgga atttcgacga tgccaccatg    480
aaggctggcc agtgcggcat cgggctgcag atgggcacca caaatgcgc cagccagtcg    540 ggcatgcacc tctacggcac agcaggcatc tctatgaccc caagaaccat atcctgcccc    600
ccatggac                                                            608

<210> SEQ ID NO 3
<211> LENGTH: 305
<212> TYPE: PRT
<213> ORGANISM: Mus musculus

<400> SEQUENCE: 3

Met Ser Ser Thr Gln Phe Asn Lys Gly Pro Ser Tyr Gly Leu Ser Ala
  1               5                  10                  15
Glu Val Lys Asn Arg Leu Leu Ser Lys Tyr Asp Pro Gln Lys Glu Ala
                 20                  25                  30
Glu Leu Arg Ser Trp Ile Glu Gly Leu Thr Gly Leu Ser Ile Gly Pro
             35                  40                  45
Asp Phe Gln Lys Gly Leu Lys Asp Gly Val Ile Leu Cys Thr Leu Met
```

```
                    50                  55                  60
Asn Lys Leu Gln Pro Gly Ser Val Pro Lys Ile Asn Arg Ser Met Gln
 65                  70                  75                  80

Asn Trp His Gln Leu Glu Asn Leu Ser Asn Phe Ile Lys Ala Met Val
                 85                  90                  95

Ser Tyr Gly Met Asn Pro Val Asp Leu Phe Glu Ala Asn Asp Leu Phe
                100                 105                 110

Glu Ser Gly Asn Met Thr Gln Val Gln Val Ser Leu Leu Ala Leu Ala
            115                 120                 125

Gly Lys Ala Lys Thr Lys Gly Leu Gln Ser Gly Val Asp Ile Gly Val
130                 135                 140

Lys Tyr Ser Glu Lys Gln Glu Arg Asn Phe Asp Asp Ala Thr Met Lys
145                 150                 155                 160

Ala Gly Gln Cys Val Ile Gly Leu Gln Met Gly Thr Asn Lys Cys Ala
                165                 170                 175

Ser Gln Ser Gly Met Thr Ala Tyr Gly Thr Arg Arg His Leu Tyr Asp
            180                 185                 190

Pro Lys Asn His Ile Leu Pro Pro Met Asp His Cys Thr Ile Ser Leu
            195                 200                 205

Gln Met Gly Thr Asn Lys Cys Ala Ser Gln Val Gly Met Thr Ala Pro
        210                 215                 220

Gly Thr Arg Arg His Ile Tyr Asp Thr Lys Leu Gly Thr Asp Lys Cys
225                 230                 235                 240

Asp Asn Ser Ser Met Ser Leu Gln Met Gly Tyr Thr Gln Gly Ala Asn
                245                 250                 255

Gln Ser Gly Gln Val Phe Gly Leu Gly Arg Gln Ile Tyr Asp Pro Lys
            260                 265                 270

Tyr Cys Pro Gln Gly Ser Ala Ala Asp Gly Ala Pro Ala Gly Asp Gly
        275                 280                 285

Gln Gly Glu Ala Pro Glu Tyr Leu Ala Tyr Cys Gln Glu Glu Ala Gly
    290                 295                 300

Tyr
305

<210> SEQ ID NO 4
<211> LENGTH: 1821
<212> TYPE: DNA
<213> ORGANISM: Mus musculus

<400> SEQUENCE: 4
gaattccgga tgggtcctga cacggccccc caggcccagg tactggtata tgagccccgc      60
cggtcccgct ggtcctcctg tcccgctccg gggtcccgcg ccatgagctc cacgcagttc     120
aacaagggcc cgtcctacgg gctctcggcc gaggtcaaga accggctcct gtccaaatat     180
gacccccaaa aggaagcaga actccgaagc tggatagagg actcacgggc ctctccatt      240 ggccctgact tccagaaggg tctgaaagat ggggttatcc tatgcacact catgaacaag     300
ctgcagccag gctccgtccc taaaatcaac cgctctatgc agaactggca ccagctagaa     360
aatctctcca acttcatcaa ggccatggtc agctacggca tgaaccctgt ggacctgttt     420
gaggccaatg acctgttcga gagcgggaac atgacacagg tgcaagtgtc tctgcttgca     480
ctggctggaa aggccaagac caaggggctg cagagtggtg tggacattgg agttaagtat     540
tcggagaaac aggagaggaa ctttgacgac gccaccatga aggccggcca gtgcgtcatc     600
gggctgcaga tggcaccaa caagtgtgcc agccagtctg gcatgacagc ctatggtacc     660
```

```
aggagacatc tctatgaccc caagaaccat atcctgcctc ccatggacca ctgcaccatc      720
agcctccaga tgggcaccaa caagtgtgcc agccaggtgg gcatgacagc tccagggacc      780
cggaggcaca tctatgacac caagctgggc accgacaagt gcgacaactc ttccatgtcc      840
ctgcagatgg gctacacgca gggcgccaac cagagcggtc aggtcttcgg actgggcgg       900 cagatctacg atcccaagta ttgcccacag ggctctgcag ctgacggggc tcctgcgggt      960
gacggccaag gcgaggcccc agagtacctg gcctactgcc aggaggaagc tggctactga     1020
gcacccagca tgccagctcc cccactgcat cagcagccct gtgtgggctt ggggttttc      1080 attgtgtttt gtgtttggaa actggtcatc tctttgtatc tctctctggc ctggaactca     1140
ctgcaatcct cctgcctcag cttcctaagg gctgggatga cagatctgtg ctatctatgc     1200
tccttcctca cccaccatgc ctcgcttcct tcccaggatt gacccaccag acaggggaca     1260
tgggtgtcct tggtgggaca gtgaggctgt gcgtttccca gtgggctgtg ggagaggctg     1320
gccccaatgg gcttcctgtt tcttcatctc tttcacatca gtttgtggtt tgtgaacccg     1380
gggaaattac aggcagtttc aatgaaagaa acaaggggt tttgtggggg ttttgcctca      1440
aaagtattgg agtacactag gctttaaaat actgcaggca ttctgaggga ctaagtttgc     1500
tttcccacga ctctcagact tcaccctcct gtgccccgtg ggaaactgag gcaagccaga     1560
tgtgacccca acgcctgcag ccctccctca ctcctctggt gtttgaaggc ttccctgccc     1620
ctgtgcaggc cctgattagg tgtgctagag tctgggcctc ggaaggggcc acacatgacc     1680
cacacgggcc cctgcactgc caggaaatgt gaaattccct gtgtggacca aaaaaacaaa     1740
aaaaaaaaac aaaaacaaaa caaaaacaaa aacaataaaa acctctgttt ctaagaaaaa     1800
aaaaaaaaaa aaccggaatt c                                               1821
```

<210> SEQ ID NO 5
<211> LENGTH: 296
<212> TYPE: PRT
<213> ORGANISM: Sus scrofa

<400> SEQUENCE: 5

```
Met Ser Ser Thr Gln Phe Asn Lys Gly Pro Ser Tyr Gly Leu Ser Ala
1               5                   10                  15

Glu Val Lys Asn Arg Leu Leu Ser Lys Tyr Asp Pro Gln Lys Glu Ala
            20                  25                  30

Glu Leu Arg Ser Trp Ile Glu Gly Leu Thr Gly Leu Ser Ile Gly Pro
        35                  40                  45

Asp Phe Gln Lys Gly Leu Lys Asp Gly Ile Ile Leu Cys Thr Leu Met
    50                  55                  60

Asn Lys Leu Gln Pro Gly Ser Val Pro Lys Ile Asn Arg Ser Met Gln
65                  70                  75                  80

Asn Trp His Gln Leu Glu Asn Leu Ser Asn Phe Ile Lys Ala Met Val
                85                  90                  95

Ser Tyr Gly Met Asn Pro Val Asp Leu Phe Glu Ala Asn Asp Leu Phe
            100                 105                 110

Glu Ser Gly Asn Met Thr Gln Val Gln Val Ser Leu Leu Ala Leu Ala
        115                 120                 125

Gly Lys Ala Lys Thr Lys Gly Leu Gln Ser Asp Val Asp Ile Gly Val
    130                 135                 140

Lys Tyr Ser Glu Lys Gln Gln Arg Asn Phe Asp Asp Ala Thr Met Lys
145                 150                 155                 160

Ala Gly Gln Cys Val Ile Gly Leu Gln Met Gly Thr Asn Lys Cys Ala
                165                 170                 175
```

```
Ser Gln Ser Gly Met Thr Ala Tyr Gly Thr Arg Arg His Leu Tyr Asp
            180                 185                 190

Pro Lys Asn His Ile Leu Pro Pro Met Asp His Ser Thr Ile Ser Leu
            195                 200                 205

Gln Met Gly Thr Asn Lys Cys Ala Ser Gln Val Gly Met Thr Ala Pro
            210                 215                 220

Gly Thr Arg Arg His Ile Tyr Asp Thr Lys Leu Gly Thr Asp Lys Cys
225                 230                 235                 240

Asp Asn Ser Ser Met Ser Leu Gln Met Gly Tyr Thr Gln Gly Ala Asn
                245                 250                 255

Gln Ser Gly Gln Val Phe Gly Leu Gly Arg Gln Ile Tyr Asp Pro Lys
            260                 265                 270

Tyr Cys Pro Gln Gly Pro Ala Ala Asp Gly Ala Pro Ala Ala Ala Gly
            275                 280                 285

Asp Cys Pro Gly Pro Gly Glu Ser
            290                 295

<210> SEQ ID NO 6
<211> LENGTH: 897
<212> TYPE: DNA
<213> ORGANISM: Sus scrofa

<400> SEQUENCE: 6
ccgccagcaa tgagctccac gcagttcaac aaggggccct cgtacgggct ctcggccgag     60
gtcaagaacc ggctcctgtc caaatacgac cctcagaagg aggcagagct ccgcagctgg    120
attgagggac ttactggcct gtccattggc cccgacttcc agaagggtct gaaggatggg    180
atcatcttgt gcacactcat gaataagctg cagccgggct cagtcccaa gatcaaccgc     240 tccatgcaga actggcacca gctagaaaac ctctccaact tcatcaaggc catggtcagc    300
tatggcatga accccgtgga cctgttcgaa gccaacgacc tgtttgagag tgggaacatg    360
acacaggtgc aagtgtctct tctcgccctg gctgggaagg ccaagacaaa ggggctgcag    420
agtgacgtgg acatcggcgt caagtactcg gagaagcagc agcggaactt tgacgatgcc    480
accatgaagg cgggccagtg cgtcatcggg ctgcagatgg gcaccaacaa atgtgccagc    540
cagtcgggca tgacggctta tggcaccaga aggcatctgt acgaccccaa gaaccatatc    600
ctgcccccca tggaccactc gaccatcagc ctccagatgg gcacaaacaa gtgtgccagc    660
caggtgggca tgactgctcc agggaccccgg cggcacatct acgacaccaa gctgggacta   720
gacaaatgtg acaattcctc catgtctctg cagatgggct acacacaggg cgccaaccag    780
agtggccagg ttttggcct gggcggcag atatatgacc ccaagtactg ccctcaaggc      840
ccggcagccg atggggctcc agcagctgct ggtgactgcc caggcctgg agagtct        897

<210> SEQ ID NO 7
<211> LENGTH: 297
<212> TYPE: PRT
<213> ORGANISM: Homo sapiens

<400> SEQUENCE: 7

Met Ser Ser Ala His Phe Asn Arg Gly Pro Ala Tyr Gly Leu Ser Ala
1               5                   10                  15

Glu Val Lys Asn Lys Leu Ala Gln Lys Tyr Asp His Gln Arg Glu Gln
            20                  25                  30

Glu Leu Arg Glu Trp Ile Glu Gly Val Thr Gly Arg Arg Ile Gly Asn
        35                  40                  45
```

```
Asn Phe Met Asp Gly Leu Lys Asp Gly Ile Ile Leu Cys Glu Phe Ile
 50                  55                  60

Asn Lys Leu Gln Pro Gly Ser Val Lys Lys Ile Asn Glu Ser Thr Gln
 65                  70                  75                  80

Asn Trp His Gln Leu Glu Asn Ile Gly Asn Phe Ile Lys Ala Ile Thr
                 85                  90                  95

Lys Tyr Gly Val Lys Pro His Asp Ile Phe Glu Ala Asn Asp Leu Phe
                100                 105                 110

Glu Asn Thr Asn His Thr Gln Val Gln Ser Thr Leu Leu Ala Leu Ala
            115                 120                 125

Ser Met Ala Lys Thr Lys Gly Asn Lys Val Asn Val Gly Val Lys Tyr
130                 135                 140

Ala Glu Lys Gln Glu Arg Lys Phe Glu Pro Gly Lys Leu Arg Glu Gly
145                 150                 155                 160

Arg Asn Ile Ile Gly Leu Gln Met Gly Thr Asn Lys Phe Ala Ser Gln
                165                 170                 175

Gln Gly Met Thr Ala Tyr Gly Thr Arg Arg His Leu Tyr Asp Pro Lys
            180                 185                 190

Leu Gly Thr Asp Gln Pro Leu Asp Gln Ala Thr Ile Ser Leu Gln Met
            195                 200                 205

Gly Thr Asn Lys Gly Ala Ser Gln Ala Gly Met Thr Ala Pro Gly Thr
210                 215                 220

Lys Arg Gln Ile Phe Glu Pro Gly Leu Gly Met Glu His Cys Asp Thr
225                 230                 235                 240

Leu Asn Val Ser Leu Gln Met Gly Ser Asn Lys Gly Ala Ser Gln Arg
                245                 250                 255

Gly Met Thr Val Tyr Gly Leu Pro Arg Gln Val Tyr Asp Pro Lys Tyr
            260                 265                 270

Cys Leu Thr Pro Glu Tyr Pro Glu Leu Gly Glu Pro Ala His Asn His
            275                 280                 285

His Ala His Asn Tyr Tyr Asn Ser Ala
    290                 295

<210> SEQ ID NO 8
<211> LENGTH: 1599
<212> TYPE: DNA
<213> ORGANISM: Homo sapiens

<400> SEQUENCE: 8
ggcaggcccc tacagccaat ggaacggccc tggaagagac ccgggtcgcc tccggagctt    60
caaaaacatg tgaggaggga agagtgtgca gacggaactt cagccgctgc ctctgttctc   120
agcgtcagtg ccgccactgc ccccgccaga gccaccggc  cagcatgtcc tctgctcact   180
tcaaccgagg ccctgcctac gggctgtcag ccgaggttaa gaacaagctg cccagaagt    240
atgaccacca gcgggagcag gagctgagag agtggatcga gggggtgaca ggccgtcgca   300
tcggcaacaa cttcatggac ggcctcaaag atggcatcat tctttgcgaa ttcatcaata   360
agctgcagcc aggctccgtg aagaagatca atgagtcaac ccaaaattgg caccagctgg   420
agaacatcgg caacttcatc aaggccatca ccaagtatgg ggtgaagccc acgacatt    480
ttgaggccaa cgacctgttt gagaacacca ccatacaca ggtgcagtcc accctcctgg    540
ctttggccag catggcgaag acgaaaggaa acaaggtgaa cgtgggagtg aagtacgcag   600
agaagcagga gcgaaattc gagccgggga agctaagaga agggcggaac atcattgggc   660
tgcagatggg caccaacaag tttgccagcc agcagggcat gacggcctat ggcacccggc   720
```

```
gccacctcta cgaccccaag ctgggcacag accagcctct ggaccaggcg accatcagcc      780
tgcagatggg caccaacaaa ggagccagcc aggctggcat gactgcgcca gggaccaagc      840
ggcagatctt cgagccgggg ctgggcatgg agcactgcga cacgctcaat gtcagcctgc      900
agatgggcag caacaaggc gcctcgcagc ggggcatgac ggtgtatggg ctgccacgcc       960
aggtctacga ccccaagtac tgtctgactc ccgagtaccc agagctgggt gagcccgccc     1020
acaaccacca cgcacacaac tactacaatt ccgcctaggg ccacaaggcc ttccctgttt     1080
tccccccaag ggaggctgct gctgctcttg gctggaccca gccaggccca gccgaccccc     1140
tctccctgca tggcatcctc cagccccgt agaactcaac ctctacaggg ttagagtttg      1200
gagagagcag actggcgggg ggcccattgg ggggaagggg accctccgct ctgtagtgct     1260
acagggtcca acatagagcc gggtgtcccc aacagcgccc aaaggacgca ctgagcaacg     1320
ctattccagc tgtcccccca ctccctcaca agtgggtacc cccaggacca gaagctcccc    1380
cagcaaagcc cccagagccc aggctcggcc tgccccacc ccattcccgc agtgggagca      1440
aactgcatgc ccagagaccc agcggacaca cgcggtttgg tttgcagcga ctggcatact     1500
atgtggatgt gacagtggcg tttgtaatga gagcactttc ttttttttct atttcactgg     1560
agcacaataa atggctgtaa aatctcaaaa aaaaaaaaa                            1599
```

<210> SEQ ID NO 9
<211> LENGTH: 297
<212> TYPE: PRT
<213> ORGANISM: Mus musculus

<400> SEQUENCE: 9

```
Met Ser Ser Ala His Phe Asn Arg Gly Pro Ala Tyr Gly Leu Ser Ala
1               5                   10                  15

Glu Val Lys Asn Lys Leu Ala Gln Lys Tyr Asp His Gln Arg Glu Gln
                20                  25                  30

Glu Leu Arg Glu Trp Ile Glu Gly Val Thr Gly Arg Arg Ile Gly Asn
            35                  40                  45

Asn Phe Met Tyr Gly Leu Lys Asp Gly Ile Ile Leu Cys Glu Phe Ile
        50                  55                  60

Asn Lys Leu Gln Pro Gly Ser Val Lys Lys Val Asn Glu Ser Thr Gln
65                  70                  75                  80

Asn Trp His Gln Leu Glu Asn Ile Gly Asn Phe Ile Lys Ala Ile Thr
                85                  90                  95

Lys Tyr Gly Val Lys Pro His Asp Ile Phe Glu Ala Asn Asp Leu Phe
            100                 105                 110

Glu Asn Thr Asn His Thr Gln Val Gln Ser Thr Leu Leu Ala Leu Ala
        115                 120                 125

Ser Met Ala Lys Thr Lys Gly Asn Lys Val Asn Val Gly Val Lys Tyr
    130                 135                 140

Ala Glu Lys Gln Glu Arg Arg Phe Glu Pro Glu Lys Leu Arg Glu Gly
145                 150                 155                 160

Arg Asn Ile Ile Gly Leu Gln Met Gly Thr Asn Lys Phe Ala Ser Gln
                165                 170                 175

Gln Gly Met Thr Ala Tyr Gly Thr Arg Arg His Leu Tyr Asp Pro Lys
            180                 185                 190

Leu Gly Thr Asp Gln Pro Leu Asp Gln Ala Thr Ile Ser Leu Gln Met
        195                 200                 205

Gly Thr Asn Lys Gly Ala Ser Gln Ala Gly Met Thr Ala Pro Gly Thr
    210                 215                 220
```

```
Lys Arg Gln Ile Phe Glu Pro Gly Leu Gly Met Glu His Cys Asp Thr
225                 230                 235                 240

Leu Asn Val Ser Leu Gln Met Gly Ser Asn Lys Gly Ala Ser Gln Arg
            245                 250                 255

Gly Met Thr Val Tyr Gly Leu Pro Arg Gln Val Tyr Asp Pro Lys Tyr
        260                 265                 270

Cys Leu Asn Pro Glu Tyr Pro Glu Leu Ser Glu Pro Thr His Asn His
        275                 280                 285

His Pro His Asn Tyr Tyr Asn Ser Ala
        290                 295

<210> SEQ ID NO 10
<211> LENGTH: 2370
<212> TYPE: DNA
<213> ORGANISM: Mus musculus

<400> SEQUENCE: 10
```

| | | | | | |
|---|---|---|---|---|---|
| gagacggagg | ctcggctgcc | tgttgcgctt | gtctgtgtca | tctgcacctc | tgctttgcca | 60 |
| gagcccctg | gccagcatgt | cttctgcaca | ttttaaccga | ggtcctgcct | acggcttgtc | 120 |
| tgctgaagta | aagaacaagc | tggcccagaa | atacgaccat | cagcgggagc | aggagctgag | 180 |
| agagtggatt | gagggggtga | caggccggcg | catcgggaac | aacttcatgt | atggcctcaa | 240 |
| agacgggatc | attctttgcg | aatttatcaa | caagctgcag | ccgggttctg | tgaagaaggt | 300 |
| caatgagtca | actcagaact | ggcaccagct | ggagaacata | ggtaatttca | tcaaagccat | 360 |
| taccaagtat | ggggtgaaac | cccacgacat | ctttgaggcc | aacgaccgt | ttgaaaacac | 420 |
| caaccataca | caagttcagt | ccactctcct | ggctctggcc | agcatggcca | agacaaaagg | 480 |
| aaacaaagtc | aatgtgggag | tcaagtatgc | agagaaacaa | gagcggagat | tgagccgga | 540 |
| gaagttgaga | gaaggcagga | acatcattgg | actgcagatg | ggcaccaaca | gtttgccag | 600 |
| tcagcaggga | tgacggcct | acggtacacg | gcgtcacctc | tatgatccca | aactgggtac | 660 |
| agatcagcct | ctggaccagg | cgaccatcag | cctgcagatg | ggcaccaaca | agggtgccag | 720 |
| ccaggctggc | atgactgcac | caggcaccaa | gcggcagatc | tttgagccag | gtctgggcat | 780 |
| ggaacactgc | gacacactca | acgtcagctt | gcagatgggc | agcaacaagg | gggcctccca | 840 |
| gaggggcatg | acagtgtatg | gcttcctcg | ccaggtgtac | gatcccaagt | actgcctgaa | 900 |
| ccccgagtac | ccagagctga | gtgagcccac | ccacaatcac | cacccgcaca | actactacaa | 960 |
| ctctgcctag | ggcccccaa | ggggctggct | gctgctcttg | gctggaccca | gctggcccag | 1020 |
| ccaaccccat | ctcctgcatg | gcgtcctccc | agcccctgg | cacctgccta | tagggttacg | 1080 |
| gtttggggag | atgaggccga | gggggcaat | gggaagaagg | gggcccctca | tccctggagc | 1140 |
| tttcgcaggg | cccaacatag | aactgggtgt | ccccaacagt | gcccgaagga | agcactgagt | 1200 |
| tgagctgttt | cagctgcccc | cctttattcc | ctcacaagta | agtacctccc | agaaccagaa | 1260 |
| acccttccag | cgaagccccc | agaacccagg | cttggcctga | cccctgcccc | attcctgcga | 1320 |
| cgggagcaga | tgcatgcctg | gaaacgcagt | ggacacacgc | attttggttt | tgcagtgact | 1380 |
| ggtgtttgtg | gatgtgacag | cagcgttgt | aactcgaaca | cattctttc | tatttcactg | 1440 |
| gagcacaata | aatggctgtg | acatcattgg | agtcttgggg | ccagttgttt | aggagcatgg | 1500 |
| cttagataat | ctccatcctc | ccatatatgt | aggaggtata | catacccctcc | tatacacact | 1560 |
| aggatcagtg | agatggctca | gagctagtaa | atgcacttga | caccaatcaa | gtgcctttac | 1620 |
| ttatgacttg | agttcaatcc | ttgagaccca | catggccaga | agaataggt | ttctgcagta | 1680 |
| cccactgacc | tccacacaca | ggccatgtga | tacatacccct | tccttaaata | tgtatttaaa | 1740 |

```
aaaattaaat aaacctagac cttacaccac tacacaaggt gagcacatag caaatgccac    1800
atatatttta acaaaatgat caggagtgtc ttggggtggg aggggagggg cggcatccca    1860
gattgtgtgc atgcggtgtg cactggttct actgggccag gtaatgtacc taatattggc    1920
agagcagttg agtagctaac tttgggacat ggctttctct atatgcctgc cttgttctca    1980
gaggtctctc tctttttttct ccttaaaact gaatcccatg ggctggtgag atgtcacagc    2040
tgtaaaggtg tgttgtgtgt aattaagata cacacaacaa agttgtttgc tgccaagtct    2100
gacaactttg tgttcaaacc ccagttccta catgatgaag gaccaactcc attaaactgc    2160
cttccacctc ttgccacagc atgcatgcac ccatccacac tttattttt ttttggcttt    2220 ttgaggcagg atttgtgatg tgtttaatcc tggatggcct agaacttgct cttttgacca    2280
ggctggcctt gaactaacga agatctgcct acctctgttt cctgagtgcc gggactacca    2340
tcatccacta taaatgtct ttggaaaacg                                       2370
```

<210> SEQ ID NO 11
<211> LENGTH: 297
<212> TYPE: PRT
<213> ORGANISM: Sus scrofa

<400> SEQUENCE: 11

```
Met Ser Ser Ala His Phe Asn Arg Gly Pro Ala Tyr Gly Leu Ser Ala
1               5                   10                  15

Glu Val Lys Asn Lys Leu Ala Gln Lys Tyr Asp His Gln Gln Glu Gln
            20                  25                  30

Glu Leu Arg Glu Trp Ile Glu Gly Val Thr Gly Arg Arg Ile Gly Asn
        35                  40                  45

Asn Phe Met Asp Gly Leu Lys Asp Gly Ile Ile Leu Cys Glu Phe Ile
    50                  55                  60

Asn Lys Leu Gln Pro Gly Ser Val Lys Val Asn Glu Ser Thr Gln
65                  70                  75                  80

Asn Trp His Gln Leu Glu Asn Ile Gly Asn Phe Ile Lys Ala Ile Thr
                85                  90                  95

Lys Tyr Gly Val Lys Pro His Asp Ile Phe Glu Ala Asn Asp Leu Phe
            100                 105                 110

Glu Asn Thr Asn His Thr Gln Val Gln Ser Thr Leu Leu Ala Leu Ala
        115                 120                 125

Ser Met Ala Lys Thr Lys Gly Asn Lys Val Asn Val Gly Val Lys Tyr
    130                 135                 140

Ala Glu Lys Gln Glu Arg Lys Phe Glu Pro Glu Lys Leu Arg Glu Gly
145                 150                 155                 160

Arg Asn Ile Ile Gly Leu Gln Met Gly Thr Asn Lys Phe Ala Ser Gln
                165                 170                 175

Gln Gly Met Thr Ala Tyr Gly Thr Arg Arg His Leu Tyr Asp Pro Lys
            180                 185                 190

Leu Gly Thr Asp Gln Pro Leu Asp Gln Ala Thr Ile Ser Leu Gln Met
        195                 200                 205

Gly Thr Asn Lys Gly Ala Ser Gln Ala Gly Met Thr Ala Pro Gly Thr
    210                 215                 220

Lys Arg Gln Ile Phe Glu Pro Gly Leu Gly Met Glu His Cys Asp Thr
225                 230                 235                 240

Leu Asn Val Ser Leu Gln Met Gly Ser Asn Lys Gly Ala Ser Gln Arg
                245                 250                 255

Gly Met Thr Val Tyr Gly Leu Pro Arg Gln Val Tyr Asp Pro Lys Tyr
```

```
                260             265             270
Cys Leu Thr Pro Glu Tyr Pro Glu Leu Gly Glu Pro Ala His Asn His
            275                 280                 285

His Pro His Asn Tyr Tyr Asn Ser Ala
    290                 295

<210> SEQ ID NO 12
<211> LENGTH: 1470
<212> TYPE: DNA
<213> ORGANISM: Sus scrofa

<400> SEQUENCE: 12
gaattccagc ttcagctgct gccgccggct tcagcgcaca ctgccaccgc tgcccaccat      60
ccgccagcat gtcctctgct cacttcaacc gaggcccccg ctacgggctg tcggctgagg     120
tcaagaacaa gctggcccag aagtatgacc accagcagga gcaggagctt cgagagtgga     180 tcgaggggt gacagggcgc cgcatcggca caaacttcat ggacggcctc aaagatggca     240
tcattctttg cgagttcatc aataagctcc agccaggctc cgtgaagaag gtcaatgagt     300
ccacccagaa ctggcaccag ctggagaaca ttggcaactt catcaaggcc atcaccaagt     360
atggggtgaa gccccacgac atctttgaag ccaacgacct gttcgagaac accaaccaca     420
cacaagtgca gtccacgctc ctggccctgg ccagcatggc caagacgaaa gggaacaagg     480
tgaacgtggg agtgaaatat gcggagaagc aggaacggaa atttgagccg agaagctaa     540 gagaagggcg gaacatcatt gggctgcaga tgggcaccaa caagtttgcc agtcagcagg     600
gcatgacagc ctatggcacc cggcgccacc tctacgaccc caagctgggc acggaccagc     660
ccctggacca ggctaccatc agcctgcaga tgggcaccaa caagggagcc agccaggctg     720
gcatgaccgc tcccgggacc aagcggcaga tcttcgagcc ggggctgggc atggagcact     780
gtgacacgct caacgtcagc ctacagatgg cagcaacaa gggggcctcg cagcggggca     840
tgacggtgta tggactgccc cgccaagtct acgatcccaa gtactgcctg acgcctgagt     900
acccggagct gggcgaacct gcccacaacc accaccgca caactactac aactctgcct     960
agggtgctgg gcctcccacc ttcccccagg gaggctggct gctgctcttg gtgggcctgg    1020
cctggcctgc tgacccctc cccctgcatg gctcctccag cccctggca cctgcctaca    1080 gggttagtgt ttgtggggag cagactgggg aacctgtggg ggggaagggg gcacctccct    1140
ggagcactac gaggtccaac atggagctgg tgttcccaa cagcacccaa aggacgcact    1200
gagcaaagct accccgctgt cccccactcc ccacaggtgg gtccccccc cggaccagaa    1260 gccccccaa gcgaagcccc cagagcccac gtcgcgcctc ccccaccccc attcccgcag    1320
tgggagcaaa ctgcatgccc agagaccag aggacacacg cggtttggtt tgcagctggc    1380
ctatgggatg tgacagtggc gtttgtaacg cgagcacttt ctttttctac ttcactggag    1440
cacaataaat agctgtaaaa tcaggaattc                                    1470

<210> SEQ ID NO 13
<211> LENGTH: 297
<212> TYPE: PRT
<213> ORGANISM: Mus musculus

<400> SEQUENCE: 13

Met Ser Ser Ala His Phe Asn Arg Gly Pro Ala Tyr Gly Leu Ser Ala
1               5                   10                  15

Glu Val Lys Asn Lys Leu Ala Gln Lys Tyr Asp His Gln Arg Glu Gln
            20                  25                  30
```

```
Glu Leu Arg Glu Trp Ile Glu Gly Val Thr Gly Arg Ile Gly Asn
         35                  40                  45

Asn Phe Met Asp Gly Leu Lys Asp Gly Ile Ile Leu Cys Glu Phe Ile
 50                  55                  60

Asn Lys Leu Gln Pro Gly Ser Val Lys Val Asn Glu Ser Thr Gln
 65                  70                  75                  80

Asn Trp His Gln Leu Glu Asn Ile Gly Asn Phe Ile Lys Ala Ile Thr
                     85                  90                  95

Lys Tyr Gly Val Lys Pro His Asp Ile Phe Glu Ala Asn Asp Leu Phe
                    100                 105                 110

Glu Asn Thr Asn His Thr Gln Val Gln Ser Thr Leu Leu Ala Leu Ala
                    115                 120                 125

Ser Met Ala Lys Thr Lys Gly Asn Lys Val Asn Val Gly Val Lys Tyr
    130                 135                 140

Ala Glu Lys Gln Glu Arg Arg Phe Glu Pro Glu Lys Leu Arg Glu Gly
145                 150                 155                 160

Arg Asn Ile Ile Gly Leu Gln Met Gly Thr Asn Lys Phe Ala Ser Gln
                    165                 170                 175

Gln Gly Met Thr Ala Tyr Gly Thr Arg Arg His Leu Tyr Asp Pro Lys
                180                 185                 190

Leu Gly Thr Asp Gln Pro Leu Asp Gln Ala Thr Ile Ser Leu Gln Met
                195                 200                 205

Gly Thr Asn Lys Gly Ala Ser Gln Ala Gly Met Thr Ala Pro Gly Thr
    210                 215                 220

Lys Arg Gln Ile Phe Glu Pro Gly Leu Gly Met Glu His Cys Asp Thr
225                 230                 235                 240

Leu Asn Val Ser Leu Gln Met Gly Ser Asn Lys Gly Ala Ser Gln Arg
                245                 250                 255

Gly Met Thr Val Tyr Gly Leu Pro Arg Gln Val Tyr Asp Pro Lys Tyr
                260                 265                 270

Cys Leu Asn Pro Glu Tyr Pro Glu Leu Ser Glu Pro Thr His Asn His
                275                 280                 285

His Pro His Asn Tyr Tyr Asn Ser Ala
    290                 295

<210> SEQ ID NO 14
<211> LENGTH: 1524
<212> TYPE: DNA
<213> ORGANISM: Mus musculus

<400> SEQUENCE: 14
gaattccggg ggaagagggt gcagacggag gctcggctgc ctgttgcgct tgtctgtgtc      60
atctgcacct ctgctttgcc agagccccct ggccagcatg tcttctgcac attttaaccg     120
aggtcctgcc tacggcttgt ctgctgaagt aaagaacaag ctggcccaga aatacgacca     180
tcagcgggag caggagctga gagagtggat tgaggggggtg acaggccggc gcatcgggaa     240
caacttcatg gatggcctca agacgggat cattcttttgc gaatttatca acaagctgca     300
gccgggttct gtgaagaagg tcaatgagtc aactcagaac tggcaccagc tggagaacat     360
aggtaatttc atcaaagcca ttaccaagta tggggtgaaa ccccacgaca tctttgaggc     420
caacgacctg tttgaaaaca ccaaccatac acaagttcag tccactctcc tggctctggc     480
cagcatggcc aagacaaaag gaaacaaagt caatgtggga gtcaagtatg cagagaaaca     540
agagcggaga tttgagccgg agaagttgag agaaggcagg aacatcattg gactgcagat     600
gggcaccaac aagtttgcca gtcagcaggg catgacggcc tacggtacac ggcgtcacct     660
```

```
ctatgatccc aaactgggta cagatcagcc tctggaccag gcgaccatca gcctgcagat    720
gggcaccaac aagggtgcca gccaggctgg catgactgca ccaggcacca gcggcagat    780
ctttgagcca ggtctgggca tggaacactg cgacacactc aacgtcagct tgcagatggg    840
cagcaacaag ggggcctccc agaggggcat gacagtgtat gggcttcctc gccaggtgta    900
cgatcccaag tactgcctga acccggagta cccagagctg agtgagccca cccacaatca    960
ccacccgcac aactactaca actctgccta ggggcccccca aggggctggc tgctgctctt   1020
ggctggaccc agctggccca gccaaccccca tctcctgcat ggcgtcctcc cagcccctg   1080
gcacctgcct atagggttac ggtttgggga gatgaggccg agggggggcaa tgggaagaag   1140
ggggcccctc atccctggag ctttcgcagg gcccaacata gaactgggtg tccccaacag   1200
tgcccgaagg aagcactgag ttgagctgtt tcagctgccc ccctttattc cctcacaagt   1260
aagtacctcc cagaaccaga aaccccttcca gcgaagcccc cagaaccccag gcttggcctg   1320
accccctgccc cattcctgcg acgggagcag atgcatgcct ggaaacgcag tggacacacg   1380
cattttggtt ttgcagtgac tggtgtttgt ggatgtgaca gcagcgtttg taactcgaac   1440
acattctttt ctatttcact ggagcacaat aaatggctgt gacatcaaaa aaaaaaaaa    1500
aaaaaaaaaa aaaaaccgga attc                                          1524

<210> SEQ ID NO 15
<211> LENGTH: 297
<212> TYPE: PRT
<213> ORGANISM: Sus scrofa

<400> SEQUENCE: 15

Met Ser Ser Ala His Phe Asn Arg Gly Pro Ala Tyr Gly Leu Ser Ala
1               5                   10                  15

Glu Val Lys Asn Lys Leu Ala Gln Lys Tyr Asp His Gln Gln Glu Gln
            20                  25                  30

Glu Leu Arg Glu Trp Ile Glu Gly Val Thr Gly Arg Arg Ile Gly Asn
        35                  40                  45

Asn Phe Met Asp Gly Leu Lys Asp Gly Ile Ile Leu Cys Glu Phe Ile
    50                  55                  60

Asn Lys Leu Gln Pro Gly Ser Val Lys Val Asn Glu Ser Thr Gln
65                  70                  75                  80

Asn Trp His Gln Leu Glu Asn Ile Gly Asn Phe Ile Lys Ala Ile Thr
                85                  90                  95

Lys Tyr Gly Val Lys Pro His Asp Ile Phe Glu Ala Asn Asp Leu Phe
            100                 105                 110

Glu Asn Thr Asn His Thr Gln Val Gln Ser Thr Leu Leu Ala Leu Ala
        115                 120                 125

Ser Met Ala Lys Thr Lys Gly Asn Lys Val Asn Val Gly Val Lys Tyr
    130                 135                 140

Ala Glu Lys Gln Glu Arg Lys Phe Glu Pro Glu Lys Leu Arg Glu Gly
145                 150                 155                 160

Arg Asn Ile Ile Gly Leu Gln Met Gly Thr Asn Lys Phe Ala Ser Gln
                165                 170                 175

Gln Gly Met Thr Ala Tyr Gly Thr Arg Arg His Leu Tyr Asp Pro Lys
            180                 185                 190

Leu Gly Thr Asp Gln Pro Leu Asp Gln Ala Thr Ile Ser Leu Gln Met
        195                 200                 205

Gly Thr Asn Lys Gly Ala Ser Gln Ala Gly Met Thr Ala Pro Gly Thr
    210                 215                 220
```

```
Lys Arg Gln Ile Phe Glu Pro Gly Leu Gly Met Glu His Cys Asp Thr
225                 230                 235                 240

Leu Asn Val Ser Leu Gln Met Gly Ser Asn Lys Gly Ala Ser Gln Arg
            245                 250                 255

Gly Met Thr Val Tyr Gly Leu Pro Arg Gln Val Tyr Asp Pro Lys Tyr
                260                 265                 270

Cys Leu Thr Pro Glu Tyr Pro Glu Leu Gly Glu Pro Ala His Asn His
            275                 280                 285

His Pro His Asn Tyr Tyr Asn Ser Ala
    290                 295

<210> SEQ ID NO 16
<211> LENGTH: 1470
<212> TYPE: DNA
<213> ORGANISM: Sus scrofa

<400> SEQUENCE: 16
```

| | | | | | |
|---|---|---|---|---|---|
| gaattccagc | ttcagctgct | gccgccggct | tcagcgcaca | ctgccaccgc | tgcccaccat | 60 |
| ccgccagcat | gtcctctgct | cacttcaacc | gaggcccccgc | ctacgggctg | tcggctgagg | 120 |
| tcaagaacaa | gctggcccag | aagtatgacc | accagcagga | gcaggagctt | cgagagtgga | 180 |
| tcgaggggt | gacagggcgc | cgcatcggca | caacttcat | ggacggcctc | aaagatggca | 240 |
| tcattctttg | cgagttcatc | aataagctcc | agccaggctc | cgtgaagaag | gtcaatgagt | 300 |
| ccacccagaa | ctggcaccag | ctggagaaca | ttggcaactt | catcaaggcc | atcaccaagt | 360 |
| atggggtgaa | gccccacgac | atctttgaag | ccaacgacct | gttcgagaac | accaaccaca | 420 |
| cacaagtgca | gtccacgctc | ctggccctgg | ccagcatggc | caagacgaaa | gggaacaagg | 480 |
| tgaacgtggg | agtgaaatat | gcggagaagc | aggaacggaa | atttgagccg | gagaagctaa | 540 |
| gagaagggcg | gaacatcatt | gggctgcaga | tgggcaccaa | caagtttgcc | agtcagcagg | 600 |
| gcatgacagc | ctatggcacc | cggcgccacc | tctacgaccc | caagctgggc | acggaccagc | 660 |
| ccctggacca | ggctaccatc | agcctgcaga | tgggcaccaa | caaggggagcc | agccaggctg | 720 |
| gcatgaccgc | tcccgggacc | aagcggcaga | tcttcgagcc | ggggctgggc | atggagcact | 780 |
| gtgacacgct | caacgtcagc | ctacagatgg | gcagcaacaa | gggggcctcg | cagcggggca | 840 |
| tgacggtgta | tggactgccc | cgccaagtct | acgatcccaa | gtactgcctg | acgcctgagt | 900 |
| acccggagct | gggcgaacct | gcccacaacc | accaccccgca | caactactac | aactctgcct | 960 |
| agggtgctgg | gcctcccacc | ttcccccagg | gaggctggct | gctgctcttg | gtgggcctgg | 1020 |
| cctggcctgc | tgacccccctc | cccctgcatg | gctcctccag | cccctggca | cctgcctaca | 1080 |
| gggttagtgt | ttgtggggag | cagactgggg | aacctgtggg | ggggaagggg | gcacctccct | 1140 |
| ggagcactac | gaggtccaac | atggagctgg | gtgttccaa | cagcacccaa | aggacgcact | 1200 |
| gagcaaagct | accccgctgt | ccccactcc | ccacaggtgg | gtccccccc | cggaccagaa | 1260 |
| gccccccaa | gcgaagcccc | cagagcccac | gtcgcgcctc | ccccaccccc | attcccgcag | 1320 |
| tgggagcaaa | ctgcatgccc | agagacccag | aggacacacg | cggtttggtt | tgcagctggc | 1380 |
| ctatgggatg | tgacagtggc | gtttgtaacg | cgagcacttt | cttttctac | ttcactggag | 1440 |
| cacaataaat | agctgtaaaa | tcaggaattc | | | | 1470 |

```
<210> SEQ ID NO 17
<211> LENGTH: 309
<212> TYPE: PRT
<213> ORGANISM: Homo sapiens
```

<400> SEQUENCE: 17

```
Met Ser Ser Thr Gln Phe Asn Lys Gly Pro Ser Tyr Gly Leu Ser Ala
1               5                   10                  15

Glu Val Lys Asn Arg Leu Leu Ser Lys Tyr Asp Pro Gln Lys Glu Ala
            20                  25                  30

Glu Leu Arg Thr Trp Ile Glu Gly Leu Thr Gly Leu Ser Ile Gly Pro
        35                  40                  45

Asp Phe Gln Lys Gly Leu Lys Asp Gly Thr Ile Leu Cys Thr Leu Met
    50                  55                  60

Asn Lys Leu Gln Pro Gly Ser Val Pro Lys Ile Asn Arg Ser Met Gln
65                  70                  75                  80

Asn Trp His Gln Leu Glu Asn Leu Ser Asn Phe Ile Lys Ala Met Val
                85                  90                  95

Ser Tyr Gly Met Asn Pro Val Asp Leu Phe Glu Ala Asn Asp Leu Phe
            100                 105                 110

Glu Ser Gly Asn Met Thr Gln Val Gln Val Ser Leu Leu Ala Leu Ala
        115                 120                 125

Gly Lys Ala Lys Thr Lys Gly Leu Gln Ser Gly Val Asp Ile Gly Val
    130                 135                 140

Lys Tyr Ser Glu Lys Gln Glu Arg Asn Phe Asp Asp Ala Thr Met Lys
145                 150                 155                 160

Ala Gly Gln Cys Val Ile Gly Leu Gln Met Gly Thr Asn Lys Cys Ala
                165                 170                 175

Ser Gln Ser Gly Met Thr Ala Tyr Gly Thr Arg Arg His Leu Tyr Asp
            180                 185                 190

Pro Lys Asn His Ile Leu Pro Pro Met Asp His Ser Thr Ile Ser Leu
        195                 200                 205

Gln Met Gly Thr Asn Lys Cys Ala Ser Gln Val Gly Met Thr Ala Pro
    210                 215                 220

Gly Thr Arg Arg His Ile Tyr Asp Thr Lys Leu Gly Thr Asp Lys Cys
225                 230                 235                 240

Asp Asn Ser Ser Met Ser Leu Gln Met Gly Tyr Thr Gln Gly Ala Asn
                245                 250                 255

Gln Ser Gly Gln Val Phe Gly Leu Gly Arg Gln Ile Tyr Asp Pro Lys
            260                 265                 270

Tyr Cys Pro Gln Gly Thr Val Ala Asp Gly Ala Pro Ser Gly Thr Gly
        275                 280                 285

Asp Cys Pro Asp Pro Gly Glu Val Pro Glu Tyr Pro Pro Tyr Gln
    290                 295                 300

Glu Glu Ala Gly Tyr
305
```

<210> SEQ ID NO 18
<211> LENGTH: 2478
<212> TYPE: DNA
<213> ORGANISM: Homo sapiens

<400> SEQUENCE: 18

```
gaaagagtga gagccgccca cgagctctga gcagagagcc cgcaggagtg ccacgtcccg    60
gcggcctcgg cccctccctg cctcagtttc ccgtggcatc aaaggggggcg aggggcccct    120 ccaggcctct ggtgacgggg gtgctgtgcc caggcggggg tccggggggcg accgaggggg   180 ctcaggaagt ccgcggccgc aggaattcgg cgcctccagg ccttataagg acatttgcgc   240
tccgggccaa tcagcggcgg gggcgtggcg cgcggagccc ggcgcgtccc aacccgcgc    300
```

```
cagcccggcg gtcccgtccc gtcccgtcct gtgcggcccc gtcccgccgc ccgcccgcca        360
gccatgagct ccacgcagtt caacaagggc ccctcgtacg ggctgtcggc cgaggtcaag        420
aaccggctcc tgtccaaata tgaccccag aaggaggcag agctccgcac ctggatcgag         480
ggactcaccg gcctctccat cggccccgac ttcagaagg gcctgaagga tggaactatc         540
ttatgcacac tcatgaacaa gctacagccg ggctccgtcc ccaagatcaa ccgctccatg        600
cagaactggc accagctaga aaacctgtcc aacttcatca aggccatggt cagctacggc        660
atgaaccctg tggacctgtt cgaggccaac gacctgtttg agagtgggaa catgacgcag        720
gtgcaggtgt ctcttctcgc cctggcgggg aaggccaaga ctaaggggct gcagagcggg        780
gtggacattg gcgtcaagta ctcggagaag caggagcgga atttcgacga tgccaccatg        840
aaggctggcc agtgcgtcat cgggctgcag atgggcacca caaatgcgc cagccagtcg         900 ggcatgactg cctacggcac gagaaggcat ctctatgacc ccaagaacca tatcctgccc        960
cccatggacc actcgaccat cagcctccag atgggcacga caagtgtgc cagccaggtg        1020 ggcatgacgg ctcccgggac ccggcggcac atctatgata ccaagctggg aaccgacaag       1080
tgtgacaact cctccatgtc cctgcagatg ggctacacgc agggcgccaa ccagagcggc       1140
caggtcttcg gcctgggccg gcagatatat gaccccaagt actgcccgca aggcacagtg       1200
gccgatgggg ctccctcggg caccggcgac tgcccggacc cggggaggt ccctgaatat        1260 ccccttact accaggagga ggccggctac tgaggctccc agcacgctct ctccccacat        1320
cgtctgccca tctgggtttt tgggttttc tgtgttttca tcttttttt tttttcta            1380 acccgttcag tgctgccagt caaccaaggg tctgtgagtg tcagcgtggg atcaggcagc       1440 agagctttt tccctttgc cttgatcctt cgcaaggctg agccactggg ctgtggggga         1500
aggggtcaag gccatatccc aatacgtgta gggcgagggt ccctgctggc acattcaggc      1560
tgtgctggga agaagagacc tgggcttgga aggaaccggt ccccgacggt ttctgcttgc       1620
ctcgcctctt ccccctttg tcagctgagc agtttgtggt ttctatgccc gcaagtttca        1680
ggaagtattc acaaaagaaa aatacatttt ttccccagg ggtggggcaa ggacagtgga        1740
gagagtgcta ggaaatgagt ccctggggaa agggaccgg gccgtgatgt taaatatctc        1800
cggctcccaa gtgactggat ttgcctagga ccttcagatc aacagacttc agaccctcag      1860
acctgccccg gggccaggtg gagaaagtga gggccgtaca aggaagtgaa attctgagtt       1920 gttgggggcta agcctgaccc cctctccatg ctcccgccc caactcactc tggcctcagt      1980
agattttttt ttcagttgtg gttgttgccc aggctggagt gcagtggcgc catcttggct       2040
cactgcacct ccaccttccg ggctcaagcg attctccagc ctcagcctcc tgagtagcta     2100
ggactgcagg tgctccacca cgcccggcta attttttgtat ttttagtaga gatgggggttt    2160 ccccatgttg gccaggctgg tctcgaactc ctggcctcag gtgtgatccg cccgcctccg     2220 cctcccaag cgctgagatt acaggtgtga gccaccgtgc ccaggccctc agtaggtttt        2280
aaggagtccc cagccctcct cccttctggg cccgaccagc ttatactgct ccatcttccc     2340
cggccacatg ccccgccaag tactgcacag ggacccccca cccagggccc ctgctccgtg    2400
agataatgtg aaatacgact gtggaccaaa cgcaataaaa cctctgtttg tacgaagaaa    2460
aaaaaaaaaa aaaaaaaa                                                     2478

<210> SEQ ID NO 19
<211> LENGTH: 270
<212> TYPE: PRT
<213> ORGANISM: Homo sapiens
```

```
<400> SEQUENCE: 19

Met Ser Ser Thr Gln Phe Asn Lys Gly Pro Ser Tyr Gly Leu Ser Ala
1               5                   10                  15

Glu Val Lys Asn Arg Leu Leu Ser Lys Tyr Asp Pro Gln Lys Glu Ala
            20                  25                  30

Glu Leu Arg Thr Trp Ile Glu Gly Leu Thr Gly Leu Ser Ile Gly Pro
        35                  40                  45

Asp Phe Gln Lys Gly Leu Lys Asp Gly Thr Ile Leu Cys Thr Leu Met
    50                  55                  60

Asn Lys Leu Gln Pro Gly Ser Val Pro Lys Ile Asn Arg Ser Met Gln
65                  70                  75                  80

Asn Trp His Gln Leu Glu Asn Leu Ser Asn Phe Ile Lys Ala Met Val
                85                  90                  95

Ser Tyr Gly Met Asn Pro Val Asp Leu Phe Glu Ala Asn Asp Leu Phe
            100                 105                 110

Glu Ser Gly Asn Met Thr Gln Val Gln Val Ser Leu Leu Ala Leu Ala
        115                 120                 125

Gly Lys Met Gly Thr Asn Lys Cys Ala Ser Gln Ser Gly Met Thr Ala
    130                 135                 140

Tyr Gly Thr Arg Arg His Leu Tyr Asp Pro Lys Asn His Ile Leu Pro
145                 150                 155                 160

Pro Met Asp His Ser Thr Ile Ser Leu Gln Met Gly Thr Asn Lys Cys
                165                 170                 175

Ala Ser Gln Val Gly Met Thr Ala Pro Gly Thr Arg Arg His Ile Tyr
            180                 185                 190

Asp Thr Lys Leu Gly Thr Asp Lys Cys Asp Asn Ser Ser Met Ser Leu
        195                 200                 205

Gln Met Gly Tyr Thr Gln Gly Ala Asn Gln Ser Gly Gln Val Phe Gly
    210                 215                 220

Leu Gly Arg Gln Ile Tyr Asp Pro Lys Tyr Cys Pro Gln Gly Thr Val
225                 230                 235                 240

Ala Asp Gly Ala Pro Ser Gly Thr Gly Asp Cys Pro Asp Pro Gly Glu
                245                 250                 255

Val Pro Glu Tyr Pro Pro Tyr Tyr Gln Glu Glu Ala Gly Tyr
            260                 265                 270

<210> SEQ ID NO 20
<211> LENGTH: 2361
<212> TYPE: DNA
<213> ORGANISM: Homo sapiens

<400> SEQUENCE: 20
gaaagagtga gagccgccca cgagctctga gcagagagcc cgcaggagtg ccacgtcccg      60
gcggcctcgg cccctccctg cctcagtttc ccgtggcatc aaaggggcg agggccccct     120 ccaggcctct ggtgacgggg gtgctgtgcc caggcggggg tccggggggcg accgagggg     180 ctcaggaagt ccgcggccgc aggaattcgg cgcctccagg ccttataagg acatttgcgc    240
tccgggccaa tcagcggcgg gggcgtggcg cgcggagccc ggcgcgtccc aacccgcgc     300 cagcccggcg gtcccgtccc gtccgtcct gtgcggcccc gtcccgccgc cgcccgcca     360 gccatgagct ccacgcagtt caacaagggc ccctcgtacg gctgtcggc cgaggtcaag    420 aaccggctcc tgtccaaata tgaccccag aaggaggcag agctccgcac ctggatcgag     480
ggactcaccg gcctctccat cggccccgac ttcagaagg gctgaagga tggaactatc     540 ttatgcacac tcatgaacaa gctacagccg ggctccgtcc ccaagatcaa ccgctccatg     600
```

```
cagaactggc accagctaga aaacctgtcc aacttcatca aggccatggt cagctacggc    660
atgaaccctg tggacctgtt cgaggccaac gacctgtttg agagtgggaa catgacgcag    720
gtgcaggtgt ctcttctcgc cctggcgggg aagatgggca ccaacaaatg cgccagccag    780
tcgggcatga ctgcctacgg cacgagaagg catctctatg accccaagaa ccatatcctg    840
ccccccatgg accactcgac catcagcctc cagatgggca cgaacaagtg tgccagccag    900
gtgggcatga cggctcccgg gacccggcgg cacatctatg ataccaagct gggaaccgac    960
aagtgtgaca actcctccat gtccctgcag atgggctaca cgcagggcgc caaccagagc   1020
ggccaggtct tcggcctggg ccggcagata tatgacccca gtactgccc gcaaggcaca    1080 gtggccgatg ggctccctc gggcaccggc gactgcccgg accggggga ggtccctgaa    1140 tatccccctt actaccagga ggaggccggc tactgaggct cccagcacgc tctctcccca   1200
catcgtctgc ccatctgggt ttttgggttt ttctgtgttt tcatctttt tttttttttc   1260 ttaacccgtt cagtgctgcc agtcaaccaa gggtctgtga gtgtcagcgt gggatcaggc   1320
agcagagctt ttttcccctt tgccttgatc cttcgcaagg ctgagccact gggctgtggg   1380 ggaagggtc aaggccatat cccaatacgt gtagggcgag ggtccctgct ggcacattca   1440
ggctgtgctg ggaagaagag acctgggctt ggaaggaacc ggtccccgac ggtttctgct   1500
tgcctcgcct cttccccctt tgtcagctg agcagtttgt ggtttctatg cccgcaagtt   1560
tcaggaagta ttcacaaaag aaaaatacat ttttttccccc aggggtgggg caaggacagt   1620
ggagagagtg ctaggaaatg agtccctgg gaaggggac cgggccgtga tgttaaatat   1680
ctccggctcc caagtgactg gatttgccta ggaccttcag atcaacagac ttcagaccct   1740
cagacctgcc ccggggccag gtggagaaag tgagggccgt acaaggaagt gaaattctga   1800
gttgttgggg ctaagcctga ccccctctcc atgctccccg cccaactca ctctggcctc   1860 agtagattt tttttcagtt gtggttgttg cccaggctgg agtgcagtgg cgccatcttg   1920
gctcactgca cctccacctt ccgggctcaa gcgattctcc agcctcagcc tcctgagtag   1980
ctaggactgc aggtgctcca ccacgcccgg ctaattttg tattttagt agagatgggg   2040 tttccccatg ttggccaggc tggtctcgaa ctcctggcct caggtgtgat ccgcccgcct   2100
ccgcctcccc aagcgctgag attacaggtg tgagccaccg tgcccaggcc tcagtaggt   2160 tttaaggagt ccccagccct cctcccttct gggcccgacc agcttatact gctccatctt   2220
ccccggccac atgccccgcc aagtactgca cagggacccc ccaccaggg gccctgctcc   2280 gtgagataat gtgaaatacg actgtggacc aaacgcaata aaacctctgt ttgtacgaag   2340
aaaaaaaaaa aaaaaaaaa a                                               2361
```

<210> SEQ ID NO 21
<211> LENGTH: 305
<212> TYPE: PRT
<213> ORGANISM: Mus musculus

<400> SEQUENCE: 21

Met Ser Ser Thr Gln Phe Asn Lys Gly Pro Ser Tyr Gly Leu Ser Ala
1               5                   10                  15

Glu Val Lys Asn Arg Leu Leu Ser Lys Tyr Asp Pro Gln Lys Glu Ala
                20                  25                  30

Glu Leu Arg Ser Trp Ile Glu Gly Leu Thr Gly Leu Ser Ile Gly Pro
            35                  40                  45

Asp Phe Gln Lys Gly Leu Lys Asp Gly Val Ile Leu Cys Thr Leu Met
        50                  55                  60

Asn Lys Leu Gln Pro Gly Ser Val Pro Lys Ile Asn Arg Ser Met Gln
 65                  70                  75                  80

Asn Trp His Gln Leu Glu Asn Leu Ser Asn Phe Ile Lys Ala Met Val
                 85                  90                  95

Ser Tyr Gly Met Asn Pro Val Asp Leu Phe Glu Ala Asn Asp Leu Phe
            100                 105                 110

Glu Ser Gly Asn Met Thr Gln Val Gln Val Ser Leu Leu Ala Leu Ala
        115                 120                 125

Gly Lys Ala Lys Thr Lys Gly Leu Gln Ser Gly Val Asp Ile Gly Val
    130                 135                 140

Lys Tyr Ser Glu Lys Gln Glu Arg Asn Phe Asp Asp Ala Thr Met Lys
145                 150                 155                 160

Ala Gly Gln Cys Val Ile Gly Leu Gln Met Gly Thr Asn Lys Cys Ala
                165                 170                 175

Ser Gln Ser Gly Met Thr Ala Tyr Gly Thr Arg Arg His Leu Tyr Asp
            180                 185                 190

Pro Lys Asn His Ile Leu Pro Pro Met Asp His Cys Thr Ile Ser Leu
        195                 200                 205

Gln Met Gly Thr Asn Lys Cys Ala Ser Gln Val Gly Met Thr Ala Pro
    210                 215                 220

Gly Thr Arg Arg His Ile Tyr Asp Thr Lys Leu Gly Thr Asp Lys Cys
225                 230                 235                 240

Asp Asn Ser Ser Met Ser Leu Gln Met Gly Tyr Thr Gln Gly Ala Asn
                245                 250                 255

Gln Ser Gly Gln Val Phe Gly Leu Gly Arg Gln Ile Tyr Asp Pro Lys
            260                 265                 270

Tyr Cys Pro Gln Gly Ser Ala Ala Asp Gly Ala Pro Ala Gly Asp Gly
        275                 280                 285

Gln Gly Glu Ala Pro Glu Tyr Leu Ala Tyr Cys Gln Glu Glu Ala Gly
    290                 295                 300

Tyr
305

<210> SEQ ID NO 22
<211> LENGTH: 1800
<212> TYPE: DNA
<213> ORGANISM: Mus musculus

<400> SEQUENCE: 22
cgtcccgggc cgtccgcccg cagcccgacc ctctgccggt cccgctggtc ctcctgtccc      60 gctccgggt cccgcgccat gagctccacg cagttcaaca agggcccgtc ctacgggctc     120
tcggccgagg tcaagaaccg gctcctgtcc aaatatgacc ccaaaaggaa agcagaactc     180
cgaagctgga tagagggact cacgggcctc tccattggcc ctgacttcca gaagggtctg     240
aaagatgggg ttatcctatg cacactcatg aacaagctgc agccaggctc cgtccctaaa     300
atcaaccgct ctatgcagaa ctggcaccag ctagaaaatc tctccaactt catcaaggcc     360
atggtcagct acggcatgaa ccctgtggac ctgtttgagg ccaatgacct gttcgagagc     420 ggaacatga cacaggtgca agtgtctctg cttgcactgg ctggaaaggc caagaccaag     480
gggctgcaga gtggtgtgga cattggagtt aagtattcgg agaaacagga ggaactttt     540 gacgacgcca ccatgaaggc cggccagtgc gtcatcgggc tgcagatggg caccaacaag     600
tgtgccagcc agtctggcat gacagcctat ggtaccagga cacatctcta tgaccccaag     660
aaccatatcc tgcctcccat ggaccactgc accatcagcc tccagatggg caccaacaag     720

```
tgtgccagcc aggtgggcat gacagctcca gggacccgga ggcacatcta tgacaccaag    780
ctgggcaccg acaagtgcga caactcttcc atgtccctgc agatgggcta cacgcagggc    840
gccaaccaga gcggtcaggt cttcggactg gggcggcaga tctacgatcc caagtattgc    900
ccacagggct ctgcagctga cggggctcct gcgggtgacg gccaaggcga ggccccagag    960
tacctggcct actgccagga ggaagctggc tactgagcac ccagcatgcc agctccccca   1020
ctgcatcagc agccctgtgt gggctttggg gttttcattg tgttttgtgt ttggaaactg   1080
gtcatctctt tgtatctctc tctgcctgga aactcactgc aatcctcctg cctcagcttc   1140
ctaagggctg ggatgacaga tctgtgctat ctatgctcct tcctcaccca ccatgcctcg   1200
cttccttccc aggattgacc caccagacag gggacatggg tgtccttggt gggacagtga   1260
ggctgtgcgt ttcccagtgg gctgtgggag aggctggccc caatgggctt cctgtttctt   1320
catctctttc acatcagttt gtggtttgtg aacccgggga aattacaggc agtttcaatg   1380
aaagaaaaca aggggttttg tgggggtttt gcctcaaaag tattggagta cactaggctt   1440
taaaatactg caggcattct gagggactaa gtttgctttc ccacgactct cagacttcac   1500
cctcctgtgc cccgtgggga aactgaggca agccagatgt gaccccaacg cctgcagccc   1560
tccctcactc ctctggtgtt tgaaggcttc cctgcccctg tgcaggccct gattaggtgt   1620
gctagagtct gggcctcgga aggggccaca catgacccac acgggcccct gcactgccag   1680
aaaatgtgaa attccctgtg tggaccaaaa aacaaaaaa aaaacaaaa acaaaacaaa     1740 aacaaaaaca ataaaaacct ctgtttctaa gagtaaagta caaaaaaaaa aaaaaaaaa    1800
```

<210> SEQ ID NO 23
<211> LENGTH: 2045
<212> TYPE: DNA
<213> ORGANISM: Homo sapiens
<220> FEATURE:
<223> OTHER INFORMATION: Human calponin 3

<400> SEQUENCE: 23

```
ctgtggggaa ccgaggtgcg ggcggcgagc gaggcagccg ggtgcttcgc agcggagctc     60
gaggctctgt agcacccagt tggacccagt cgcccaggca ccgcccgcgc ccgcggccg    120 tctcctgcgc ctcccagagg agggagttcg agcatccccc gcggcggcca ctcctcgggg    180
ccaggagcgg ggaagcgaag tgcgagagac cccggacccc agcgctgtct cttcccgccg    240
cccgaaccac catgacccac ttcaacaagg gcccttccta tgggctctcg gccgaagtca    300
agaacaagat tgcttccaag tatgatcatc aggcagaaga agatcttcgc aattggatag    360
aagaggtgac aggcatgagc attggcccca acttccagct gggcttaaag gatggcatca    420
tcctctgcga acttataaac aagctacagc caggctcagt gaagaaggtc aacgagtcct    480
cactgaactg gcctcagttg gagaatattg gcaactttat taaagctatt caggcttatg    540
gtatgaagcc acatgacata ttcgaagcaa atgatctttt tgagaatgga aacatgaccc    600
aggttcagac tactctggtg gctctagcag gtctggctaa aacaaaagga ttccatacaa    660
ccattgacat tggagttaag tatgcagaaa aacaaacaag acgttttgat gaaggaaaat    720
taaaagctgg ccaaagtgta attggtctgc agatgggaac caacaaatgt gccagccagg    780
caggtatgac agcttacggg actaggaggc atctttatga tccaaaatgt caaactgaca    840 aacctttga ccagaccaca attagtctgc agatgggcac taataaagga gccagccagg    900
cagggatgtt agcaccaggt accagaagag acatctatga tcagaagcta acattacagc    960
cggtggacaa ctcgacaatt tccctacaga tgggtaccaa caaagttgct tcccagaaag   1020
```

```
gaatgagtgt gtatgggctt gggcggcaag tatatgatcc caaatactgt gctgctccta    1080
cagaacctgt cattcacaac ggaagccaag gaacaggaac aaatggttcg gaaatcagtg    1140
atagtgatta tcaggcagaa taccctgatg agtatcatgg cgagtaccag gatgactacc    1200
ccagagatta ccaatatagc gaccaaggca ttgattatta gatccacaca gaaggagctc    1260
agtatttagt cctttgtttt tattcagtga gaaccaagct agccttgagt aattttttatc   1320 ttgtcttcct aaaacactat taagcttatt gtacttttaa gaaaaattgc cttacgtaca    1380
ttcctttttc cttttctgc ctcttccctc aatagttgcc ttttagtgct gtaatagtta    1440
aatcctacag cataatcaat aactcgcata tgaagtaaaa aggaatactg tgaaagggga    1500
gtactcttgt acagccagtt cttttatgca aaaatctatg cattttttaca atcttatatt   1560 aaactggtat tttcaaacaa taggaaactt tttttttttt ttttttttac agtttagtgt    1620
atctggtttc tacatggaag actaaactca tgcttattgc taaatgtggt ctttgccaac    1680
taaatttaag atgcagcatt ttagaaattt acatatcaat gtttctacag tattgtttgc    1740 taattttttaa ataaagtcat gatcagtgtg catttgtgat tatatgtgta ctcattctct   1800
tacctagcga acaagatctt ttcagagtgg tgtttctaaa agagcatgta caaaagtggc    1860
ctgtggacat ttaggcctgg gtgatgcatt tgctcttcct gtttgtgcca atgtatcaat    1920
gtagagttgc tctgttttct tcaactgtat ttattgctgc atttctcagc ataaacttat    1980
cccattgtat tttttataaa taaatatttt ttttgaactt tcatatgaaa aaaaaaaaa    2040 aaaaa                                                                2045

<210> SEQ ID NO 24
<211> LENGTH: 329
<212> TYPE: PRT
<213> ORGANISM: Homo sapiens
<220> FEATURE:
<223> OTHER INFORMATION: Human calponin 3

<400> SEQUENCE: 24

Met Thr His Phe Asn Lys Gly Pro Ser Tyr Gly Leu Ser Ala Glu Val
1               5                   10                  15

Lys Asn Lys Ile Ala Ser Lys Tyr Asp His Gln Ala Glu Glu Asp Leu
            20                  25                  30

Arg Asn Trp Ile Glu Glu Val Thr Gly Met Ser Ile Gly Pro Asn Phe
        35                  40                  45

Gln Leu Gly Leu Lys Asp Gly Ile Ile Leu Cys Glu Leu Ile Asn Lys
    50                  55                  60

Leu Gln Pro Gly Ser Val Lys Lys Val Asn Glu Ser Ser Leu Asn Trp
65                  70                  75                  80

Pro Gln Leu Glu Asn Ile Gly Asn Phe Ile Lys Ala Ile Gln Ala Tyr
                85                  90                  95

Gly Met Lys Pro His Asp Ile Phe Glu Ala Asn Asp Leu Phe Glu Asn
            100                 105                 110

Gly Asn Met Thr Gln Val Gln Thr Thr Leu Val Ala Leu Ala Gly Leu
        115                 120                 125

Ala Lys Thr Lys Gly Phe His Thr Thr Ile Asp Ile Gly Val Lys Tyr
    130                 135                 140

Ala Glu Lys Gln Thr Arg Arg Phe Asp Glu Gly Lys Leu Lys Ala Gly
145                 150                 155                 160

Gln Ser Val Ile Gly Leu Gln Met Gly Thr Asn Lys Cys Ala Ser Gln
                165                 170                 175
```

```
Ala Gly Met Thr Ala Tyr Gly Thr Arg Arg His Leu Tyr Asp Pro Lys
            180                 185                 190

Met Gln Thr Asp Lys Pro Phe Asp Gln Thr Thr Ile Ser Leu Gln Met
        195                 200                 205

Gly Thr Asn Lys Gly Ala Ser Gln Ala Gly Met Leu Ala Pro Gly Thr
    210                 215                 220

Arg Arg Asp Ile Tyr Asp Gln Lys Leu Thr Leu Gln Pro Val Asp Asn
225                 230                 235                 240

Ser Thr Ile Ser Leu Gln Met Gly Thr Asn Lys Val Ala Ser Gln Lys
                245                 250                 255

Gly Met Ser Val Tyr Gly Leu Gly Arg Gln Val Tyr Asp Pro Lys Tyr
            260                 265                 270

Cys Ala Ala Pro Thr Glu Pro Val Ile His Asn Gly Ser Gln Gly Thr
        275                 280                 285

Gly Thr Asn Gly Ser Glu Ile Ser Asp Ser Asp Tyr Gln Ala Glu Tyr
    290                 295                 300

Pro Asp Glu Tyr His Gly Glu Tyr Gln Asp Asp Tyr Pro Arg Asp Tyr
305                 310                 315                 320

Gln Tyr Ser Asp Gln Gly Ile Asp Tyr
                325
```

```
<210> SEQ ID NO 25
<211> LENGTH: 1785
<212> TYPE: DNA
<213> ORGANISM: Bos taurus
<220> FEATURE:
<223> OTHER INFORMATION: Bos Taurus calponin 3 (acidic)

<400> SEQUENCE: 25
agttcgtgcg ggactccgga gccgagcggg agcgtctggg ggacctcgtc cgatcgagta      60
gccgaggcac cgcccgcgtc ccgccgccgc gtccggcgga ctcctgcgcc gcccaggaga     120
gcgagctccg agcatcttgt agtgcggcca ctcttcgggg ccaggagcgg ggaaaccgag     180
tgcaagaaac ccccggaccc gaactcagcc tcttcccgcc gcgcgaatca tcatgaccca     240
cttcaacaag ggcccttcct atgggctctc ggccgaggtc aagaacaaga ttgcttccaa     300
gtatgatcat caggcagaag aagatctccg caattggata aagaggtga caggcatgag      360
cattggcgcc aacttccagc tgggcttgaa agatggcatt atcctctgcg aactcataaa     420
caagctacag ccaggctcag tgaagaaggt caatgagtcc tcattaaact ggcctcagtt     480
ggagaatatc ggcaacttta ttaaagctat tcaggcttat ggcatgaagc acatgacat      540
atttgaagca aatgatcttt ttgagaatgg aaacatgacc caggttcaga ctacgttggt     600
ggccctagca ggtctggcca aaacaaaagg attccataca accattgaca ttggagttaa     660
gtatgcagaa aaacaaacaa gacgctttga tgaaggaaaa ttaaaagctg ccagagtgt      720
aattggtttg cagatgggaa ccaacaaatg cgccagccaa gcaggtatga cagcctatgg     780
gacgaggagg cacctttatg atcccaaaat gcaaactgac aaacctttg atcagaccac      840
aattagcctg caaatgggca ccaacaaagg agccagccag gcgggaatgt tagcaccggg     900
taccccgaaga gacatctacg atcagaagct aacattacaa cccgtggaca actcgacgat     960
ttccctacag atgggtacca acaaagtcgc ttcccagaaa ggaatgagtg tgtatgggct    1020
tgggcggcaa gtgtatgatc ccaaatactg tgctgctccc acagaacctg tcattcacaa    1080
cggaagccaa ggaacaggaa ccaatgggtc agaaatcagt gatagtgatt atcaggcaga    1140
ataccccgat gaatatcatg gcgagtacca agatgactac cccagagatt accagtatgg    1200
```

-continued

```
tgaccaaggc attgattatt agattcacag aggagctcag tatttagccc attgttttta    1260
ttcagtgaga accaagctag ccttgagtaa ttttttatctt gtcttcctaa aacactatta    1320
tgcttattgt acctaaagga actattgcct tacatacatt cctttttacct ttttctgcct    1380 cttccctaaa tagttgcctt ttagtgctgt gacagttaaa tcctacagca taaccaataa    1440
ctcacatatg aagtaaaaag gaatactgtg aaggggagt actcttgtac agtcaattct     1500
ttcattaaaa atctatgcat ttttacagtc ctctacttaa actggtattt tcaaacaata    1560
ggaagctttt ttttttttt acagtttagt atcttgtttc tacatggaag actaaacatg      1620
cttatagcta aatgtggtct ttgccaacta aatttaagat gcagcgtttt ataaatttac    1680
atatcaatgt ttctacagta ttgtttgcta attttttaaat aaagtcctga tcagtgtgca   1740 aaaaaaaaa aaaaaaaaa aaaaaaaaaa aaaaaaaaaa aaaaa                      1785
```

<210> SEQ ID NO 26
<211> LENGTH: 329
<212> TYPE: PRT
<213> ORGANISM: Bos taurus
<220> FEATURE:
<223> OTHER INFORMATION: Bos Taurus calponin 3 (acidic)

<400> SEQUENCE: 26

```
Met Thr His Phe Asn Lys Gly Pro Ser Tyr Gly Leu Ser Ala Glu Val
1               5                   10                  15

Lys Asn Lys Ile Ala Ser Lys Tyr Asp His Gln Ala Glu Glu Asp Leu
            20                  25                  30

Arg Asn Trp Ile Glu Glu Val Thr Gly Met Ser Ile Gly Ala Asn Phe
        35                  40                  45

Gln Leu Gly Leu Lys Asp Gly Ile Ile Leu Cys Glu Leu Ile Asn Lys
    50                  55                  60

Leu Gln Pro Gly Ser Val Lys Lys Val Asn Glu Ser Ser Leu Asn Trp
65                  70                  75                  80

Pro Gln Leu Glu Asn Ile Gly Asn Phe Ile Lys Ala Ile Gln Ala Tyr
                85                  90                  95

Gly Met Lys Pro His Asp Ile Phe Glu Ala Asn Asp Leu Phe Glu Asn
            100                 105                 110

Gly Asn Met Thr Gln Val Gln Thr Thr Leu Val Ala Leu Ala Gly Leu
        115                 120                 125

Ala Lys Thr Lys Gly Phe His Thr Thr Ile Asp Ile Gly Val Lys Tyr
    130                 135                 140

Ala Glu Lys Gln Thr Arg Arg Phe Asp Glu Gly Lys Leu Lys Ala Gly
145                 150                 155                 160

Gln Ser Val Ile Gly Leu Gln Met Gly Thr Asn Lys Cys Ala Ser Gln
                165                 170                 175

Ala Gly Met Thr Ala Tyr Gly Thr Arg Arg His Leu Tyr Asp Pro Lys
            180                 185                 190

Met Gln Thr Asp Lys Pro Phe Asp Gln Thr Thr Ile Ser Leu Gln Met
        195                 200                 205

Gly Thr Asn Lys Gly Ala Ser Gln Ala Gly Met Leu Ala Pro Gly Thr
    210                 215                 220

Arg Arg Asp Ile Tyr Asp Gln Lys Leu Thr Leu Gln Pro Val Asp Asn
225                 230                 235                 240

Ser Thr Ile Ser Leu Gln Met Gly Thr Asn Lys Val Ala Ser Gln Lys
                245                 250                 255

Gly Met Ser Val Tyr Gly Leu Gly Arg Gln Val Tyr Asp Pro Lys Tyr
            260                 265                 270
```

```
Cys Ala Ala Pro Thr Glu Pro Val Ile His Asn Gly Ser Gln Gly Thr
            275                 280                 285

Gly Thr Asn Gly Ser Glu Ile Ser Asp Ser Asp Tyr Gln Ala Glu Tyr
        290                 295                 300

Pro Asp Glu Tyr His Gly Glu Tyr Gln Asp Asp Tyr Pro Arg Asp Tyr
305                 310                 315                 320

Gln Tyr Gly Asp Gln Gly Ile Asp Tyr
                325
```

<210> SEQ ID NO 27
<211> LENGTH: 2005
<212> TYPE: DNA
<213> ORGANISM: Mus musculus
<220> FEATURE:
<223> OTHER INFORMATION: Mouse calponin 3 (acidic)

<400> SEQUENCE: 27

| | | | | | |
|---|---|---|---|---|---|
| tggggcagcg | agcagggcag | ccggtcccag | tccagagcga | cccggagcct | ccgcgggact | 60 |
| cgagtcctag | cgaacctcga | agcatcatcc | gcgtccgtct | gcggcgttcg | ggcttctccg | 120 |
| gcgccgcgca | ggggagcgag | ctcgtgcatc | acccgcgcgg | ccgccgctgg | ggctaagagc | 180 |
| agggacaccg | agggtgactg | accgctagaa | ctcttccagt | cgtccaaaca | gccatgaccc | 240 |
| acttcaacaa | gggcccttcc | tacgggctct | ccgccgaagt | taagaacaag | attgcatcca | 300 |
| agtatgacca | gcaggccgag | gaagatctgc | gcaactggat | agaagaggtg | acaggcctag | 360 |
| gcattggcac | caacttccag | ctggggctga | aggacgcgat | catattgtgc | gaactcataa | 420 |
| acaagctaca | gccaggctct | gtgaagaaag | tcaacgaatc | ctcactaaat | tggccccagt | 480 |
| tggagaatat | cggcaacttc | attaaagcta | tccaggctta | cggtatgaag | ccccatgata | 540 |
| tatttgaagc | aaacgacctc | tttgagaatg | caacatgac | ccaggttcag | acgacgctgg | 600 |
| tggctctagc | aggtctggcg | aaaacaaaag | gattccatac | aaccattgac | attggcgtta | 660 |
| agtatgcaga | aaaacaaaca | agacgttttg | atgaaggcaa | attaaaggct | ggccagagtg | 720 |
| taattggttt | acagatgggt | accaacaaat | gtgccagcca | ggcgggcatg | acagcctatg | 780 |
| ggactcggag | gcatctttat | gatcccaaga | tgcagacgga | caaacccttt | gaccagacca | 840 |
| cgattagcct | gcagatgggc | accaacaaag | gggccagcca | ggctgggatg | ttagcaccgg | 900 |
| gcaccagaag | agacatctat | gaccagaagc | tgacattaca | gccagtggac | aactcgacca | 960 |
| tttctctaca | gatgggcacc | aacaaagttg | cttcccagaa | aggaatgagc | gtgtatgggc | 1020 |
| ttgggcggca | agtatatgac | cccaagtact | gtgccgcacc | cacagaacct | gtcattcaca | 1080 |
| acggaagcca | gggcacgggc | accaatgggt | cggaaatcag | tgatagcgat | tatcaggcag | 1140 |
| aataccccga | tgaatatcat | ggcgagtacc | agacgactac | ccctcgggag | taccagtatg | 1200 |
| gcgacgacca | gggcattgat | tattagagtc | acacacagga | gcgcagtatt | tagtccattg | 1260 |
| ttttatccag | tgagacccaa | gctagccttg | aataattctt | ctctcgtctt | cctgaaacac | 1320 |
| tattatgctt | gttgtacctt | taaagtatgc | cttatgtaca | ttcctttctc | cttttcctgc | 1380 |
| ctcctcccta | aatagctgcc | ttctagtgct | gtagcaaggg | agccctactg | catagccagt | 1440 |
| aactcgcgtc | tgtaccatgg | aaagggcgga | acgattctcc | aggacagcca | gctctttcgt | 1500 |
| tgaagatcta | tctatgcatt | ttttacact | tacacataaa | ctggtatttt | cgaacaatag | 1560 |
| gaaactattt | tttctccttt | ttttacagtt | ttagtacgta | tctggcttgt | atgtggaaga | 1620 |
| ctaaaaagtt | gatttgctaa | atgtggtctt | tgccaactaa | aatctgagat | gcagctttag | 1680 |
| accctgacac | gtggatgttc | ttctgcagtc | ttgtctgcta | agtttttaaat | aaagtcatga | 1740 |

```
tcagtgtgca tttgtgatta catgtgtact cattctttc ccaagctgac gaggtctctc     1800
ccgagtggcg cttcgaaagg cgtgcatgca gaaatggccg aggacatgca ggtttgggtg     1860
gtgtgcctgc agacttcatt tgtgccaatg tattactgta gagtcgctct gtttccttca     1920
actgtattta ttgctgcgtt tctcagcata aacttatccc attgtatttt ttataaataa     1980 atatttttt ttgaacattc atatg                                             2005
```

<210> SEQ ID NO 28
<211> LENGTH: 330
<212> TYPE: PRT
<213> ORGANISM: Mus musculus
<220> FEATURE:
<223> OTHER INFORMATION: Mouse calponin 3 (acidic)

<400> SEQUENCE: 28

```
Met Thr His Phe Asn Lys Gly Pro Ser Tyr Gly Leu Ser Ala Glu Val
1               5                   10                  15

Lys Asn Lys Ile Ala Ser Lys Tyr Asp Gln Gln Ala Glu Glu Asp Leu
            20                  25                  30

Arg Asn Trp Ile Glu Glu Val Thr Gly Leu Gly Ile Gly Thr Asn Phe
        35                  40                  45

Gln Leu Gly Leu Lys Asp Gly Ile Ile Leu Cys Glu Leu Ile Asn Lys
    50                  55                  60

Leu Gln Pro Gly Ser Val Lys Lys Val Asn Glu Ser Ser Leu Asn Trp
65                  70                  75                  80

Pro Gln Leu Glu Asn Ile Gly Asn Phe Ile Lys Ala Ile Gln Ala Tyr
                85                  90                  95

Gly Met Lys Pro His Asp Ile Phe Glu Ala Asn Asp Leu Phe Glu Asn
            100                 105                 110

Gly Asn Met Thr Gln Val Gln Thr Thr Leu Val Ala Leu Ala Gly Leu
        115                 120                 125

Ala Lys Thr Lys Gly Phe His Thr Thr Ile Asp Ile Gly Val Lys Tyr
    130                 135                 140

Ala Glu Lys Gln Thr Arg Arg Phe Asp Glu Gly Lys Leu Lys Ala Gly
145                 150                 155                 160

Gln Ser Val Ile Gly Leu Gln Met Gly Thr Asn Lys Cys Ala Ser Gln
                165                 170                 175

Ala Gly Met Thr Ala Tyr Gly Thr Arg Arg His Leu Tyr Asp Pro Lys
            180                 185                 190

Met Gln Thr Asp Lys Pro Phe Asp Gln Thr Thr Ile Ser Leu Gln Met
        195                 200                 205

Gly Thr Asn Lys Gly Ala Ser Gln Ala Gly Met Leu Ala Pro Gly Thr
    210                 215                 220

Arg Arg Asp Ile Tyr Asp Gln Lys Leu Thr Leu Gln Pro Val Asp Asn
225                 230                 235                 240

Ser Thr Ile Ser Leu Gln Met Gly Thr Asn Lys Val Ala Ser Gln Lys
                245                 250                 255

Gly Met Ser Val Tyr Gly Leu Gly Arg Gln Val Tyr Asp Pro Lys Tyr
            260                 265                 270

Cys Ala Ala Pro Thr Glu Pro Val Ile His Asn Gly Ser Gln Gly Thr
        275                 280                 285

Gly Thr Asn Gly Ser Glu Ile Ser Asp Ser Tyr Gln Ala Glu Tyr
    290                 295                 300

Pro Asp Glu Tyr His Gly Glu Tyr Pro Asp Asp Tyr Pro Arg Glu Tyr
305                 310                 315                 320
```

Gln Tyr Gly Asp Asp Gln Gly Ile Asp Tyr
            325                 330

<210> SEQ ID NO 29
<211> LENGTH: 1932
<212> TYPE: DNA
<213> ORGANISM: Rattus norvegicus
<220> FEATURE:
<223> OTHER INFORMATION: Rat calponin 3 (acidic)

<400> SEQUENCE: 29

| | | | | | |
|---|---|---|---|---|---|
| agcagagcag | tcggtcccac | tccagtgcga | cccggagcct | ctgcgggact | cgagtccgag | 60 |
| cgaacctcga | agcatcatcc | gcgtccgtct | gccgcgttcc | ggcttctgcg | ccgcgcagag | 120 |
| tagcgagctt | gtgcatcacc | cgcgcggcca | cagctggggg | ctaagagcag | ggacaccgag | 180 |
| ggtgactgac | cccgactccg | agcgcagccc | cttcctgtgg | tccgaacagc | catgacccac | 240 |
| ttcaacaagg | gcccttccta | cgggctctcc | gccgaggtca | gaacaagat | cgcatccaag | 300 |
| tatgaccagc | aggccgagga | ggatctgcgc | aactggatag | aagaggtgac | aggcatgggc | 360 |
| attgggacca | acttccagct | gggcctgaag | gacggtatca | tcctctgcga | actcataaac | 420 |
| aagctacagc | caggctctgt | gaagaaagtc | aacgagtcct | cactaaactg | gccgcagttg | 480 |
| gagaacatcg | gcaactttat | taaagccatc | caggcttacg | gtatgaagcc | ccatgacata | 540 |
| tttgaggcaa | acgacctttt | tgagaatggc | aacatgaccc | aggttcagac | tacgctggtg | 600 |
| gctctagcag | gtctggcgaa | acaaaagga | ttccatacaa | ccattgacat | cggcgttaag | 660 |
| tacgcagaaa | acagacacg | acgcttcgat | gaaggcaagc | taaggctgg | ccaaagtgta | 720 |
| atcggtttac | agatggggac | caacaaatgt | gccagccagg | cgggtatgac | agcctatggg | 780 |
| actcggaggc | atctttatga | tcccaaaatg | cagactgaca | aacccttga | ccagaccacc | 840 |
| atcagtctgc | agatgggcac | caacaaagga | gccagccagg | ctggcatgtc | ggcaccgggt | 900 |
| accagaagag | acatctatga | ccagaagcta | acattacagc | cggtggacaa | ctcgaccatt | 960 |
| tctctacaga | tgggcaccaa | caaagttgct | tcccagaaag | gaatgagcgt | gtatgggctt | 1020 |
| gggcggcaag | tgtatgaccc | caagtactgt | gccgcaccca | cagaacctgt | cattcacaac | 1080 |
| ggaagccagg | gcacgggaac | aaatgggtca | gaaatcagtg | atagcgatta | ccaggcagaa | 1140 |
| taccccgatg | agtatcatgg | cgagtaccca | gatgagtacc | ctcgagagta | ccagtatggt | 1200 |
| gacgaccagg | gcatcgatta | ctagagtcac | acacaggagt | gcagtatttt | agtccattgt | 1260 |
| ttatccagtg | agacccaagc | tagccttgag | taattcttat | ctcgtcttcc | taaacactat | 1320 |
| tacgcttcct | gtacctttaa | agaatgcctt | acgtacattc | ctttctccct | ttcctgcctc | 1380 |
| ctccctaaat | tgccttctag | tgctgtagcg | agggaagcct | acagcctaac | cagtaactcg | 1440 |
| cgttggaaga | agtgagaagg | aacgctgtgc | gagggcagcc | agctctttcg | ctggagatct | 1500 |
| ataaaatttt | ttacacttac | acgtaaactg | gtattttcaa | acaataggaa | actatttttt | 1560 |
| tcttttttac | agtttagtat | gtatctggct | tgtacacggt | agactaagaa | gttgatttgc | 1620 |
| taagtgtggt | ctttgccaag | taatctaaca | tgcagcttta | gaacctgaca | cgtggatgct | 1680 |
| tctgcacagt | gttgtctgct | aagttttaaa | taaagtcgtg | atcagtgtga | ttcgtgatta | 1740 |
| catgtgtact | cattctttcc | cgaagctgac | aaggtctctc | ccgagtggcg | ctctaaaggc | 1800 |
| gcgtctacag | aaatggccgc | agacatgtag | gtgtgggtgg | cgtgcctgca | gacttcattt | 1860 |
| gtgccaatgt | attactgtag | agtcgctgtt | cccttcaact | gtatttattg | ctgcatttct | 1920 |
| cagcataaac | tt | | | | | 1932 |

```
<210> SEQ ID NO 30
<211> LENGTH: 330
<212> TYPE: PRT
<213> ORGANISM: Rattus norvegicus
<220> FEATURE:
<223> OTHER INFORMATION: Rat calponin 3 (acidic)

<400> SEQUENCE: 30

Met Thr His Phe Asn Lys Gly Pro Ser Tyr Gly Leu Ser Ala Glu Val
1               5                   10                  15

Lys Asn Lys Ile Ala Ser Lys Tyr Asp Gln Gln Ala Glu Glu Asp Leu
            20                  25                  30

Arg Asn Trp Ile Glu Glu Val Thr Gly Met Gly Ile Gly Thr Asn Phe
        35                  40                  45

Gln Leu Gly Leu Lys Asp Gly Ile Ile Leu Cys Glu Leu Ile Asn Lys
    50                  55                  60

Leu Gln Pro Gly Ser Val Lys Lys Val Asn Glu Ser Ser Leu Asn Trp
65                  70                  75                  80

Pro Gln Leu Glu Asn Ile Gly Asn Phe Ile Lys Ala Ile Gln Ala Tyr
                85                  90                  95

Gly Met Lys Pro His Asp Ile Phe Glu Ala Asn Asp Leu Phe Glu Asn
            100                 105                 110

Gly Asn Met Thr Gln Val Gln Thr Thr Leu Val Ala Leu Ala Gly Leu
        115                 120                 125

Ala Lys Thr Lys Gly Phe His Thr Thr Ile Asp Ile Gly Val Lys Tyr
    130                 135                 140

Ala Glu Lys Gln Thr Arg Arg Phe Asp Glu Gly Lys Leu Lys Ala Gly
145                 150                 155                 160

Gln Ser Val Ile Gly Leu Gln Met Gly Thr Asn Lys Cys Ala Ser Gln
                165                 170                 175

Ala Gly Met Thr Ala Tyr Gly Thr Arg Arg His Leu Tyr Asp Pro Lys
            180                 185                 190

Met Gln Thr Asp Lys Pro Phe Asp Gln Thr Thr Ile Ser Leu Gln Met
        195                 200                 205

Gly Thr Asn Lys Gly Ala Ser Gln Ala Gly Met Ser Ala Pro Gly Thr
    210                 215                 220

Arg Arg Asp Ile Tyr Asp Gln Lys Leu Thr Leu Gln Pro Val Asp Asn
225                 230                 235                 240

Ser Thr Ile Ser Leu Gln Met Gly Thr Asn Lys Val Ala Ser Gln Lys
                245                 250                 255

Gly Met Ser Val Tyr Gly Leu Gly Arg Gln Val Tyr Asp Pro Lys Tyr
            260                 265                 270

Cys Ala Ala Pro Thr Glu Pro Val Ile His Asn Gly Ser Gln Gly Thr
        275                 280                 285

Gly Thr Asn Gly Ser Glu Ile Ser Asp Ser Tyr Gln Ala Glu Tyr
    290                 295                 300

Pro Asp Glu Tyr His Gly Glu Tyr Pro Asp Gly Tyr Pro Arg Glu Tyr
305                 310                 315                 320

Gln Tyr Gly Asp Asp Gln Gly Ile Asp Tyr
            325                 330
```